US009957258B2

(12) United States Patent
Kunimoto et al.

(10) Patent No.: US 9,957,258 B2
(45) Date of Patent: May 1, 2018

(54) OXIME ESTER PHOTOINITIATORS

(71) Applicant: BASF SE, Ludwigshafen (DE)

(72) Inventors: Kazuhiko Kunimoto, Kawanishi (JP);
Hisatoshi Kura, Takarazuka (JP);
Hiroshi Yamamoto, Takarazuka (JP);
Yumiko Nakagawa, Amagasaki (JP);
Toshikage Asakura, Minoo (JP); Kaori Sameshima, Tondabayashi (JP)

(73) Assignee: BASF SE, Ludwigshafen am Rhein (DE)

( * ) Notice: Subject to any disclaimer, the term of this patent is extended or adjusted under 35 U.S.C. 154(b) by 82 days.

(21) Appl. No.: 14/917,508

(22) PCT Filed: Sep. 8, 2014

(86) PCT No.: PCT/IB2014/064309
§ 371 (c)(1),
(2) Date: Mar. 8, 2016

(87) PCT Pub. No.: WO2015/036910
PCT Pub. Date: Mar. 19, 2015

(65) Prior Publication Data
US 2016/0214966 A1 Jul. 28, 2016

(30) Foreign Application Priority Data

Sep. 10, 2013 (EP) .................................... 13183651

(51) Int. Cl.
| | | |
|---|---|---|
| *G03F 7/031* | (2006.01) |
| *C07D 409/06* | (2006.01) |
| *C07D 209/12* | (2006.01) |
| *C07D 307/56* | (2006.01) |
| *C07D 307/80* | (2006.01) |
| *C07D 307/92* | (2006.01) |
| *C07D 307/83* | (2006.01) |
| *C07D 307/86* | (2006.01) |
| *C07D 307/91* | (2006.01) |
| *C07D 333/56* | (2006.01) |
| *C07D 407/12* | (2006.01) |
| *G02B 5/20* | (2006.01) |
| *G02B 5/22* | (2006.01) |
| *G03F 7/00* | (2006.01) |
| *G03F 7/20* | (2006.01) |
| *G03F 7/32* | (2006.01) |

(52) U.S. Cl.
CPC ......... *C07D 409/06* (2013.01); *C07D 209/12* (2013.01); *C07D 307/56* (2013.01); *C07D 307/80* (2013.01); *C07D 307/83* (2013.01); *C07D 307/86* (2013.01); *C07D 307/91* (2013.01); *C07D 307/92* (2013.01); *C07D 333/56* (2013.01); *C07D 407/12* (2013.01); *G02B 5/201* (2013.01); *G02B 5/223* (2013.01); *G03F 7/0007* (2013.01); *G03F 7/031* (2013.01); *G03F 7/20* (2013.01); *G03F 7/32* (2013.01)

(58) Field of Classification Search
CPC .......... G03F 7/0007; G03F 7/031; G03F 7/20; C07D 409/06; C07D 209/12; C07D 307/56; C07D 307/80; C07D 307/83; C07D 307/86; C07D 307/91; C07D 307/92; C07D 333/56; C07D 407/12; G02B 5/201; G02B 5/223
USPC ...................................... 430/7, 270.1, 281.1
See application file for complete search history.

(56) References Cited

U.S. PATENT DOCUMENTS

| | | | |
|---|---|---|---|
| 3,579,339 | A | 5/1971 | Chang et al. |
| 4,575,330 | A | 3/1986 | Hull |
| 4,622,286 | A | 11/1986 | Sheets |
| 4,934,791 | A | 6/1990 | Shimizu et al. |
| 4,970,244 | A | 11/1990 | Komai et al. |
| 4,977,511 | A | 12/1990 | Gottschalk et al. |
| 5,368,976 | A | 11/1994 | Tajima et al. |
| 5,376,459 | A | 12/1994 | Christner et al. |
| 5,587,404 | A | 12/1996 | Kröner et al. |
| 5,650,263 | A | 7/1997 | Wakata et al. |
| 5,719,008 | A | 2/1998 | Hozumi et al. |
| 5,800,952 | A | 9/1998 | Urano et al. |
| 5,821,016 | A | 10/1998 | Satoh et al. |
| 5,840,465 | A | 11/1998 | Kakinuma et al. |
| 5,847,015 | A | 12/1998 | Tajima et al. |
| 5,853,446 | A | 12/1998 | Carre et al. |
| 5,863,678 | A | 1/1999 | Urano et al. |
| 5,866,298 | A | 2/1999 | Iwamoto et al. |
| 5,879,855 | A | 3/1999 | Schädeli et al. |
| 5,882,843 | A | 3/1999 | Kudo et al. |

(Continued)

FOREIGN PATENT DOCUMENTS

| | | |
|---|---|---|
| CN | 1514845 | 7/2004 |
| CN | 1514845 A | 7/2004 |

(Continued)

OTHER PUBLICATIONS

Computer-generated translation of JP 2009-173560 (Aug. 2009).*
Chinese Office Action for Chinese Application No. 201480049636. 3, dated Jun. 23, 2017.
Supplementary European Search Report for European Application No. EP 14844439, dated Jul. 6, 2017.
International Search Report for PCT/IB2014/064309 dated Jan. 6, 2015.

(Continued)

*Primary Examiner* — John A McPherson
(74) *Attorney, Agent, or Firm* — Drinker Biddle & Reath LLP

(57) ABSTRACT

Disclosed are oxime ester compounds which have specific benzo (unsaturated 5-membered ring)-carbonyl group and their use as photoinitiators in photopolymerizable compositions, in particular in photoresist formulations for display applications, e.g. liquid crystal display (LCD), organic light emitting diode (OLED) and touch panel.

19 Claims, No Drawings

(56) References Cited

U.S. PATENT DOCUMENTS

| | | | |
|---|---|---|---|
| 5,897,981 A | 4/1999 | Kobayashi et al. | |
| 5,969,867 A | 10/1999 | Fukushima et al. | |
| 6,342,332 B1 | 1/2002 | Loo et al. | |
| 6,437,918 B1 | 8/2002 | Hamanaka et al. | |
| 6,485,885 B1 | 11/2002 | Oka et al. | |
| 6,596,445 B1 | 7/2003 | Matsumoto et al. | |
| 6,806,024 B1 | 10/2004 | Kura et al. | |
| 7,189,489 B2 | 3/2007 | Kunimoto et al. | |
| 7,648,738 B2 | 1/2010 | Tanabe et al. | |
| 8,659,724 B2 | 2/2014 | Hagiwara et al. | |
| 2001/0012596 A1 | 8/2001 | Kunimoto et al. | |
| 2002/0020832 A1 | 2/2002 | Oka et al. | |
| 2004/0170924 A1 | 9/2004 | Kunimoto et al. | |
| 2005/0191567 A1 | 9/2005 | Kunimoto et al. | |
| 2006/0241259 A1* | 10/2006 | Tanabe | C07D 207/333 526/217 |
| 2008/0096115 A1 | 4/2008 | Tanabe et al. | |
| 2009/0087759 A1 | 4/2009 | Matsumoto et al. | |
| 2009/0292039 A1 | 11/2009 | Sawamoto et al. | |
| 2010/0086881 A1 | 4/2010 | Matsumoto et al. | |
| 2010/0136467 A1 | 6/2010 | Matsumoto et al. | |
| 2010/0136491 A1 | 6/2010 | Matsumoto et al. | |
| 2010/0188765 A1 | 7/2010 | Matsumoto et al. | |
| 2011/0134554 A1 | 6/2011 | Matsumoto et al. | |
| 2011/0170209 A1 | 7/2011 | Matsumoto et al. | |
| 2011/0218266 A1 | 9/2011 | Studer et al. | |
| 2013/0188270 A1 | 7/2013 | Nishimae et al. | |
| 2014/0212749 A1 | 7/2014 | Choi et al. | |
| 2014/0334027 A1 | 11/2014 | Nishimae et al. | |
| 2015/0056554 A1 | 2/2015 | Matsumoto et al. | |
| 2015/0064624 A1 | 3/2015 | Nishimae et al. | |

FOREIGN PATENT DOCUMENTS

| | | |
|---|---|---|
| CN | 1602855 | 4/2005 |
| CN | 1720245 A | 1/2006 |
| CN | 1241562 | 2/2006 |
| CN | 101525393 A | 9/2009 |
| CN | 101941939 A | 1/2011 |
| CN | 102492060 A | 6/2012 |
| CN | 103044581 A | 4/2013 |
| DE | 19700064 A1 | 7/1997 |
| EP | 126541 A1 | 11/1984 |
| EP | 320264 A2 | 6/1989 |
| EP | 339841 A2 | 11/1989 |
| EP | 438123 A2 | 7/1991 |
| EP | 441232 A2 | 8/1991 |
| EP | 497531 A2 | 8/1992 |
| EP | 511403 A1 | 11/1992 |
| EP | 678534 A1 | 10/1995 |
| EP | 706091 A1 | 4/1996 |
| EP | 780729 A1 | 6/1997 |
| EP | 855731 A1 | 7/1998 |
| EP | 863534 A2 | 9/1998 |
| EP | 881541 A1 | 12/1998 |
| EP | 0932256 A1 | 7/1999 |
| EP | 2072500 A1 | 6/2009 |
| GB | 2180358 A | 3/1987 |
| JP | S5742009 A | 3/1982 |
| JP | 60-38989 A | 2/1985 |
| JP | S6072927 A | 4/1985 |
| JP | S60165623 A | 8/1985 |
| JP | S60166946 A | 8/1985 |
| JP | S6167003 A | 4/1986 |
| JP | S61153602 A | 7/1986 |
| JP | H01130103 A | 5/1989 |
| JP | H01134306 A | 5/1989 |
| JP | H0567405 A | 3/1993 |
| JP | H05173320 A | 7/1993 |
| JP | H05271576 A | 10/1993 |
| JP | HEI 6-68309 | 3/1994 |
| JP | H06230212 A | 8/1994 |
| JP | H08171863 A | 7/1996 |
| JP | H08305019 A | 11/1996 |
| JP | H09179299 A | 7/1997 |
| JP | H09244230 A | 9/1997 |
| JP | H09269410 A | 10/1997 |
| JP | H09325209 A | 12/1997 |
| JP | H1010718 A | 1/1998 |
| JP | H1062980 A | 3/1998 |
| JP | H1090516 A | 4/1998 |
| JP | H10171119 A | 6/1998 |
| JP | H10221843 A | 8/1998 |
| JP | H11174459 A | 7/1999 |
| JP | H11174464 A | 7/1999 |
| JP | 2000039503 A | 2/2000 |
| JP | 2000081701 A | 3/2000 |
| JP | 2002206014 A | 7/2002 |
| JP | 2003015288 A1 | 1/2003 |
| JP | 2004069754 A | 3/2004 |
| JP | 2004302245 A | 10/2004 |
| JP | 2005077451 A | 3/2005 |
| JP | 2005316449 A | 11/2005 |
| JP | 2005338328 A | 12/2005 |
| JP | 3754065 B2 | 3/2006 |
| JP | 2009-173560 A * | 8/2009 |
| JP | 2010015025 A | 1/2010 |
| JP | 2010049238 A | 3/2010 |
| JP | 2011065133 A | 3/2011 |
| KR | 20090008811 A | 1/2009 |
| KR | 20130003305 A | 1/2013 |
| KR | 20130010621 A | 1/2013 |
| KR | 201225695 A1 | 7/2014 |
| TW | 200422296 A | 11/2004 |
| TW | 200840813 A | 10/2008 |
| WO | WO-9641240 A1 | 12/1996 |
| WO | WO-99/38035 A1 | 7/1999 |
| WO | WO-01090113 A1 | 11/2001 |
| WO | WO-03021358 A1 | 3/2003 |
| WO | WO-03029332 A1 | 4/2003 |
| WO | WO-2004050653 A2 | 6/2004 |
| WO | WO-04081100 A1 | 9/2004 |
| WO | WO-050800337 A1 | 9/2005 |
| WO | WO-07062963 A1 | 6/2007 |
| WO | WO2007071497 | 6/2007 |
| WO | WO-2007071497 A1 | 6/2007 |
| WO | WO-2008078678 A1 | 7/2008 |
| WO | WO-08138724 A1 | 11/2008 |
| WO | WO-2009147031 A2 | 12/2009 |
| WO | WO-2010060702 A1 | 6/2010 |
| WO | WO-2012101245 A1 | 8/2012 |

OTHER PUBLICATIONS

Taiwan Office Action with English Translation for Taiwanese Application No. 103131032, dated Dec. 21, 2017.

\* cited by examiner

OXIME ESTER PHOTOINITIATORS

CROSS-REFERENCE TO RELATED APPLICATIONS

This application is a national stage application (under 35 U.S.C. § 371) of PCT/IB2014/064309, filed Sep. 8, 2014, which claims benefit of European Application No. 13183651.2, filed Sep. 10, 2013, both applications of which are incorporated herein by reference in their entirety.

The invention pertains to new oxime ester compounds which have specific benzo(unsaturated 5-membered ring)-carbonyl group and their use as photoinitiators in photopolymerizable compositions, in particular in photoresist formulations for display applications, e.g. liquid crystal display (LCD), organic light emitting diode (OLED) and touch panel.

BACKGROUND OF THE INVENTION

Oxime ester compounds having hetroaryl moieties are known in the art. For example in CN103044581A macromolecular photoinitiators their preparation method and application thereof in photocurable compositions are provided. KR1225695B1 discloses α-ketoxime ester compounds as photopolymerization initiators. In KR2013003305A oximino dithiocarbonate compounds, containing furan-2-yl, 3-methylthiophen-2-yl, or 2-methylphenyl group are described as photoinitiators. CN102492060B discloses a diphenyl sulfide oxime ester type photoinitiator which comprises a O or S-containing heterocyclic radical substituted aryl or aryl with at least one substituent containing O or S.

The synthesis of certain iminonaphtho[2,3-b]furan derivatives from their respective carbonyl precursors in the regiospecific and the stereospecific manners are described in *Bioorganic & Medicinal Chemistry*, Volume: 18, Issue: 14, Pages: 5172-5182. KR2013010621A discloses the preparation of an oxime ester compound by reacting a 9H-carbazole-based compound with dicyclohexylcarbodiimide by a dehydration condensation reaction.

Further oxime ester compounds are for example provided in WO2010/060702 and WO08138724. WO 2004050653 A2 discloses oxime ester photoinitiators with heteroaromatic groups.

Color filters (CF) for LCD and white OLED, which comprise a black matrix and red, green and blue color pixels on a glass substrate, are manufactured by photolithography using radically photopolymerizable resists.

Overcoat layers for LCD are used to planarize a surface of the color filters and enhance orientation of liquid crystal and to prevent ion elution from CF to the liquid crystal. The overcoat is manufactured using a thermosetting resin based on an acrylate resin and/or epoxy resin on the color filter by heating, for example, at 220° C. for 30 min. or in combination with photolithography prior to the post-baking process. Thermal stability, light resistance, adhesiveness, hardness and transparency are required.

Spacer for LCD, which controls a cell gap of the liquid crystal layer in LCD panels, is formed with high positional precision by photolithography using a photosensitive composition. The photospacer is manufactured by photolithography using radically polymerizable resists on overcoat or color filter. After photolithography, the photospacer is baked, for example, at 220° C. for 60 min. to attain thermal stability, mechanical strength, adhesiveness, cell gap controllability and high deformation restorability.

A transparent column spacer has been widely used in the LCD technology, but the transparent spacer disturbs polarized light reducing the contrast ratio. One of a possible solution is to mix with a black colorant not to scatter but to absorb the polarized light, i.e. a black column spacer. Black column spacer is also used in the LCD technology.

Also the passivation layer in the backplane for LCD and OLED can be manufactured by photo lithography, as well as the bank layer/pixel definition layer for OLED. Further the transparent conductive layer for touch panel can be manufactured by photo lithography.

Accordingly, in the market there is a strong demand for higher photosensitive photo initiators in order to reduce the energy consumption, to achieve a shorter tact time for higher productivity and/or more freedom in choice of materials for display application. The photoinitiators to be employed in the photosensitive resins Therefore have to be highly reactive, easy to prepare and easy to handle. For example, in color filter resist applications, highly pigmented resists are required for the high color quality property. With the increase of the pigment content, the curing of color resists becomes more difficult. Hence, photoinitiators having a high sensitivity are required. In addition, also such new photoinitiators must meet the high requirements of the industry regarding properties like, for example, easy handling, high solubility, thermal stability and storage stability. Furthermore the initiators in display applications should contribute to surface smoothness of a pattern, adhesiveness to the substrate etc. Further, easy access to corresponding intermediates for the preparation of the compounds should be given. Thus, there still is a need for photoinitiator compounds providing a perfect balance of the requirements as given above. E.g. an acceptable balance between accessability in view of preparation methods and processes as well as properties of the compound as for example sensitivity, solubility etc.

DETAILED DESCRIPTION OF THE INVENTION

It now has been found that compounds of the formula I or II

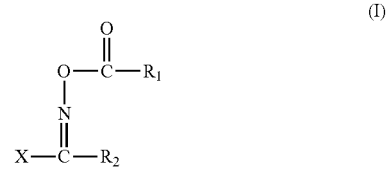

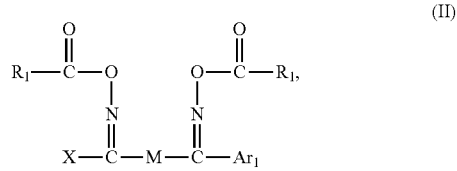

wherein
X is

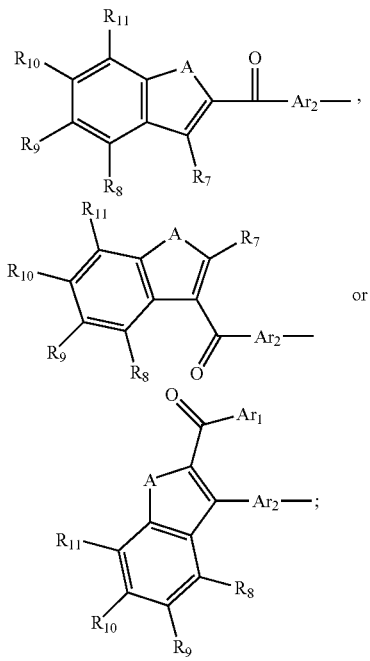

A is O, S, $NR_5$ or $CR_{16}R_{17}$;

$R_1$ is hydrogen, $C_1$-$C_{20}$alkyl which is unsubstituted or substituted by one or more substituents selected from the group consisting of halogen, $OR_3$, $SR_4$, $NR_5R_6$, CN, (CO)$OR_3$, (CO)$NR_5R_6$, $C_3$-$C_8$cycloalkyl, $C_3$-$C_8$cycloalkyl which is interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$ or $NR_5R_6$;

or $R_1$ is $C_2$-$C_{20}$alkyl interrupted by one or more O, S, $NR_5$, CO, SO or $SO_2$, which interrupted $C_2$-$C_{20}$alkyl is unsubstituted or substituted by one or more $C_3$-$C_8$cycloalkyl, OH, SH, O(CO)$R_{1a}$, (CO)$OR_3$, (CO)$NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or $R_1$ is $C_2$-$C_{12}$alkenyl or $C_3$-$C_{20}$cycloalkyl, each of which is uninterrupted or interrupted by one or more O, S, CO, $NR_5$ or $COOR_3$;

or $R_1$ is $C_6$-$C_{20}$aryl or $C_3$-$C_{20}$heteroaryl, each of which is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_3$, $SR_4$, $NR_5R_6$, $COOR_3$, (CO)$R_{1a}$ or $SO_2$—$R_{1a}$;

or $R_1$ is $C_1$-$C_{20}$alkoxy, which is unsubstituted or substituted by one or more $C_1$-$C_{10}$alkyl, $C_1$-$C_4$haloalkyl, halogen, phenyl, $C_1$-$C_{20}$alkylphenyl or $C_1$-$C_8$alkoxyphenyl;

or $R_1$ is $C_2$-$C_{20}$alkoxy, which is interrupted by one or more O, S, $NR_5$, CO, SO or $SO_2$;

or $R_1$ is $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_3$, $SR_4$, $NR_5R_6$, $COOR_3$, (CO)$R_{1a}$ or $SO_2R_{1a}$;

$R_{1a}$ is hydrogen, $C_1$-$C_{20}$alkyl which is unsubstituted or substituted by one or more substituents selected from the group consisting of halogen, $OR_{3a}$, $SR_{4a}$, $NR_{5a}R_{6a}$, CN, (CO)$OR_{3a}$, (CO)$NR_{5a}R_{6a}$, $C_3$-$C_8$cycloalkyl which is uninterrupted or interrupted by one or more O, S, CO or $NR_{5a}$, $C_6$-$C_{20}$aryl, $C_3$-$C_{20}$heteroaryl, $C_6$-$C_{20}$aroyl and $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_{3a}$, $SR_{4a}$ or $NR_{5a}R_{6a}$;

or $R_{1a}$ is $C_2$-$C_{20}$alkyl interrupted by one or more O, S, $NR_{5a}$, CO, SO or $SO_2$, which interrupted $C_2$-$C_{20}$alkyl is unsubstituted or substituted by one or more $C_3$-$C_8$cycloalkyl, OH, SH, O(CO)—($C_1$-$C_8$alkyl), (CO)$OR_{3a}$, (CO)$NR_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_{3a}$, $SR_{4a}$ or $NR_{5a}R_{6a}$;

or $R_{1a}$ is $C_2$-$C_{12}$alkenyl or $C_3$-$C_{20}$cycloalkyl, each of which is uninterrupted or interrupted by one or more O, S, CO, $NR_{5a}$ or $COOR_{3a}$;

or $R_{1a}$ is $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_{3a}$, $SR_{4a}$, $NR_{5a}R_{6a}$, $COOR_{3a}$, (CO)—($C_1$-$C_8$alkyl), benzoyl or $SO_2$—($C_1$-$C_4$haloalkyl);

or $R_{1a}$ is $C_1$-$C_{20}$alkoxy, which is unsubstituted or substituted by one or more $C_1$-$C_{10}$alkyl, $C_1$-$C_4$haloalkyl, halogen, phenyl, $C_1$-$C_{20}$alkylphenyl or $C_1$-$C_8$alkoxyphenyl;

or $R_{1a}$ is $C_2$-$C_{20}$alkoxy, which is interrupted by one or more O, S, $NR_{5a}$, CO, SO or $SO_2$;

or $R_{1a}$ is $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_{3a}$, $SR_{4a}$, $NR_{5a}R_{6a}$, $COOR_{3a}$, (CO)($C_1$-$C_8$alkyl), $SO_2$—($C_1$-$C_4$haloalkyl), benzoyl, or

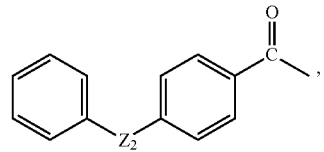

which benzoyl or

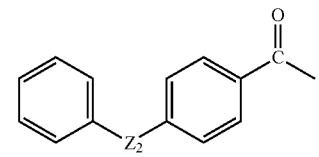

is unsubstituted or substituted by

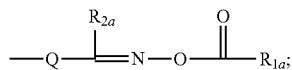

$R_2$ is hydrogen, CN, $(CO)R_{1a}$, $(CO)OR_3$, $CONR_5R_6$, $NO_2$, $PO(OR_{1a})_2$ or $S(O)_mR_{1a}$;

or $R_2$ is $C_1$-$C_{20}$alkyl which is unsubstituted or substituted by one or more substituents selected from the group consisting of halogen, $OR_3$, $SR_4$, $NR_5R_6$, CN, $(CO)OR_3$, $(CO)NR_5R_6$, $PO(OR_{1a})_2$, $S(O)_mR_{1a}$,

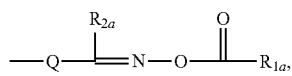

$C_3$-$C_8$cycloalkyl which is uninterrupted or interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$, $NR_5R_6$, $PO(OR_{1a})_2$ or $S(O)_mR_{1a}$;

or $R_2$ is $C_2$-$C_{20}$alkyl interrupted by one or more O, S, $NR_5$, CO, SO or $SO_2$, which interrupted $C_2$-$C_{20}$alkyl is unsubstituted or substituted by one or more $C_3$-$C_8$cycloalkyl, OH, SH, $O(CO)R_{1a}$, $(CO)OR_3$, $(CO)NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or $R_2$ is $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$;

or $R_2$ is $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_3$, $SR_4$, $NR_5R_6$, $COOR_3$, $(CO)$—$R_{1a}$ $(CO)NR_5R_6$, $PO(OR_{1a})_2$, $S(O)_mR_{1a}$,

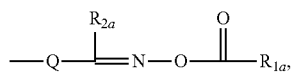

$C_1$-$C_{20}$alkyl which is unsubstituted or substituted by one or more halogen, $COOR_{3a}$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{20}$alkyl which is interrupted by one or more O, S or $NR_5$, phenyl, naphthyl, benzoyl and naphthoyl, which phenyl, naphthyl, benzoyl or naphthoyl is unsubstituted or substituted by one or more $OR_3$, $SR_4$ or $NR_5R_6$;

$R_{2a}$ is hydrogen, CN, $(CO)R_{1a}$, $(CO)OR_{3a}$, $CONR_{5a}R_{6a}$, $NO_2$, $PO(OR_{1a})_2$ or $S(O)_mR_{1a}$;

or $R_{2a}$ is $C_1$-$C_{20}$alkyl which is unsubstituted or substituted by one or more substituents selected from the group consisting of halogen, $OR_{3a}$, $SR_{4a}$, $NR_{5a}R_{6a}$, CN, $(CO)OR_{3a}$, $(CO)NR_{5a}R_{6a}$, $PO(OR_{1a})_2$, $S(O)_mR_{1a}$, $C_3$-$C_8$cycloalkyl which is uninterrupted or interrupted by one or more O, S, CO or $NR_{5a}$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_{3a}$, $SR_{4a}$, $NR_{5a}R_{6a}$, $PO(OR_{1a})_2$ or $S(O)_mR_{1a}$;

or $R_{2a}$ is $C_2$-$C_{20}$alkyl interrupted by one or more O, S, $NR_{5a}$, CO, SO or $SO_2$, which interrupted $C_2$-$C_{20}$alkyl is unsubstituted or substituted by one or more $C_3$-$C_8$cycloalkyl, OH, SH, $O(CO)R_{1a}$, $(CO)OR_{3a}$, $(CO)NR_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_{3a}$, $SR_{4a}$ or $NR_{5a}R_{6a}$;

or $R_{2a}$ is $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_{5a}$ or $COOR_{3a}$;

or $R_{2a}$ is $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_{3a}$, $SR_{4a}$, $NR_{5a}R_{6a}$, $COOR_{3a}$, $(CO)R_{1a}$ $(CO)NR_{5a}R_{6a}$, $PO(OR_{1a})_2$, $S(O)_mR_{1a}$, $C_1$-$C_{20}$alkyl which is unsubstituted or substituted by one or more halogen, $COOR_{3a}$, $CONR_{5a}R_{6a}$, phenyl, $C_3$-$C_8$cycloalkyl, $C_3$-$C_{20}$heteroaryl, $OR_{3a}$, $SR_{4a}$ or $NR_{5a}R_{6a}$;

$C_2$-$C_{20}$alkyl which is interrupted by one or more O, S or $NR_{5a}$, phenyl, naphthyl, benzoyl and naphthoyl, each of which phenyl, naphthyl, benzoyl or naphthoyl is unsubstituted or substituted by one or more $OR_{3a}$, $SR_{4a}$ or $NR_{5a}R_{6a}$;

$R_3$ is hydrogen, $(CO)R_{1a}$, $(CO)OR_{3a}$, $CONR_5R_6$, $C_1$-$C_{20}$alkyl which is unsubstituted or substituted by one or more substituents selected from the group consisting of halogen, $OR_{3a}$, $SR_{4a}$, $NR_{5a}R_{6a}$, CN, $(CO)OR_{3a}$, $(CO)NR_{5a}R_{6a}$, $PO(OR_{1a})_2$, $S(O)_mR_{1a}$, $C_3$-$C_8$cycloalkyl which is uninterrupted or interrupted by one or more O, S, CO or $NR_{5a}$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_{3a}$, $SR_{4a}$, $NR_{5a}R_{6a}$, $PO(OR_{1a})_2$ or $S(O)_mR_{1a}$;

or $R_3$ is $C_2$-$C_{20}$alkyl interrupted by one or more O, S, $NR_{5a}$, CO, SO or $SO_2$, which interrupted $C_2$-$C_{20}$alkyl is unsubstituted or substituted by one or more $C_3$-$C_8$cycloalkyl, OH, SH, $O(CO)R_{1a}$, $(CO)OR_{3a}$, $(CO)NR_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_{3a}$, $SR_{4a}$ or $NR_{5a}R_{6a}$;

or $R_3$ is $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_{5a}$ or $COOR_{3a}$;

or $R_3$ is $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_{3a}$, $SR_{4a}$, $NR_{5a}R_{6a}$, $COOR_{3a}$, $(CO)R_{1a}$ $(CO)NR_{5a}R_{6a}$, $PO(OR_{1a})_2$, $S(O)_mR_{1a}$,

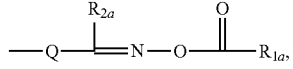

C₁-C₂₀alkyl which is unsubstituted or substituted by one or more halogen, COOR$_{3a}$, CONR$_{5a}$R$_{6a}$, phenyl, C$_3$-C$_8$cycloalkyl, C$_3$-C$_{20}$heteroaryl, OR$_{3a}$, SR$_{4a}$ or NR$_{5a}$R$_{6a}$, C$_2$-C$_{20}$alkyl which is interrupted by one or more O, S or NR$_{5a}$;

phenyl, naphthyl, benzoyl and naphthoyl, which phenyl, naphthyl, benzoyl or naphthoyl is unsubstituted or substituted by one or more OR$_{3a}$, SR$_{4a}$ or NR$_{5a}$R$_{6a}$;

or R$_3$ together with one of the carbon atoms of R$_2$ or M forms a 5- or 6-membered saturated or unsaturated ring which is uninterrupted or interrupted by O, S or NR$_{5a}$, and which 5- or 6-membered saturated or unsaturated ring is unsubstituted or substituted by one or more C$_1$-C$_{20}$alkyl, OR$_{3a}$, SR$_{4a}$, NR$_{5a}$R$_{6a}$, (CO)R$_{1a}$, NO$_2$, halogen, C$_1$-C$_4$-haloalkyl, CN, phenyl, C$_1$-C$_{20}$alkylphenyl, C$_1$-C$_8$alkoxyphenyl,

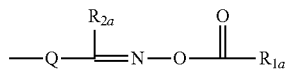

or C$_3$-C$_{20}$cyclalkyl which is uninterrupted or interrupted by one or more O, S, CO or NR$_{5a}$;

R$_{3a}$ is hydrogen, (CO)O(C$_1$-C$_8$alkyl) or CON(C$_1$-C$_8$alkyl)$_2$;

or R$_{3a}$ is C$_1$-C$_{20}$alkyl which is unsubstituted or substituted by one or more substituents selected from the group consisting of halogen, OH, SH, CN, C$_3$-C$_8$alkenoxy, OCH$_2$CH$_2$CN, OCH$_2$CH$_2$(CO)O(C$_1$-C$_8$alkyl), O(CO)(C$_1$-C$_8$alkyl), O(CO)(C$_2$-C$_4$)alkenyl, O(CO)phenyl, (CO)OH, (CO)O(C$_1$-C$_8$alkyl), C$_3$-C$_8$cycloalkyl, SO$_2$(C$_1$-C$_4$haloalkyl), O(C$_1$-C$_4$haloalkyl), phenyl, C$_1$-C$_8$alkylphenyl, C$_1$-C$_8$alkoxyphenyl and C$_3$-C$_8$cycloalkyl which is interrupted by one or more O;

or R$_{3a}$ is C$_2$-C$_{20}$alkyl interrupted by one or more O, S, N(C$_1$-C$_8$alkyl), CO, SO or SO$_2$, which interrupted C$_2$-C$_{20}$alkyl is unsubstituted or substituted by one or more C$_3$-C$_8$cycloalkyl, OH, SH, O(CO)(C$_1$-C$_8$alkyl), (CO)O(C$_1$-C$_8$alkyl), (CO)N(C$_1$-C$_8$alkyl)$_2$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, C$_1$-C$_8$alkyl, C$_1$-C$_8$alkoxy, C$_1$-C$_8$alkylsulfanyl or N(C$_1$-C$_8$alkyl)$_2$;

or R$_{3a}$ is C$_2$-C$_{12}$alkenyl or C$_3$-C$_8$cycloalkyl, which C$_2$-C$_{12}$alkenyl or C$_3$-C$_8$cycloalkyl is uninterrupted or interrupted by one or more O, S, CO, N(C$_1$-C$_8$alkyl) or COO(C$_1$-C$_8$alkyl);

or R$_{3a}$ is C$_6$-C$_{20}$aryl, C$_3$-C$_{20}$heteroaryl, C$_6$-C$_{20}$aroyl or C$_3$-C$_{20}$heteroarylcarbonyl, which C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, CN, NO$_2$, OH, C$_1$-C$_8$alkyl, C$_1$-C$_4$haloalkyl, C$_1$-C$_8$alkoxy, phenyl-C$_1$-C$_3$alkyloxy, phenoxy, C$_1$-C$_8$alkylsulfanyl, phenylsulfanyl, N(C$_1$-C$_8$alkyl)$_2$, diphenylamino, (CO)O(C$_1$-C$_8$alkyl), (CO)C$_1$-C$_8$alkyl or (CO)N(C$_1$-C$_8$)$_2$, phenyl or benzoyl;

or R$_{3a}$ is C$_1$-C$_{20}$alkanoyl or C$_3$-C$_{12}$alkenoyl, which C$_1$-C$_{20}$alkanoyl or C$_3$-C$_{12}$alkenoyl is unsubstituted or substituted by one or more halogen, phenyl, C$_1$-C$_8$alkylphenyl, C$_1$-C$_8$alkoxyphenyl, OH, C$_1$-C$_8$alkoxy, phenoxy, C$_1$-C$_8$alkylsulfanyl, phenylsulfanyl, N(C$_1$-C$_8$alkyl)$_2$ or diphenylamino;

R$_4$ is hydrogen, C$_1$-C$_{20}$alkyl which is unsubstituted or substituted by one or more substituents selected from the group consisting of halogen, OR$_{3a}$, SR$_{4a}$, NR$_{5a}$R$_{6a}$, CN, (CO)OR$_{3a}$, (CO)NR$_{5a}$R$_{6a}$, PO(OR$_{1a}$)$_2$, S(O)$_m$R$_{1a}$, C$_3$-C$_8$cycloalkyl which is uninterrupted or interrupted by one or more O, S, CO or NR$_{5a}$, C$_6$-C$_{20}$aryl, C$_3$-C$_{20}$heteroaryl, C$_6$-C$_{20}$aroyl and C$_3$-C$_{20}$heteroarylcarbonyl, which C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, phenyl, C$_1$-C$_{20}$alkylphenyl, C$_1$-C$_8$alkoxyphenyl, C$_1$-C$_4$haloalkyl, CN, NO$_2$, OR$_{3a}$, SR$_{4a}$, NR$_{5a}$R$_{6a}$, PO(OR$_{1a}$)$_2$ or S(O)$_m$R$_{1a}$;

or R$_4$ is C$_2$-C$_{20}$alkyl interrupted by one or more O, S, NR$_{5a}$, CO, SO or SO$_2$, which interrupted C$_2$-C$_{20}$alkyl is unsubstituted or substituted by one or more C$_3$-C$_8$cycloalkyl, OH, SH, O(CO)R$_{1a}$, (CO)OR$_{3a}$, (CO)NR$_{5a}$R$_{6a}$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, C$_1$-C$_8$alkyl, OR$_{3a}$, SR$_{4a}$ or NR$_{5a}$R$_{6a}$;

or R$_4$ is C$_2$-C$_{12}$alkenyl or C$_3$-C$_{20}$cycloalkyl, which C$_2$-C$_{12}$alkenyl or C$_3$-C$_{20}$cycloalkyl is uninterrupted or interrupted by one or more O, S, CO, NR$_{5a}$ or COOR$_{3a}$;

or R$_4$ is C$_6$-C$_{20}$aryl or C$_3$-C$_{20}$heteroaryl, which C$_6$-C$_{20}$aryl or C$_3$-C$_{20}$heteroaryl is unsubstituted or substituted by one or more substituents selected from the group consisting of halogen, CN, NO$_2$, OR$_{3a}$, SR$_{4a}$, NR$_{5a}$R$_{6a}$, COOR$_{3a}$, (CO)R$_{1a}$ (CO)NR$_{5a}$R$_{6a}$, PO(OR$_{1a}$)$_2$, S(O)$_m$R$_{1a}$,

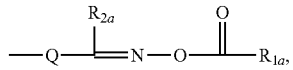

C$_1$-C$_{20}$alkyl which is unsubstituted or substituted by one or more halogen, COOR$_{3a}$, CONR$_{5a}$R$_{6a}$, phenyl, C$_3$-C$_8$cycloalkyl, C$_3$-C$_{20}$heteroaryl, OR$_{3a}$, SR$_{4a}$ or NR$_{5a}$R$_{6a}$, C$_2$-C$_{20}$alkyl which is interrupted by one or more O, S or NR$_{5a}$, phenyl, naphthyl, benzoyl and naphthoyl, which phenyl, naphthyl, benzoyl or naphthoyl is unsubstituted or substituted by OR$_{3a}$, SR$_{4a}$ or NR$_{5a}$R$_{6a}$;

or R$_4$ together with one of the carbon atoms of R$_2$ or M forms a 5- or 6-membered saturated or unsaturated ring which is uninterrupted or interrupted by O, S or NR$_{5a}$, and which 5- or 6-membered saturated or unsaturated ring is unsubstituted or substituted by one or more C$_1$-C$_{20}$alkyl, OR$_{3a}$, SR$_{4a}$, NR$_{5a}$R$_{6a}$, (CO)R$_{1a}$, NO$_2$, halogen, C$_1$-C$_4$-haloalkyl, CN, phenyl, C$_1$-C$_{20}$alkylphenyl, C$_1$-C$_8$alkoxyphenyl,

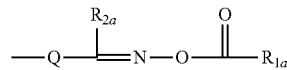

or C$_3$-C$_{20}$cyclalkyl which is uninterrupted or interrupted by one or more O, S, CO or NR$_{5a}$;

R$_{4a}$ is hydrogen, C$_1$-C$_{20}$alkyl which is unsubstituted or substituted by one or more substituents selected from the group consisting of halogen, OH, SH, CN, C$_3$-C$_8$alkenoxy, OCH$_2$CH$_2$CN, OCH$_2$CH$_2$(CO)O(C$_1$-C$_8$alkyl), O(CO)(C$_1$-C$_8$alkyl), O(CO)(C$_2$-C$_4$)alkenyl, O(CO)phenyl, (CO)OH, (CO)O(C$_1$-C$_8$alkyl), C$_3$-C$_8$cycloalkyl, SO$_2$(C$_1$-C$_4$haloalkyl), O(C$_1$-C$_4$haloalkyl), phenyl, $C_1$-$C_8$alkylphenyl, $C_1$-$C_8$alkoxyphenyl and $C_3$-$C_8$cycloalkyl which is interrupted by one or more O;

or $R_{4a}$ is $C_2$-$C_{20}$alkyl interrupted by one or more O, S, N($C_1$-$C_8$alkyl), CO, SO or $SO_2$, which interrupted $C_2$-$C_{20}$alkyl is unsubstituted or substituted by one or more $C_3$-$C_8$cycloalkyl, OH, SH, O(CO)($C_1$-$C_8$alkyl), (CO)O($C_1$-$C_8$alkyl), (CO)N($C_1$-$C_8$alkyl)$_2$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $C_1$-$C_8$alkoxy, $C_1$-$C_8$alkylsulfanyl or N($C_1$-$C_8$alkyl)$_2$;

or $R_{4a}$ is $C_2$-$C_{12}$alkenyl or $C_3$-$C_8$cycloalkyl, which $C_2$-$C_{12}$alkenyl or $C_3$-$C_8$cycloalkyl is uninterrupted or interrupted by one or more O, S, CO, N($C_1$-$C_8$alkyl) or COO ($C_1$-$C_8$alkyl);

or $R_{4a}$ is $C_6$-$C_{20}$aryl, $C_3$-$C_{20}$heteroaryl, $C_6$-$C_{20}$aroyl or $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, CN, $NO_2$, OH, $C_1$-$C_8$alkyl, $C_1$-$C_4$haloalkyl, $C_1$-$C_8$alkoxy, phenyl-$C_1$-$C_3$alkyloxy, phenoxy, $C_1$-$C_8$alkylsulfanyl, phenylsulfanyl, N($C_1$-$C_8$alkyl)$_2$, diphenylamino, (CO)O($C_1$-$C_8$alkyl), (CO)$C_1$-$C_8$alkyl, (CO)N($C_1$-$C_8$)$_2$, phenyl or benzoyl;

or $R_{4a}$ is $C_1$-$C_{20}$alkanoyl or $C_3$-$C_{12}$alkenoyl, which $C_1$-$C_{20}$alkanoyl or $C_3$-$C_{12}$alkenoyl is unsubstituted or substituted by one or more halogen, phenyl, $C_1$-$C_8$alkylphenyl, $C_1$-$C_8$alkoxyphenyl, OH, $C_1$-$C_8$alkoxy, phenoxy, $C_1$-$C_8$alkylsulfanyl, phenylsulfanyl, N($C_1$-$C_8$alkyl)$_2$ or diphenylamino;

$R_5$ and $R_6$ independently of each other are hydrogen, S(O)$_m$$R_{1a}$, O(CO)$R_{1a}$, (CO)$R_{1a}$ or CON$R_{5a}$$R_{6a}$;

or $R_5$ and $R_6$ independently of each other are $C_1$-$C_{20}$alkyl which is unsubstituted or substituted by one or more substituents selected from the group consisting of halogen, O$R_{3a}$, S$R_{4a}$, N$R_{5a}$$R_{6a}$, CN, (CO)O$R_{3a}$, (CO)N$R_{5a}$$R_{6a}$, PO(O$R_{1a}$)$_2$, S(O)$_m$$R_{1a}$, $C_3$-$C_8$cycloalkyl which is uninterrupted or interrupted by one or more O, S, CO or N$R_{5a}$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, O$R_{3a}$, S$R_{4a}$, N$R_{5a}$$R_{6a}$, PO(O$R_{1a}$)$_2$ or S(O)$_m$$R_{1a}$;

or $R_5$ and $R_6$ independently of each other are $C_2$-$C_{20}$alkyl interrupted by one or more O, S, N$R_{5a}$, CO, SO or $SO_2$, which interrupted $C_2$-$C_{20}$alkyl is unsubstituted or substituted by one or more $C_3$-$C_8$cycloalkyl, OH, SH, O(CO)$R_{1a}$, (CO)O$R_{3a}$, (CO)N$R_{5a}$$R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, O$R_{3a}$, S$R_{4a}$ or N$R_{5a}$$R_{6a}$;

or $R_5$ and $R_6$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, N$R_{5a}$ or COO$R_{3a}$;

or $R_5$ and $R_6$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, O$R_{3a}$, S$R_{4a}$, N$R_{5a}$$R_{6a}$, COO$R_{3a}$, (CO)$R_{1a}$ (CO)N$R_{5a}$$R_{6a}$, PO(O$R_{1a}$)$_2$, S(O)$_m$$R_{1a}$,

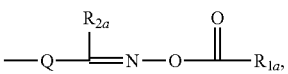

$C_1$-$C_{20}$alkyl which is unsubstituted or substituted by one or more halogen, COO$R_{3a}$, CON$R_{5a}$$R_{6a}$, phenyl, $C_3$-$C_8$cycloalkyl, $C_3$-$C_{20}$heteroaryl, O$R_{3a}$, S$R_{4a}$ or N$R_{5a}$$R_{6a}$, $C_2$-$C_{20}$alkyl which is interrupted by one or more O, S or N$R_{5a}$, phenyl, naphthyl, benzoyl and naphthoyl, which phenyl, naphthyl, benzoyl or naphthoyl is unsubstituted or substituted by O$R_{3a}$, S$R_{4a}$ or N$R_{5a}$$R_{6a}$;

or $R_5$ and $R_6$ independently of each other are $C_1$-$C_{20}$alkoxy, which is unsubstituted or substituted by one or more halogen, phenyl, $C_1$-$C_8$alkylphenyl or $C_1$-$C_8$alkoxyphenyl;

or $R_5$ and $R_6$ independently of each other are $C_2$-$C_{20}$alkoxy, which is interrupted by one or more O, S, N$R_{5a}$, CO, SO or $SO_2$;

or $R_5$ and $R_6$ independently of each other are $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_8$alkyl, $C_1$-$C_4$haloalkyl, phenyl, $C_1$-$C_8$alkylphenyl, $C_1$-$C_8$alkoxyphenyl, CN, $NO_2$, O$R_{3a}$, S$R_{4a}$, N$R_{5a}$$R_{6a}$, COO$R_{3a}$, (CO)$R_{1a}$ or $SO_2$$R_{1a}$;

or $R_5$ together with one of the carbon atoms of $R_2$ or M forms a 5- or 6-membered saturated or unsaturated ring which is uninterrupted or interrupted by O, S or N$R_{5a}$, and which 5- or 6-membered saturated or unsaturated ring is unsubstituted or substituted by one or more $C_1$-$C_{20}$alkyl, O$R_{3a}$, S$R_{4a}$, N$R_{5a}$$R_{6a}$, (CO)$R_{1a}$, $NO_2$, halogen, $C_1$-$C_4$-haloalkyl, CN, phenyl, $C_1$-$C_{20}$alkylphenyl, $C_1$-$C_8$alkoxyphenyl,

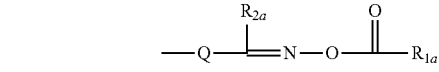

or $C_3$-$C_{20}$cyclalkyl which is uninterrupted or interrupted by one or more O, S, CO or N$R_{5a}$;

or $R_5$ and $R_6$ together with the N-atom to which they are attached form a 5- or 6-membered saturated or unsaturated ring which is uninterrupted or interrupted by O, S or N$R_{5a}$, and which 5- or 6-membered saturated or unsaturated ring is unsubstituted or substituted by one or more $C_1$-$C_{20}$alkyl, O$R_{3a}$, S$R_{4a}$, N$R_{5a}$$R_{6a}$, (CO)$R_{1a}$, $NO_2$, halogen, $C_1$-$C_4$-haloalkyl, CN, phenyl,

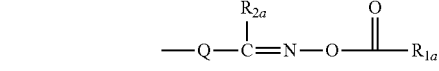

or $C_3$-$C_{20}$cyclalkyl which is uninterrupted or interrupted by one or more O, S, CO or N$R_{5a}$;

$R_{5a}$ and $R_{6a}$ independently of each other are hydrogen, $C_1$-$C_{20}$alkyl, S(O)$_m$($C_1$-$C_8$alkyl), O(CO)($C_1$-$C_8$alkyl), (CO)($C_1$-$C_8$alkyl), (CO)O($C_1$-$C_8$alkyl) or CON($C_1$-$C_8$alkyl)$_2$;

or $R_{5a}$ and $R_{6a}$ independently of each other are $C_1$-$C_{20}$alkyl substituted by one or more halogen, OH, SH, CN, $C_3$-$C_8$alkenoxy, OCH$_2$CH$_2$CN, OCH$_2$CH$_2$(CO)O($C_1$-$C_8$alkyl), O(CO)($C_1$-$C_8$alkyl), O(CO)($C_2$-$C_4$)alkenyl, O(CO)phenyl, (CO)OH, (CO)O($C_1$-$C_8$alkyl), $C_3$-$C_8$cycloalkyl, $SO_2$($C_1$-$C_4$haloalkyl), O($C_1$-$C_4$haloalkyl), phenyl, $C_1$-$C_8$alkylphenyl, $C_1$-$C_8$alkoxyphenyl, $C_3$-$C_8$cycloalkyl or $C_3$-$C_8$cycloalkyl which is interrupted by one or more O;

or $R_{5a}$ and $R_{6a}$ independently of each other are $C_2$-$C_{20}$alkyl interrupted by one or more O, S, N($C_1$-$C_8$alkyl), CO, SO or $SO_2$, which interrupted $C_2$-$C_{20}$alkyl is unsubstituted or substituted by $C_3$-$C_8$cycloalkyl, OH, SH, O(CO)($C_1$-$C_8$alkyl), (CO)O($C_1$-$C_8$alkyl), (CO)N($C_1$-$C_8$alkyl)$_2$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $C_1$-$C_8$alkoxy, $C_1$-$C_8$alkylsulfanyl or N($C_1$-$C_8$alkyl)$_2$;

or $R_{5a}$ and $R_{6a}$ independently of each other are $C_2$-$C_{12}$alkenyl or $C_3$-$C_8$cycloalkyl, which $C_2$-$C_{12}$alkenyl or $C_3$-$C_8$cycloalkyl is uninterrupted or interrupted by one or more O, S, CO, N($C_1$-$C_8$alkyl) or COO($C_1$-$C_8$alkyl);

or $R_{5a}$ and $R_{6a}$ independently of each other are $C_6$-$C_{20}$aryl, $C_3$-$C_{20}$heteroaryl, $C_6$-$C_{20}$aroyl or $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, CN, $NO_2$, OH, $C_1$-$C_8$alkyl, $C_1$-$C_4$haloalkyl, $C_1$-$C_8$alkoxy, phenyl-$C_1$-$C_3$alkyloxy, phenoxy, $C_1$-$C_8$alkylsulfanyl, phenylsulfanyl, N($C_1$-$C_8$alkyl)$_2$, diphenylamino, (CO)O($C_1$-$C_8$alkyl), (CO)$C_1$-$C_8$alkyl, (CO)N($C_1$-$C_8$alkyl)$_2$, phenyl or benzoyl;

or $R_{5a}$ and $R_{6a}$ independently of each other are $C_1$-$C_{20}$alkanoyl or $C_3$-$C_{12}$alkenoyl, which $C_1$-$C_{20}$alkanoyl or $C_3$-$C_{12}$alkenoyl is unsubstituted or substituted by one or more halogen, phenyl, $C_1$-$C_8$alkylphenyl, $C_1$-$C_8$alkoxyphenyl, OH, $C_1$-$C_8$alkoxy, phenoxy, $C_1$-$C_8$alkylsulfanyl, phenylsulfanyl, N($C_1$-$C_8$alkyl)$_2$ or diphenylamino;

or $R_{5a}$ and $R_{6a}$ independently of each other are $C_1$-$C_{20}$alkoxy, which is unsubstituted or substituted by one or more halogen, phenyl, $C_1$-$C_8$alkylphenyl or $C_1$-$C_8$alkoxyphenyl;

or $R_{5a}$ and $R_{6a}$ independently of each other are $C_2$-$C_{20}$alkoxy, which is interrupted by one or more O, S, N($C_1$-$C_8$alkyl), CO, SO or $SO_2$;

or $R_{5a}$ and $R_{6a}$ independently of each other are $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_8$alkyl, $C_1$-$C_4$haloalkyl, phenyl, $C_1$-$C_8$alkylphenyl, $C_1$-$C_8$alkoxyphenyl, CN, $NO_2$, $C_1$-$C_8$alkoxy, $C_1$-$C_8$alkylsulfanyl, N($C_1$-$C_8$alkyl)$_2$, CO(O$C_1$-$C_8$alkyl), (CO)($C_1$-$C_8$alkyl) or $SO_2$—($C_1$-$C_8$alkyl);

or $R_{5a}$ and $R_{6a}$ together with the N-atom to which they are attached form a 5- or 6-membered saturated or unsaturated ring which is uninterrupted or interrupted by O, S or N($C_1$-$C_8$alkyl), and which 5- or 6-membered saturated or unsaturated ring is unsubstituted or substituted by one or more $C_1$-$C_8$alkyl, $C_1$-$C_8$alkoxy, $C_1$-$C_8$alkylsulfanyl, N($C_1$-$C_8$alkyl)$_2$, $NO_2$, halogen, $C_1$-$C_4$haloalkyl, CN, phenyl or $C_3$-$C_{20}$cyclalkyl which is uninterrupted or interrupted by one or more O, S, CO or N($C_1$-$C_8$alkyl);

$R_7$, $R_8$, $R_9$, $R_{10}$ and $R_{11}$ independently of each other are hydrogen, $C_1$-$C_{20}$alkyl, halogen, CN, $NO_2$, $OR_3$, $SR_4$, $NR_5R_6$, $COOR_3$, $(CO)R_{1a}$, $(CO)NR_5R_6$, $PO(OR_{1a})_2$, $S(O)_mR_{1a}$,

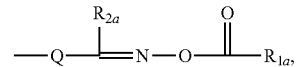

wherein the substituents $OR_3$, $SR_4$ or $NR_5R_6$ optionally form 5- or 6-membered ring via the radicals $R_3$, $R_4$, $R_5$ or $R_6$ with further substituents on the group X;

or $R_7$, $R_8$, $R_9$, $R_{10}$ and $R_{11}$ independently of each other are $C_1$-$C_{20}$alkyl substituted by one or more substituents selected from the group consisting of halogen, $OR_3$, $SR_4$, $NR_5R_6$, CN, $(CO)OR_3$, $(CO)NR_5R_6$, $PO(OR_{1a})_2$, $S(O)_mR_{1a}$, $C_3$-$C_8$cycloalkyl which is uninterrupted or interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$, $NR_5R_6$, $PO(OR_{1a})_2$ or $S(O)_mR_{1a}$;

or $R_7$, $R_8$, $R_9$, $R_{10}$ and $R_{11}$ independently of each other are $C_2$-$C_{20}$alkyl interrupted by one or more O, S, $NR_5$, CO, SO or $SO_2$, which interrupted $C_2$-$C_{20}$alkyl is unsubstituted or substituted by $C_3$-$C_8$cycloalkyl, OH, SH, O(CO)$R_{1a}$, (CO)$OR_3$, (CO)$NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or $R_7$, $R_8$, $R_9$, $R_{10}$ and $R_{11}$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$;

or $R_7$, $R_8$, $R_9$, $R_{10}$ and $R_{11}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_3$, $SR_4$, $NR_5R_6$, $COOR_3$, $(CO)R_{1a}$ $(CO)NR_5R_6$, $PO(OR_{1a})_2$, $S(O)_mR_{1a}$,

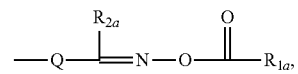

$C_1$-$C_{20}$alkyl which is unsubstituted or substituted by one or more halogen, $COOR_{3a}$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{20}$alkyl which is interrupted by one or more O, S or $NR_5$, phenyl, naphthyl, benzoyl and naphthoyl, which phenyl, naphthyl, benzoyl or naphthoyl is unsubstituted or substituted by $OR_3$, $SR_4$ or $NR_5R_6$;

or $R_8$ and $R_9$, $R_9$ and $R_{10}$, or $R_{10}$ and $R_{11}$ are

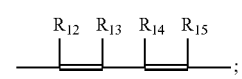

$R_{12}$, $R_{13}$, $R_{14}$ and $R_{15}$ independently of each other are hydrogen, $C_1$-$C_{20}$alkyl, halogen, CN, $NO_2$, $OR_3$, $SR_4$, $NR_5R_6$, $COOR_3$, $(CO)R_{1a}$, $(CO)NR_5R_6$, $PO(OR_{1a})_2$, $S(O)_mR_{1a}$,

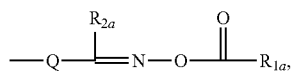

wherein the substituents $OR_3$, $SR_4$ or $NR_5R_6$ optionally form a 5- or 6-membered ring via the radicals $R_3$, $R_4$, $R_5$ or $R_6$ with further substituents on the group X;

or $R_{12}$, $R_{13}$, $R_{14}$ and $R_{15}$ independently of each other are $C_1$-$C_{20}$alkyl substituted by one or more substituents selected from the group consisting of halogen, $OR_3$, $SR_4$, $NR_5R_6$, CN, $(CO)OR_3$, $(CO)NR_5R_6$, $PO(OR_{1a})_2$, $S(O)_mR_{1a}$, $C_3$-$C_8$cycloalkyl which is uninterrupted or interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$, $NR_5R_6$, $PO(OR_{1a})_2$ or $S(O)_mR_{1a}$;

or $R_{12}$, $R_{13}$, $R_{14}$ and $R_{15}$ independently of each other are $C_2$-$C_{20}$alkyl interrupted by one or more O, S, $NR_5$, CO, SO or $SO_2$, which interrupted $C_2$-$C_{20}$alkyl is unsubstituted or substituted by $C_3$-$C_8$cycloalkyl, OH, SH, $O(CO)R_{1a}$, (CO)$OR_3$, $(CO)NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or $R_{12}$, $R_{13}$, $R_{14}$ and $R_{15}$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$;

or $R_{12}$, $R_{13}$, $R_{14}$ and $R_{15}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_3$, $SR_4$, $NR_5R_6$, $COOR_3$, $(CO)R_{1a}$ $(CO)NR_5R_6$, $PO(OR_{1a})_2$, $S(O)_m$—$R_{1a}$,

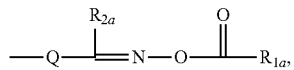

$C_1$-$C_{20}$alkyl which is unsubstituted or substituted by one or more halogen, $COOR_{3a}$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{20}$alkyl which is interrupted by one or more O, S or $NR_5$, phenyl, naphthyl, benzoyl and naphthoyl, which phenyl, naphthyl, benzoyl or naphthoyl is unsubstituted or substituted by $OR_3$, $SR_4$ or $NR_5R_6$;

$R_{16}$ and $R_{17}$ independently of each other are hydrogen, $C_1$-$C_{20}$alkyl, which is unsubstituted or substituted by one or more substituents selected from the group consisting of halogen, $OR_3$, $SR_4$, $NR_5R_6$, CN, $(CO)OR_3$, $(CO)NR_5R_6$, $C_3$-$C_8$cycloalkyl which is uninterrupted or interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$ or $NR_5R_6$;

or $R_{16}$ and $R_{17}$ independently of each other are $C_2$-$C_{20}$alkyl interrupted by one or more O, S, $NR_5$, CO, SO or $SO_2$, which interrupted $C_2$-$C_{20}$alkyl is unsubstituted or substituted by $C_3$-$C_8$cycloalkyl, OH, SH, $O(CO)R_{1a}$, (CO)$OR_3$, $(CO)NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or $R_{16}$ and $R_{17}$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$;

or $R_{16}$ and $R_{17}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_3$, $SR_4$, $NR_5R_6$, $COOR_3$, $(CO)R_{1a}$ or $SO_2R_{1a}$;

or $R_{16}$ and $R_{17}$ together with the carbon atom to which they are attached form a 5- or 6-membered saturated or unsaturated ring which is uninterrupted or interrupted by O, S or $NR_{5a}$, and which 5- or 6-membered saturated or unsaturated ring is unsubstituted or substituted by one or more $C_1$-$C_{20}$alkyl, $OR_{3a}$, $SR_{4a}$, $NR_{5a}R_{6a}$, $(CO)R_{1a}$, $NO_2$, halogen, $C_1$-$C_4$haloalkyl, CN, phenyl or $C_3$-$C_{20}$cyclalkyl which is uninterrupted or interrupted by one or more O, S, CO or $NR_{5a}$;

$Ar_1$ is $C_6$-$C_{20}$aryl, $C_3$-$C_{20}$heteroaryl, $C_6$-$C_{20}$aroyl, $C_3$-$C_{20}$heteroarylcarbonyl or

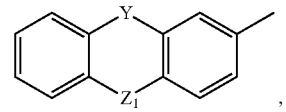

which $C_6$-$C_{20}$aryl, $C_3$-$C_{20}$heteroaryl, $C_6$-$C_{20}$aroyl, $C_3$-$C_{20}$heteroarylcarbonyl or

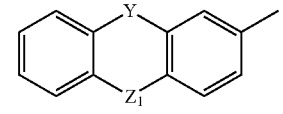

is unsubstituted or substituted by one or more substituents selected from the group consisting of halogen, CN, $NO_2$, $COOR_3$, $(CO)R_{1a}$, $(CO)NR_5R_6$, $PO(OR_{1a})_2$, $S(O)_mR_{1a}$,

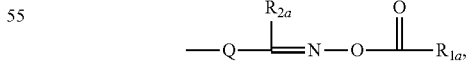

$OR_3$, $SR_4$, $NR_5R_6$, wherein the substituents $OR_3$, $SR_4$ or $NR_5R_6$ optionally form 5- or 6-membered rings via the radicals $R_3$, $R_4$, $R_5$ or $R_6$ with further substituents on the phenyl ring, $C_1$-$C_{20}$alkyl which is unsubstituted or substituted by one or more halogen, $COOR_3$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{20}$alkyl which is interrupted by one or more O, S or $NR_5$, $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$, phenyl, naphthyl, benzoyl and naphthoyl, which phenyl, naphthyl, benzoyl or naphthoyl is unsubstituted or substituted by $OR_3$, $SR_4$ or $NR_5R_6$;

or $Ar_1$ is

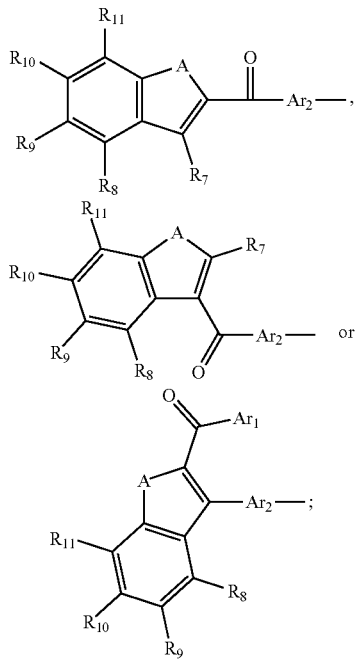

$Ar_2$ is phenylene, naphthylene, phenylenecarbonyl, naphthylenecarbonyl,

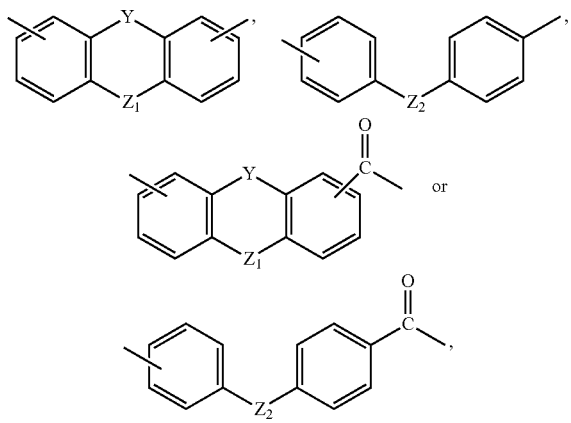

which phenylene, naphthylene, phenylenecarbonyl, naphthylenecarbonyl,

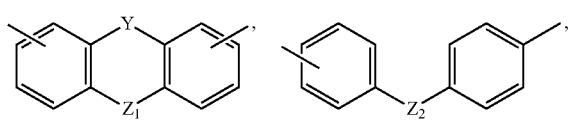

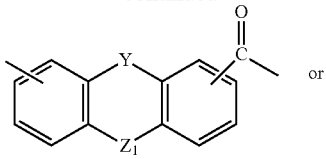

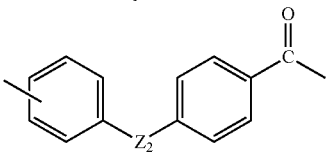

is unsubstituted or substituted by one or more substituents selected from the group consisting of halogen, CN, $NO_2$, $COOR_3$, $(CO)R_{1a}$, $(CO)NR_5R_6$, $PO(OR_{1a})_2$, $S(O)_mR_{1a}$, $$-Q-\overset{R_{2a}}{\underset{}{=}}N-O-\overset{O}{\underset{}{\|}}-R_{1a},$$

$OR_3$, $SR_4$, $NR_5R_6$, $C_1$-$C_{20}$alkyl which is unsubstituted or substituted by one or more halogen, $COOR_3$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$, $C_2$-$C_{20}$alkyl which is interrupted by one or more O, S or $NR_5$, phenyl, naphthyl, benzoyl and naphthoyl, which phenyl, naphthyl, benzoyl or naphthoyl is unsubstituted or substituted by $OR_3$, $SR_4$ or $NR_5R_6$;

M is $C_1$-$C_{20}$alkylene which is unsubstituted or substituted by one or more substituents selected from the group consisting of halogen, $OR_3$, $SR_4$, $NR_5R_6$, CN, $(CO)OR_3$, $(CO)NR_5R_6$, $C_3$-$C_8$cycloalkyl which is uninterrupted or interrupted by one or more O, S, CO or $NR_5$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$ or $NR_5R_6$;

or M is $C_2$-$C_{20}$alkylene interrupted by one or more O, S, $NR_5$, CO, SO or $SO_2$, which $C_1$-$C_{20}$alkylene or $C_2$-$C_{20}$alkylene is unsubstituted or substituted by one or more substituents selected from the group consisting of $C_3$-$C_8$cycloalkyl, OH, SH, $O(CO)R_{1a}$, $(CO)OR_3$, $(CO)NR_5R_6$, $C_6$-$C_{20}$aryl, $C_3$-$C_{20}$heteroaryl, $C_6$-$C_{20}$aroyl and $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

or M is $C_2$-$C_{12}$alkenylene or $C_3$-$C_{20}$cycloalkylene, which $C_2$-$C_{12}$alkenylene or $C_3$-$C_{20}$cycloalkylene is uninterrupted or interrupted by one or more O, S, CO, $NR_5$ or $COOR_3$;

or M is $C_6$-$C_{20}$arylene or $C_3$-$C_{20}$heteroarylene, which $C_6$-$C_{20}$arylene or $C_3$-$C_{20}$heteroarylene is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_3$, $SR_4$, $NR_5R_6$, $COOR_3$, $(CO)R_{1a}$ or $SO_2R_{1a}$;

Y is a direct bond, O, S, $NR_5$ or CO;
$Z_1$ is O, S, CO or $CR_{16}(R_{17})$;
$Z_2$ is a direct bond, O, S or $NR_5$;
m is 1 or 2; and
Q is CO or a direct bond, fullfill the above requirements.

The compounds are α-ketoxime ester photopolymerisation initiators containing

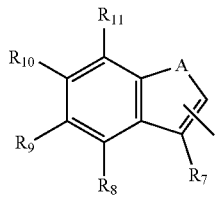

groups, wherein A, $R_7$, $R_8$, $R_9$, $R_{10}$ and $R_{11}$ are as defined above.

$C_1$-$C_{20}$alkyl is linear or branched and is, for example, $C_1$-$C_{18}$-, $C_1$-$C_{14}$, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_4$haloalkyl is $C_1$-$C_4$alkyl which is mono- or polysubstituted by halogen up to the exchange of all H-atoms by halogen. Examples are chloromethyl, trichloromethyl, trifluoromethyl or 2-bromopropyl, especially trifluoromethyl or trichloromethyl.

$C_2$-$C_{20}$alkyl interrupted by one or more O, S, $NR_5$, CO, SO or $SO_2$ is for example interrupted 1-9, 1-7 or once or twice by the defined radicals. In case the groups are interrupted by more than one O, said O-atoms are separated from one another by at least one methylene group, i.e. the O-atoms are non-consecutive. The alkyl groups in the interrupted alkyl are linear or branched. Examples are the following structural units —$CH_2$—O—$CH_3$, —$CH_2CH_2$—O—$CH_2CH_3$, —[$CH_2CH_2O$]$_y$—$CH_3$, with y=1-9, —($CH_2CH_2O$)$_7$—$CH_2CH_3$, —$CH_2$—$CH(CH_3)$—O—$CH_2$—$CH_2CH_3$, or —$CH_2$—$CH(CH_3)$—O—$CH_2CH_3$, etc.

$C_3$-$C_{20}$cycloalkyl or $C_3$-$C_8$cycloalkyl is a mono- or polycyclic aliphatic ring, for example a mono-, bi- or tricyclic aliphatic ring, e.g. $C_3$-$C_{18}$-, $C_3$-$C_{12}$-, $C_3$-$C_{10}$cycloalkyl. Examples of monocyclic rings are cyclopropyl, cyclobutyl, cyclopentyl, cyclohexyl, or cycloheptyl, especially cyclopentyl and cyclohexyl. Examples of polycyclic rings are perhydroanthracyl, perhydrophenyathryl, perhydronaphthyl, perhydrofluorenyl, perhydrochrysenyl, perhydropicenyl, adamantyl, bicyclo[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl,

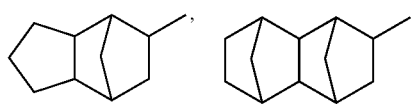

and the like.

Also "spiro"-cycloalkyl compounds are covered by the definition $C_3$-$C_{20}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, page 11 and 12, wherein to the formulae (1)-(46) a bond to achieve the "yl" has to be added. The person skilled in the art is aware of this fact.

$C_3$-$C_8$cycloalkyl which is interrupted by one or more O, S, CO or $NR_5$ refers to $C_3$-$C_8$cycloalkyl as defined above, wherein at least one C-atom is replaced by O, S, CO or $NR_5$.

$C_2$-$C_{12}$alkenyl is mono or polyunsaturated, linear or branched and is for example $C_2$-$C_8$-, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_1$-$C_{20}$alkoxy is linear or branched and is for example $C_1$-$C_{18}$-, $C_1$-$C_{16}$-, $C_1$-$C_{12}$-, $C_1$-$C_8$-, $C_1$-$C_6$- or $C_1$-$C_4$-alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpetyloxy, 2-ethylhexyloxy, octyloxy, nonyloxy, decyloxy, dodecyloxy, hexadecyloxy, octadecyloxy or icosyloxy, in particular methoxy, ethoxy, propoxy, isopropoxy, n-butyloxy, sec-butyloxy, iso-butyloxy, tert-butyloxy, especially methoxy.

$C_2$-$C_{20}$alkoxy, which is interrupted by one or more O, S, $NR_5$, CO, SO or $SO_2$ is for example interrupted 1-9, 1-7, 1-4 or once or twice by the defined radicals. In case the groups are interrupted by more than one O, said O-atoms are separated from one another by at least one methylene group, i.e. the O-atoms are non-consecutive. Examples are the following structural units —O—$CH_2$—O—$CH_3$, —O—$CH_2CH_2$—O—$CH_2CH_3$, —O—[$CH_2CH_2O$]$_v$$CH_3$, with v=1-4, —O—($CH_2CH_2O$)$_4CH_2CH_3$, —O—$CH_2$—CH($CH_3$)—O—$CH_2$—$CH_2CH_3$, or —O—$CH_2$—$CH(CH_3)$—O—$CH_2CH_3$, etc.

$C_1$-$C_8$alkylsulfanyl (=$C_1$-$C_8$alkylthio) is $C_1$-$C_8$alkyl (as defined above), which at the "yl" moiety bears one-S-atom. $C_1$-$C_8$alkylsulfanyl is linear or branched, for example, methylsulfanyl, ethylsulfanyl, propylsulfanyl, isopropylsulfanyl, n-butylsulfanyl, secbutylsulfanyl, isobutylsulfanyl, tert-butylsulfanyl, etc.

$C_1$-$C_{20}$alkanoyl (=$C_1$-$C_{20}$alkylcarbonyl) is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkanoyl or $C_4$-$C_{12}$- or $C_4$-$C_8$alkanoyl. Examples are formyl, acetyl, propionyl, butanoyl, isobutanoyl, pentanoyl, hexanoyl, heptanoyl, octanoyl, nonanoyl, decanoyl, dodecanoyl, tetradecanoyl, pentadecanoyl, hexadecanoyl, octadecanoyl, icosanoyl, preferably acetyl.

$C_3$-$C_{12}$alkenoyl is mono or polyunsaturated. Examples are propenoyl, 2-methylpropenoyl, butenoyl, pentenoyl, 1,3-pentadienoyl, 5-hexenoyl, etc.

Halogen is fluorine, chlorine, bromine and iodine, especially fluorine, chlorine and bromine, preferably fluorine and chlorine.

$C_1$-$C_{20}$alkylphenyl corresponds to phenyl that is substituted once or more times by alkyl at the phenyl ring and is for example $C_1$-$C_{12}$alkyl-, $C_1$-$C_8$alkyl- or $C_1$-$C_4$alkylphenyl, wherein the number of the alkyl corresponds to the total number of all C-atoms in all alkyl-substituents at the phenyl ring. Examples are tolyl, xylyl, mesityl, ethylphenyl, diethylphenyl, in particular tolyl and mesityl.

$C_1$-$C_8$alkoxyphenyl corresponds to phenyl that is substituted once or more times by alkoxyl at the phenyl ring and is for example $C_1$-$C_4$alkoxyphenyl, wherein the number of the alkoxy corresponds to the total number of all C-atoms in all alkoxy-substituents at the phenyl ring. Examples are methoxyphenyl, dimethoxyphenyl, trimethoxyphenyl, ethoxyphenyl, diethoxyphenyl, etc.

$C_6$-$C_{20}$aryl is for example phenyl, naphthyl, anthryl or phenanthryl, in particular phenyl or naphthyl, preferably phenyl.

Naphthyl corresponds to 1-naphthyl and 2-naphthyl.

$C_6$-$C_{20}$aroyl corresponds to $C_6$-$C_{20}$aryl-CO—, wherein $C_6$-$C_{20}$aryl is defined as above. Examples are benzoyl, naphthoyl etc.

$C_6$-$C_{20}$aryloxy corresponds to $C_6$-$C_{20}$aryl-O—, wherein $C_6$-$C_{20}$aryl is defined as above. Examples are phenyoxy, naphthyloxy etc.

Phenyl-$C_1$-$C_3$alkyloxy corresponds to $C_1$-$C_3$alkyloxy (=$C_1$-$C_3$alkoxy) which is substituted by phenyl.

$C_3$-$C_{20}$heteroaryl is meant to comprise either a one ring or a multiple ring system, e.g. a fused ring-system. Examples are thienyl, benzo[b]thienyl, naphtho[2,3-b]thienyl, thianthrenyl, furyl, dibenzofuryl, benzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 1H-tetrazol-5-yl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl, 10-methyl-2-phenoxazinyl, etc.

$C_3$-$C_{20}$heteroaryl in particular is thienyl, benzo[b]thienyl, furyl, benzofuryl, thianthrenyl, thioxanthyl, 1-methyl-2-indolyl or 1-methyl-3-indolyl.

$C_3$-$C_{20}$heteroarylcarbonyl corresponds to $C_3$-$C_{20}$heteroaryl-CO—, wherein $C_3$-$C_{20}$heteroaryl is defined as above.

$C_3$-$C_{20}$heteroaryloxy corresponds to $C_3$-$C_{20}$heteroaryl-O—, wherein $C_3$-$C_{20}$heteroaryl is defined as above.

$C_1$-$C_{20}$alkylene is linear or branched and is for example, $C_1$-$C_{18}$-, $C_1$-$C_{14}$-, $C_1$-$C_{12}$-, $C_1$-$C_8$-, $C_1$-$C_6$- or $C_1$-$C_4$alkylene. Examples are methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene or octadecylene.

$C_2$-$C_{20}$alkylene interrupted by one or more O, S, $NR_5$, CO, SO or $SO_2$ is, for example, interrupted 1-9 times, for example 1-7 times or once or twice by the defined substituents and the $C_2$-$C_{20}$alkylene is linear or branched. This produces structural units such as, for example, —$CH_2$—O—$CH_2$—, —$CH_2$—S—$CH_2$—, —$CH_2$—N($CH_3$)—$CH_2$—, —$CH_2CH_2$—O—$CH_2CH_2$—, —[$CH_2CH_2O$]$_y$—, —[$CH_2CH_2O$]$_y$—$CH_2$—, where y=1-9, —($CH_2CH_2O$)$_7CH_2CH_2$—, —$CH_2$—CH($CH_3$)—O—$CH_2$—CH($CH_3$)— or —$CH_2$—CH($CH_3$)—O—$CH_2$—$CH_2CH_2$—. Interrupting O-atoms are nonsuccessive.

$C_2$-$C_{12}$alkenylene is mono- or polyunsaturated, linear or branched and is, for example, $C_1$-$C_8$-, $C_1$-$C_6$- or $C_1$-$C_4$alkenylene. Examples are ethenylene, 1-propenylene, 1-butenylene, 3-butenylene, 2-butenylene, 1,3-pentadienylene, 5-hexenylene, 7-octenylene, etc.

$C_3$-$C_{20}$cycloalkylene consists of a two valent mono- or polycyclic aliphatic ring, for example a mono-, bi- or tricyclic aliphatic ring, e.g. $C_3$-$C_{18}$-, $C_3$-$C_{12}$-, $C_3$-$C_{10}$cycloalkylene. Examples are cyclopropylene, cyclopentylene, cyclohexylene, cyclooctylene, cyclododecylene,

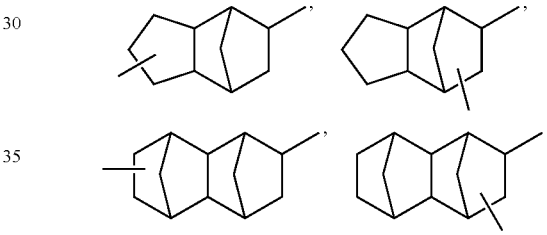

especially cyclopentylene and cyclohexylene, preferably cyclohexylene.

$C_6$-$C_{20}$arylene is for example phenylene, biphenylene, o-, m- and p-terphenylene, triphenylphenylene, naphthylene, binaphthylene, anthracenylene, phenanthrylene or pyrenylene, in particular phenylene or naphthylene, especially phenylene.

$C_3$-$C_{20}$heteroarylene refers to $C_3$-$C_{20}$heteroaryl as defined above however instead of being one-valent $C_3$-$C_{20}$heteroarylene groups are two valent.

If $R_5$ and $R_6$ together with the N-atom to which they are attached form a 5- or 6-membered saturated or unsaturated ring which is uninterrupted or interrupted by O, S or $NR_{5a}$, saturated or unsaturated rings are formed, for example aziridine, pyrrole, thiazole, pyrrolidine, oxazole, pyridine, 1,3-diazine, 1,2-diazine, piperidine or morpholine. Preferably, if $R_5$ and $R_6$ together with the N-atom to which they are attached form a 5- or 6-membered saturated or unsaturated ring which optionally is interrupted by O, S or $NR_{5a}$, 5- or 6-membered saturated rings which are not interrupted or which are interrupted by O or $NR_{5a}$, in particular by O, are formed.

If $R_{5a}$ and $R_{6a}$ together with the N-atom to which they are attached form a 5- or 6-membered saturated or unsaturated ring which is uninterrupted or interrupted by O, S or N($C_1$-$C_8$alkyl), saturated or unsaturated rings are formed as described above for $R_5$ and $R_6$ forming a ring with the N-atom.

If $R_{16}$ and $R_{17}$ together with the carbon atom to which they are attached form a 5- or 6-membered saturated or unsaturated ring which is uninterrupted or interrupted by O, S or $NR_{5a}$, saturated or unsaturated rings are formed, for example, pyrrole, thiazole, pyrrolidine, oxazole, pyridine, piperidine or morpholine. Preferably, if $R_{16}$ and $R_{17}$ together with the carbon to which they are attached form a 5- or 6-membered saturated or unsaturated ring which optionally is interrupted by O, S or $NR_{5a}$, 5- or 6-membered saturated rings which are not interrupted or which are interrupted by O or $NR_{5a}$, in particular by O, are formed.

If $Ar_1$ as $C_6$-$C_{20}$aryl, $C_3$-$C_{20}$heteroaryl, $C_6$-$C_{20}$aroyl, $C_3$-$C_{20}$heteroarylcarbonyl or

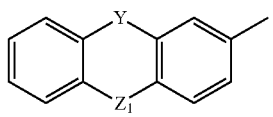

is substituted by one or more substituents selected from the group consisting of $OR_3$, $SR_4$, $NR_5R_6$, and wherein the substituents $OR_3$, $SR_4$ or $NR_5R_6$ form 5- or 6-membered rings via the radicals $R_3$, $R_4$, $R_5$ or $R_6$ with further substituents on the phenyl ring, for example structures like

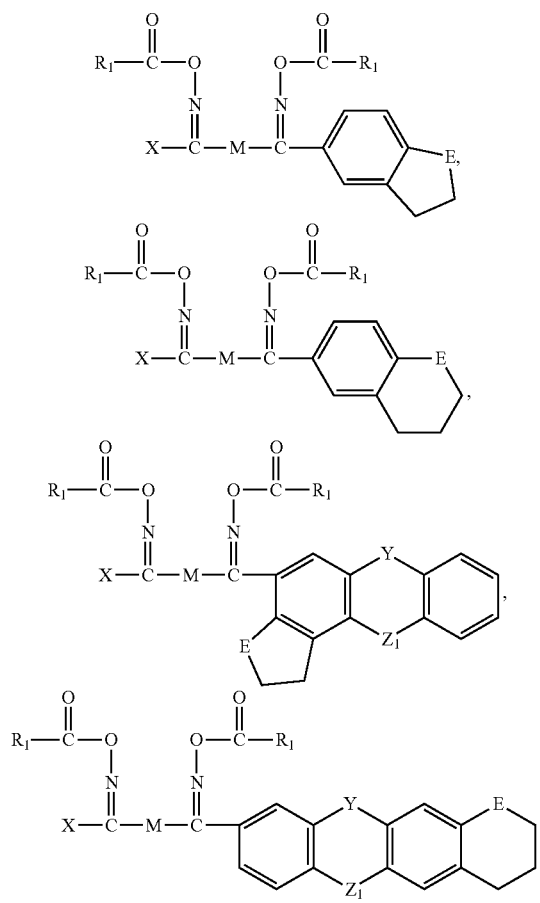

etc. are formed, wherein E is O, S or $NR_5$ (and $R_1$, X, M, Y and $Z_1$ are as defined above).

Substituted aryl radicals phenyl, naphthyl, $C_6$-$C_{20}$aryl, $C_5$-$C_{20}$heteroaryl, $C_6$-$C_{20}$arylene or $C_3$-$C_{20}$heteroarylene etc. are substituted 1 to 7, 1 to 6 or 1 to 4 times respectively, in particular one, two or three times. It is evident that a defined aryl or heteroaryl radical cannot have more substituents than free "CH" or "NH" positions are at the defined ring. Substituents on the phenyl ring are preferably in positions 4 or in 3,4-, 3,4,5-, 2,6-, 2,4- or 2,4,6-configuration on the phenyl ring.

Interrupted radicals which are interrupted once or more times are for example interrupted 1-19, 1-15, 1-12, 1-9, 1-7, 1-5, 1-4, 1-3 or once or twice (it is evident, that the number of interrupting atoms depends on the number of C-atoms to be interrupted).

Substituted radicals, which are substituted once or more times have for example 1-7, 1-5, 1-4, 1-3 or one or two identical or different substituents.

A radical substituted by one or more defined substituents is meant to have either one substituent or more substituents of identical or different definitions as given The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

Oxime esters of formula I and II are prepared by methods described in the literature, for example by reaction of the corresponding oximes with an acyl halide, in particular a chloride, or an anhydride in an inert solvent such as for example t-butyl methyl ether, tetra-hydrofurane (THF), dimethoxyethane, dimethylacetamide (DMA) or dimethylformamide in the presence of a base or a mixture of bases, for example triethylamine or pyridine, or in a basic solvent such as pyridine. As example in the following the preparation of compounds of the formula I is described:

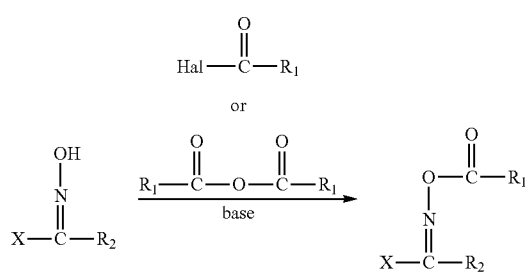
(I)

The compounds of formula II can be obtained analogously by using the appropriate oximes as starting materials:

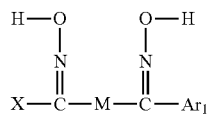

X, Ar$_1$, M, R$_1$ and R$_2$ have the meanings as given above. Hal means a halogen atom, in particular Cl. R$_1$ preferably is methyl.

Such reactions are well known to those skilled in the art, and are generally carried out at temperatures of −15 to +50° C., preferably 0 to 25° C.

Every oxime ester group can exist in two configurations, (Z) or (E). And the invention covers both, the E and the Z configuration. It is possible to separate the isomers by conventional methods, but it is also possible to use the isomeric mixture as such as photoinitiating species. Therefore, the invention also relates to mixtures of configurational isomers of compounds of the formulae I and II.

The oximes required as starting materials can be obtained by a variety of methods described in standard chemistry textbooks (for instance in J. March, Advanced Organic Chemistry, 4th Edition, Wiley Interscience, 1992), or in specialized monographs, for example, S. R. Sandler & W. Karo, Organic functional group preparations, Vol. 3, Academic Press.

One of the most convenient methods is, for example, the reaction of aldehydes or ketones with hydroxylamine or its salt in polar solvents like DMA, aqueous DMA, ethanol or aqueous ethanol. In that case, a base such as sodium acetate or pyridine is added to control the pH of the reaction mixture. It is well known that the rate of the reaction is pH-dependent, and the base can be added at the beginning or continuously during the reaction. Basic solvents such as pyridine can also be used as base and/or solvent or cosolvent. The reaction temperature is generally from room temperature to the refluxing temperature of the mixture, usually about 20-120° C.

The corresponding ketone intermediates are for example prepared by the methods described in the literature, for example in standard chemistry textbooks (for instance in J. March, Advanced Organic Chemistry, 4th Edition, Wiley Interscience, 1992). In addition, successive Friedel-Crafts reaction is effective for synthesis of the intermediates. Such reactions are well known to those skilled in the art.

Another convenient synthesis of oximes is the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis coll. vol V, pp 32 and 373, coll. vol. III, pp 191 and 513, coll. vol. II, pp. 202, 204 and 363, are suitable for the preparation of the oximes used as starting materials in the invention. Nitrous acid is usually generated from sodium nitrite. The alkyl nitrite can be for example methyl nitrite, ethyl nitrite, isopropyl nitrite, butyl nitrite, or isoamyl nitrite.

The benzocyclic moiety of X in the corresponding ketone intermediates can be prepared by a variety of methods described in the standard literature. One of the most convenient method is, for example as described in Science of Synthesis, 10 (2000), p. 25, the condensation reaction of haloacetylaryl compound with o-hydroxybenzoyl compound (A=O) under basic conditions in polar solvent like acetone, dimethylformamide, acetonitrile or dioxane.

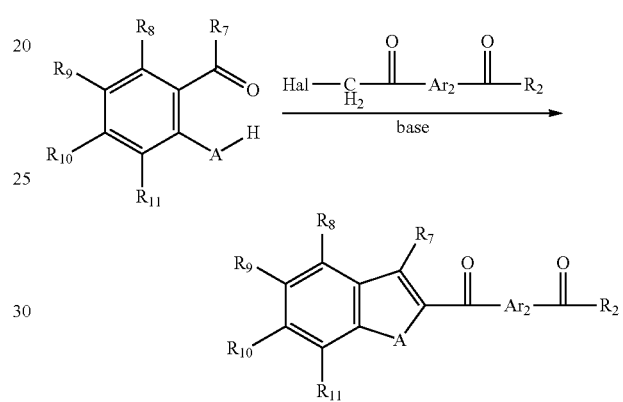

Subject of the invention also is a process for the preparation of a compound of the formula I or II as defined above by reacting the corresponding oxime compound of the formula (1A) or (IIA)

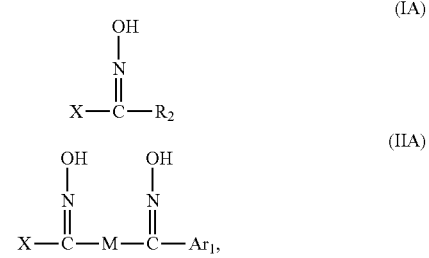

wherein X, Ar$_1$, M and R$_2$ are as defined above,
with an acyl halide of the formula III or an anhydride of the formula IV

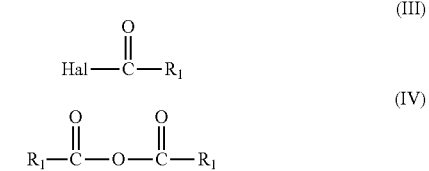

wherein Hal is a halogen, in particular Cl, and R$_{14}$ is as defined above, in the presence of a base or a mixture of bases; and the compounds of the Formula IA and IIA

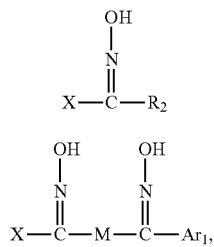   (IA)

   (IIA)

wherein
X, M, Ar$_1$ and R$_2$ are as defined above.
Interesting are compounds of the formulae (I) or (II) as shown above, wherein
X is

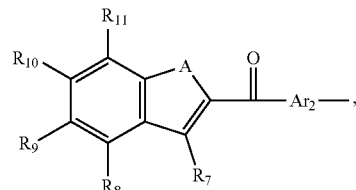

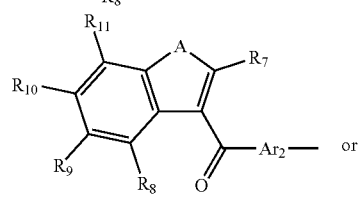

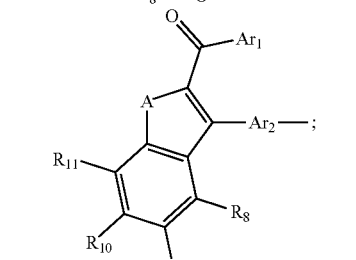

A is O, S, NR$_5$ or CR$_{16}$R$_{17}$;

R$_1$ is C$_1$-C$_{20}$alkyl which is unsubstituted or substituted by one or more halogen, OR$_3$, SR$_4$, NR$_5$R$_6$, (CO)OR$_3$, C$_3$-C$_8$cycloalkyl or C$_3$-C$_8$cycloalkyl which is interrupted by one or more O;

or R$_1$ is C$_2$-C$_{20}$alkyl interrupted by one or more O, which interrupted C$_2$-C$_{20}$alkyl is unsubstituted or substituted by one or more OH, O(CO)R$_{1a}$ or (CO)OR$_3$;

or R$_1$ is C$_2$-C$_{12}$alkenyl or C$_3$-C$_{20}$cycloalkyl;

or R$_1$ is C$_6$-C$_{20}$aryl or C$_3$-C$_{20}$heteroaryl, each of which is unsubstituted or substituted by one or more halogen or C$_1$-C$_{20}$alkyl;

or R$_1$ is C$_1$-C$_{20}$alkoxy, C$_6$-C$_{20}$aryloxy or C$_3$-C$_{20}$heteroaryloxy;

R$_{1a}$ is hydrogen, C$_1$-C$_{20}$alkyl, C$_2$-C$_{20}$alkyl interrupted by one or more O, C$_2$-C$_{12}$alkenyl, C$_3$-C$_{20}$cycloalkyl, C$_6$-C$_{20}$aryl or C$_3$-C$_{20}$heteroaryl, which C$_6$-C$_{20}$aryl or C$_3$-C$_{20}$heteroaryl is unsubstituted or substituted by one or more halogen, C$_1$-C$_{20}$alkyl, OR$_{3a}$, SR$_{4a}$, NR$_{5a}$R$_{6a}$, COOR$_{3a}$, (CO)—(C$_1$-C$_8$alkyl) or benzoyl;

or R$_{1a}$ is C$_6$-C$_{20}$aryloxy or C$_3$-C$_{20}$heteroaryloxy, which C$_6$-C$_{20}$aryloxy or C$_3$-C$_{20}$heteroaryloxy is unsubstituted or substituted by benzoyl, or

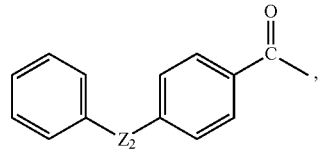

which benzoyl or

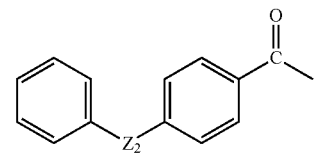

is unsubstituted or substituted by

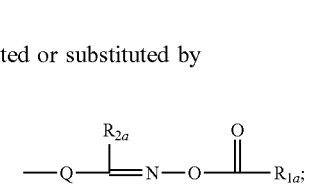

R$_2$ is hydrogen, C$_1$-C$_{20}$alkyl which is unsubstituted or substituted by one or more substituents halogen, OR$_3$, SR$_4$, NR$_5$R$_6$, (CO)OR$_3$,

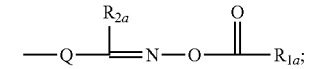

or C$_3$-C$_8$cycloalkyl which is uninterrupted or interrupted by one or more O;

or R$_2$ is C$_2$-C$_{20}$alkyl interrupted by one or more O, which interrupted C$_2$-C$_{20}$alkyl is unsubstituted or substituted by one or more C$_3$-C$_8$cycloalkyl, OH, O(CO)R$_{1a}$ or (CO)OR$_3$;

or R$_2$ is C$_2$-C$_{12}$alkenyl, C$_3$-C$_{20}$cycloalkyl or C$_6$-C$_{20}$aryl, which C$_6$-C$_{20}$aryl or C$_3$-C$_{20}$heteroaryl is unsubstituted or substituted by one or more halogen, NO$_2$, OR$_3$, SR$_4$, COOR$_3$, (CO)—R$_{1a}$ or

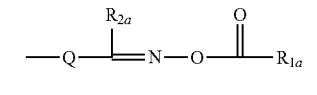

R$_{2a}$ is hydrogen, (CO)R$_{1a}$, (CO)OR$_{3a}$, C$_1$-C$_{20}$alkyl which is unsubstituted or substituted by one or more halogen, OR$_{3a}$, SR$_{4a}$ or C$_3$-C$_8$cycloalkyl which is uninterrupted or interrupted by one or more O;

R$_3$ is hydrogen, (CO)R$_{1a}$, C$_1$-C$_{20}$alkyl which is unsubstituted or substituted by one or more C$_3$-C$_8$cycloalkyl which is uninterrupted or interrupted by one or more O;

or R$_3$ is C$_2$-C$_{20}$alkyl interrupted by one or more O, which interrupted C$_2$-C$_{20}$alkyl is unsubstituted or substituted by one or more C$_3$-C$_8$cycloalkyl, OH or (CO)OR$_{3a}$;

or R$_3$ is C$_2$-C$_{12}$alkenyl, C$_3$-C$_{20}$cycloalkyl or C$_6$-C$_{20}$aryl, which C$_6$-C$_{20}$aryl is unsubstituted or substituted by one or more halogen or C$_1$-C$_{20}$alkyl;

$R_{3a}$ is $C_1$-$C_{20}$alkyl;

$R_4$ is hydrogen, $C_1$-$C_{20}$alkyl which is unsubstituted or substituted by one or more $OR_{3a}$, $(CO)OR_{3a}$, $C_3$-$C_8$cycloalkyl or $C_6$-$C_{20}$aryl;

or $R_4$ is $C_2$-$C_{20}$alkyl interrupted by one or more O, which interrupted $C_2$-$C_{20}$alkyl is unsubstituted or substituted by one or more OH or $(CO)OR_{3a}$;

or $R_4$ is $C_2$-$C_{12}$alkenyl or $C_3$-$C_{20}$cycloalkyl;

or $R_4$ is $C_6$-$C_{20}$aryl which is unsubstituted or substituted by one or more halogen or $C_2$-$C_{20}$alkyl which is uninterrupted or interrupted by one or more O;

$R_{4a}$ is $C_1$-$C_{20}$alkyl;

$R_5$ and $R_6$ independently of each other are hydrogen, $C_1$-$C_{20}$alkyl which is unsubstituted or substituted by one or more halogen, $OR_{3a}$, $SR_{4a}$, $(CO)OR_{3a}$, $C_3$-$C_8$cycloalkyl or $C_6$-$C_{20}$aryl;

or $R_5$ and $R_6$ independently of each other are $C_2$-$C_{20}$alkyl interrupted by one or more O, which interrupted $C_2$-$C_{20}$alkyl is unsubstituted or substituted by OH or SH;

or $R_5$ and $R_6$ independently of each other are $C_2$-$C_{12}$alkenyl, $C_3$-$C_{20}$cycloalkyl or $C_6$-$C_{20}$aryl;

or $R_5$ and $R_6$ together with the N-atom to which they are attached form a 5- or 6-membered saturated or unsaturated ring which is uninterrupted or interrupted by O, S or $NR_{5a}$;

$R_{5a}$ and $R_{6a}$ independently of each other are hydrogen or $C_1$-$C_{20}$alkyl;

$R_7$, $R_8$, $R_9$, $R_{10}$ and $R_{11}$ independently of each other are hydrogen, $C_1$-$C_{20}$alkyl, $OR_3$, $SR_4$, $NR_5R_6$, $COOR_3$, $(CO)R_{1a}$;

or $R_7$, $R_8$, $R_9$, $R_{10}$ and $R_{11}$ independently of each other are $C_1$-$C_{20}$alkyl substituted by one or more halogen, $OR_3$, $SR_4$, $NR_5R_6$, $(CO)OR_3$, $C_6$-$C_{20}$aryl or $C_3$-$C_8$cycloalkyl which is uninterrupted or interrupted by one or more O;

or $R_7$, $R_8$, $R_9$, $R_{10}$ and $R_{11}$ independently of each other are $C_2$-$C_{20}$alkyl interrupted by one or more O;

or $R_7$, $R_8$, $R_9$, $R_{10}$ and $R_{11}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $OR_3$, $SR_4$, $NR_5R_6$, $COOR_3$, $(CO)R_{1a}$ or

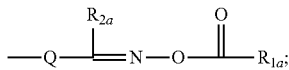

or $R_8$ and $R_9$, $R_9$ and $R_{10}$, or $R_{10}$ and $R_{11}$ are

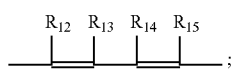

$R_{12}$, $R_{13}$, $R_{14}$ and $R_{15}$ independently of each other are hydrogen or $C_1$-$C_{20}$alkyl;

$Ar_1$ is $C_6$-$C_{20}$aryl, $C_3$-$C_{20}$heteroaryl, $C_6$-$C_{20}$aroyl, $C_3$-$C_{20}$heteroarylcarbonyl or

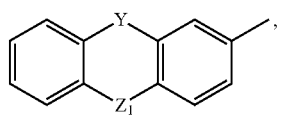

which $C_6$-$C_{20}$aryl, $C_3$-$C_{20}$heteroaryl, $C_6$-$C_{20}$aroyl, $C_3$-$C_{20}$heteroaryl carbonyl or

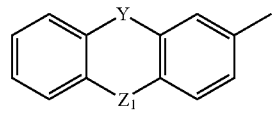

is unsubstituted or substituted by one or more halogen, $COOR_3$, $(CO)R_{1a}$,

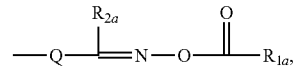

$OR_3$, $SR_4$, $NR_5R_6$, $C_1$-$C_{20}$alkyl, $C_2$-$C_{20}$alkyl which is interrupted by one or more O, $C_2$-$C_{12}$alkenyl, $C_3$-$C_{20}$cycloalkyl or phenyl;

or $Ar_1$ is

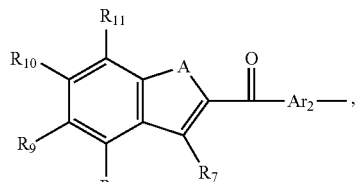

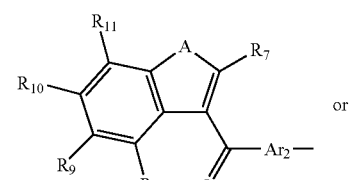

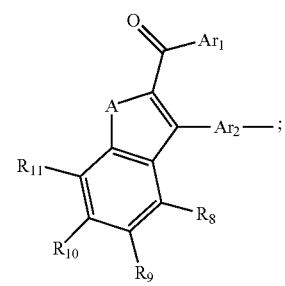

$Ar_2$ is phenylene, naphthylene,

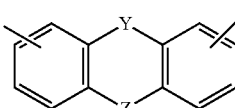

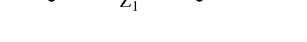

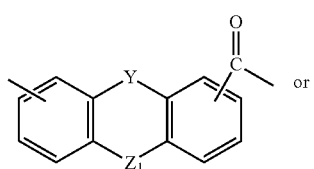

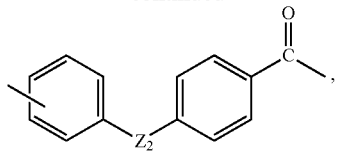

which phenylene, naphthylene,

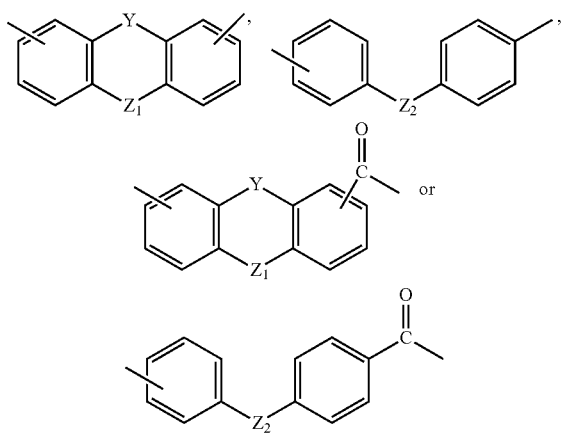

is unsubstituted or substituted by one or more halogen, COOR$_3$, (CO)R$_{1a}$,

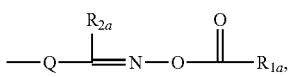

OR$_3$, SR$_4$, NR$_5$R$_6$, C$_1$-C$_{20}$alkyl, C$_2$-C$_{12}$alkenyl, C$_3$-C$_{20}$cycloalkyl, phenyl or C$_2$-C$_{20}$alkyl which is interrupted by one or more O;

M is C$_1$-C$_{20}$alkylene, C$_2$-C$_{20}$alkylene interrupted by one or more O or S, C$_2$-C$_{12}$alkenylene, C$_3$-C$_{20}$cycloalkylene or C$_6$-C$_{20}$arylene;

Y is a direct bond, O, S, NR$_5$ or CO;
Z$_1$ is O, S, CO or CR$_{16}$(R$_{17}$);
Z$_2$ is a direct bond, O, S or NR$_5$; and
Q is CO or a direct bond.

Preferred are compounds of the formula (I) as shown above, wherein
X is

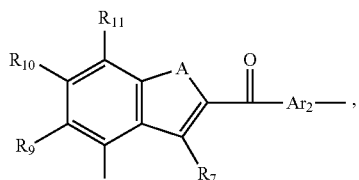

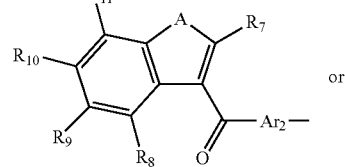

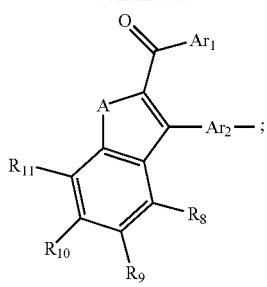

A is O or S;
R$_1$ is C$_1$-C$_{20}$alkyl;
R$_{1a}$ is C$_6$-C$_{20}$aryl;
R$_2$ is C$_1$-C$_{20}$alkyl which is unsubstituted or substituted by one or more halogen, OR$_3$, SR$_4$, (CO)OR$_3$ or C$_3$-C$_8$cycloalkyl which is uninterrupted or is interrupted by one or more O;

R$_7$, R$_8$, R$_9$, R$_{10}$ and R$_{11}$ independently of each other are hydrogen, OR$_3$, C$_1$-C$_{20}$alkyl, (CO)R$_{1a}$, or R$_8$ and R$_9$ are

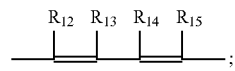

R$_{12}$, R$_{13}$, R$_{14}$ and R$_{15}$ are hydrogen;
Ar$_2$ is

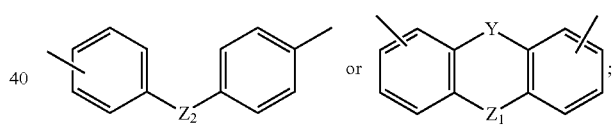

and

Z$_2$ is O or S.

Interesting are compounds of the formula I, wherein
X is

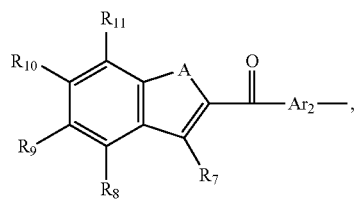

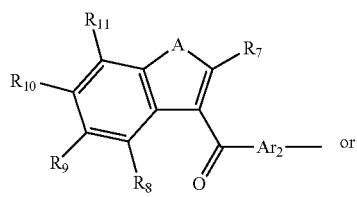

-continued

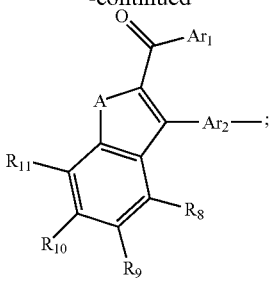

A is O, S or NR$_5$;

R$_1$ is C$_1$-C$_{20}$alkyl, C$_6$-C$_{20}$aryl or C$_1$-C$_{20}$alkoxy;

R$_{1a}$ is C$_1$-C$_{20}$alkyl or C$_6$-C$_{20}$aryl;

R$_2$ is C$_1$-C$_{20}$alkyl which is unsubstituted or substituted by halogen, SR$_4$, NR$_5$R$_6$, (CO)OR$_3$ or C$_3$-C$_8$cycloalkyl;

or R$_2$ is C$_6$-C$_{20}$aryl which is unsubstituted or substituted by C$_1$-C$_{20}$alkyl;

R$_3$ is C$_1$-C$_{20}$alkyl or R$_3$ together with one of the carbon atoms of R$_2$ forms a 5- or 6-membered, preferably 6-membered, saturated ring;

R$_4$ is C$_6$-C$_{20}$aryl;

R$_5$ and R$_6$ independently of each other are O(CO)R$_{1a}$, (CO)R$_{1a}$ or C$_1$-C$_{20}$alkyl;

R$_7$, R$_8$, R$_9$, R$_{10}$ and R$_{11}$ independently of each other are hydrogen, C$_1$-C$_{20}$alkyl, halogen, NO$_2$, OR$_3$, (CO)R$_{1a}$ or C$_6$-C$_{20}$aryl;

or R$_8$ and R$_9$ are

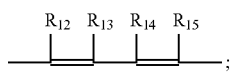

R$_{12}$, R$_{13}$, R$_{14}$ and R$_{15}$ are hydrogen or C$_1$-C$_4$alkyl, preferably hydrogen;

R$_{16}$ and R$_{17}$ are hydrogen;

or R$_{16}$ and R$_{17}$ together with the carbon atom to which they are attached form a 5- or 6-membered saturated ring;

Ar$_1$ is C$_6$-C$_{20}$aryl or

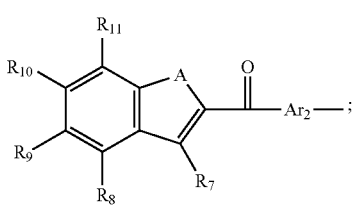

Ar$_2$ is

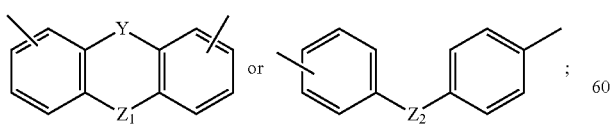

M is C$_2$-C$_{20}$alkylene interrupted by S;

Y is a direct bond;

Z$_1$ is O, S or CR$_{16}$(R$_{17}$); and

Z$_2$ is O or S.

X is for example

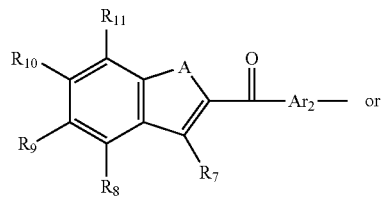

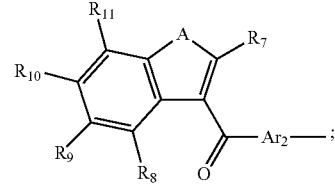

or is for example

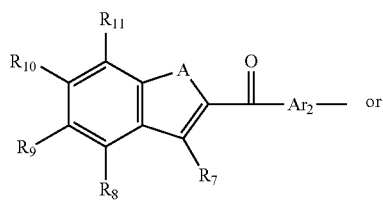

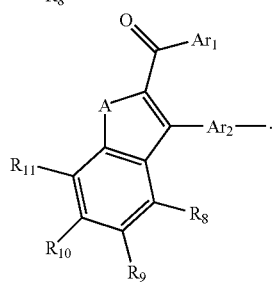

preferably X is

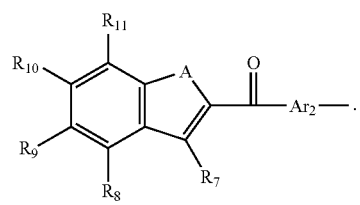

A is for example O, S or NR$_5$; or is for example O, S or CR$_{16}$R$_{17}$; or is for example O or S; or is for example O or NR$_5$; or is for example O, S or CR$_{16}$R$_{17}$; or is for example O or CR$_{16}$R$_{17}$. Preferably A is O.

Ar$_1$ is for example C$_6$-C$_{20}$aryl, C$_3$-C$_{20}$heteroaryl,

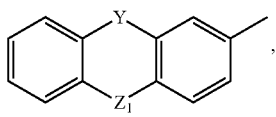

-continued

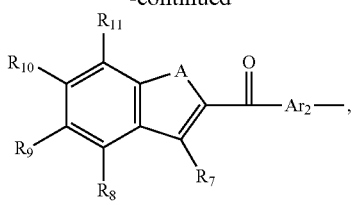

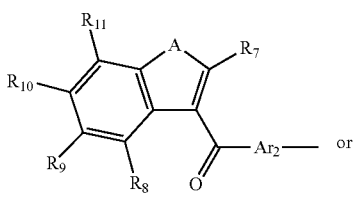

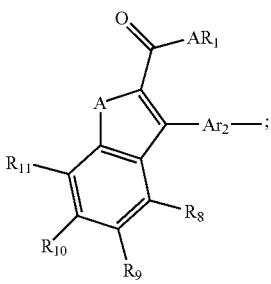

or Ar$_1$ is for example C$_6$-C$_{20}$aryl, C$_3$-C$_{20}$heteroaryl, C$_6$-C$_{20}$aroyl or C$_3$-C$_{20}$heteroaroyl; or Ar$_1$ is for example C$_6$-C$_{20}$aryl, C$_6$-C$_{20}$aroyl,

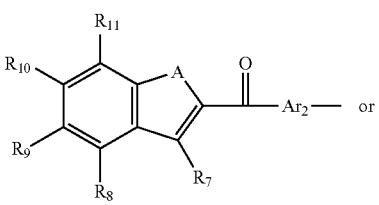

or Ar$_1$ is for example C$_6$-C$_{20}$aryl, C$_3$-C$_{20}$heteroaryl, C$_6$-C$_{20}$aroyl or C$_3$-C$_{20}$heteroaroyl; or Ar$_1$ is for example C$_6$-C$_{20}$aryl, C$_6$-C$_{20}$aroyl or

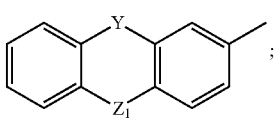

Preferably Ar$_1$ is C$_6$-C$_{20}$aryl or

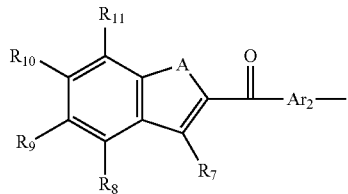

Substituted Ar$_1$ are for example substituted by one or more substituents selected from the group consisting of halogen, COOR$_3$, (CO)R$_{1a}$,

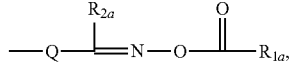

OR$_3$, SR$_4$, NR$_5$R$_6$, C$_1$-C$_{20}$alkyl, C$_2$-C$_{20}$alkyl which is interrupted by one or more O, C$_2$-C$_{12}$alkenyl, C$_3$-C$_{20}$cycloalkyl, phenyl, naphthyl, benzoyl and naphthoyl;

or are for example substituted by one or more substituents selected from the group consisting of halogen, CN, NO$_2$, COOR$_3$, (CO)R$_{1a}$, (CO)NR$_5$R$_6$,

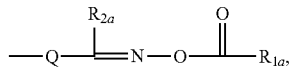

OR$_3$, SR$_4$, NR$_5$R$_6$, C$_1$-C$_{20}$alkyl, C$_2$-C$_{20}$alkyl which is interrupted by one or more O, C$_3$-C$_{20}$cycloalkyl, phenyl and naphthyl;

or are for example substituted by one or more substituents selected from the group consisting of halogen, COOR$_3$, (CO)R$_{1a}$, (CO)NR$_5$R$_6$,

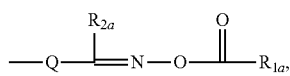

OR$_3$, C$_1$-C$_{20}$alkyl, C$_2$-C$_{20}$alkyl which is interrupted by one or more O, C$_3$-C$_{20}$cycloalkyl, phenyl and naphthyl.

Ar$_2$ for example is phenylene, naphthylene,

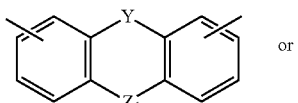

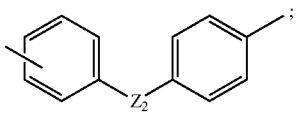

or Ar$_2$ for example is phenylene, naphthylene, phenylenecarbonyl, naphthylenecarbonyl,

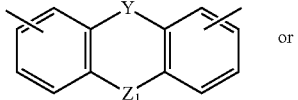

-continued

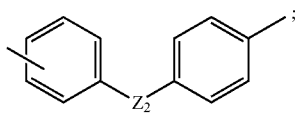

or Ar$_2$ for example is phenylene, phenylenecarbonyl,

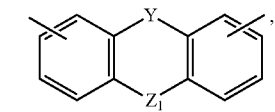

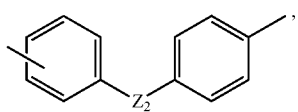

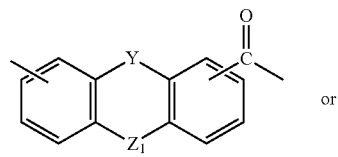

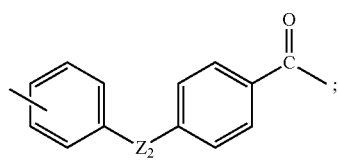

or Ar$_2$ for example is phenylene, naphthylene, phenylenecarbonyl, naphthylenecarbonyl

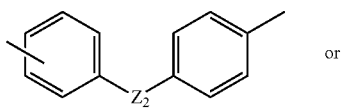

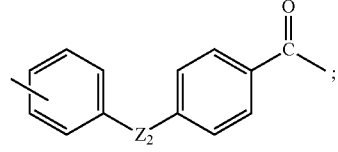

or Ar$_2$ for example is phenylene, naphthylene

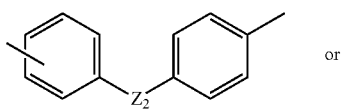

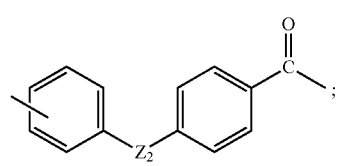

or Ar$_2$ for example is phenylene, naphthylene or

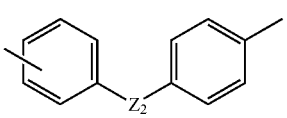

Ar$_2$ preferably is

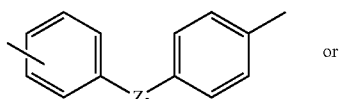      or

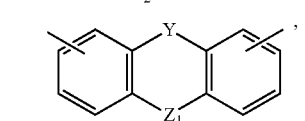

in particular

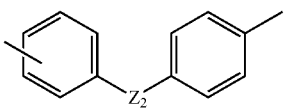

Examples for substituted Ar$_2$ are as given above for substituents on Ar$_1$.

M is for example $C_1$-$C_{20}$alkylene which is unsubstituted or substituted by one or more substituents selected from the group consisting of halogen, OR$_3$, SR$_4$, NR$_5$R$_6$, (CO)OR$_3$, (CO)NR$_5$R$_6$, $C_3$-$C_8$cycloalkyl which is uninterrupted or interrupted by one or more O and $C_6$-$C_{20}$aryl; or M is $C_2$-$C_{20}$alkylene interrupted by one or more O or S, $C_2$-$C_{12}$alkenylene, $C_3$-$C_{20}$cycloalkylene or $C_6$-$C_{20}$arylene.

Or M is for example $C_1$-$C_{20}$alkylene, $C_2$-$C_{20}$alkylene interrupted by one or more O or S, $C_2$-$C_{12}$alkenylene, $C_3$-$C_{20}$cycloalkylene or $C_6$-$C_{20}$arylene.

Preferably M is $C_1$-$C_{20}$alkylene or $C_2$-$C_{20}$alkylene interrupted by one or more O or S, in particular by S Or M in particular is $C_2$-$C_{20}$alkylene interrupted by one or more O or S, in particular by S.

Y is for example a direct bond, O, S or NR$_5$; or is for example direct bond, O, S, or CO; or is for example direct bond, O, NR$_5$ or CO; or is for example direct bond, O or CO; or is for example O, S, NR$_5$ or CO; or is for example O, S or CO; or is for example O or CO.

Z$_1$ is for example O, CO or CR$_{16}$(R$_{17}$); or is for example O, S or CR$_{16}$(R$_{17}$); or is for example O, S or CO; or is for example S, CO or CR$_{16}$(R$_{17}$); or is for example O or S.

Z$_2$ is for example a direct bond, O or S; or is for example O, S or NR$_5$; or is for example O or S; or is for example a direct bond or S; or is for example S or NR$_5$. Preferably Z$_2$ is S.

Q is for example CO or a direct bond, preferably a direct bond.

R$_1$ is for example hydrogen, $C_1$-$C_{20}$alkyl which is unsubstituted or substituted by one or more substituents selected from the group consisting of halogen, OR$_3$, SR$_4$, NR$_5$R$_6$, CN, $C_3$-$C_8$cycloalkyl and $C_6$-$C_{20}$aryl; or R$_1$ is $C_2$-$C_{20}$alkyl interrupted by one or more O, or is $C_2$-$C_{12}$alkenyl, $C_3$-$C_{20}$cycloalkyl, $C_6$-$C_{20}$aryl, $C_3$-$C_{20}$heteroaryl, $C_1$-$C_{20}$alkoxy, $C_2$-$C_{20}$alkoxy, which is interrupted by one or more O; or R$_1$ is $C_6$-$C_{20}$aryloxy or $C_3$-$C_{20}$heteroaryloxy.

Or $R_1$ is for example $C_1$-$C_{20}$alkyl which is unsubstituted or substituted by one or more halogen, CN, $C_3$-$C_8$cycloalkyl or $C_6$-$C_{20}$aryl; or $R_1$ is $C_2$-$C_{20}$alkyl interrupted by one or more O, or is $C_2$-$C_{12}$alkenyl, $C_3$-$C_{20}$cycloalkyl, $C_6$-$C_{20}$aryl, $C_3$-$C_{20}$heteroaryl, $C_1$-$C_{20}$alkoxy, $C_2$-$C_{20}$alkoxy, which is interrupted by one or more O; or $R_1$ is $C_6$-$C_{20}$aryloxy or $C_3$-$C_{20}$heteroaryloxy.

Or $R_1$ is for example $C_1$-$C_{20}$alkyl which is unsubstituted or substituted by one or more halogen, CN or $C_6$-$C_{20}$aryl; or $R_1$ is $C_2$-$C_{20}$alkyl interrupted by one or more O, or is $C_3$-$C_{20}$cycloalkyl, $C_6$-$C_{20}$aryl, $C_3$-$C_{20}$heteroaryl, $C_1$-$C_{20}$alkoxy, $C_2$-$C_{20}$alkoxy, which is interrupted by one or more O; or $R_1$ is $C_6$-$C_{20}$aryloxy or $C_3$-$C_{20}$heteroaryloxy.

Or $R_1$ is for example $C_1$-$C_{20}$alkyl which is unsubstituted or substituted by one or more halogen, CN or $C_6$-$C_{20}$aryl; or $R_1$ is $C_2$-$C_{20}$alkyl interrupted by one or more O, or is $C_3$-$C_{20}$cycloalkyl, $C_1$-$C_{20}$alkoxy, $C_2$-$C_{20}$alkoxy, which is interrupted by one or more O.

Or $R_1$ is for example $C_1$-$C_{20}$alkyl which is unsubstituted or substituted by one or more halogen, CN or phenyl; or $R_1$ is $C_2$-$C_{20}$alkyl interrupted by one or more O, or is $C_3$-$C_{20}$cycloalkyl, $C_1$-$C_{20}$alkoxy, $C_2$-$C_{20}$alkoxy, which is interrupted by one or more O; or $R_1$ is $C_6$-$C_{20}$aryloxy or $C_3$-$C_{20}$heteroaryloxy.

Or $R_1$ is for example $C_1$-$C_{20}$alkyl which is unsubstituted or substituted by one or more halogen, CN or $C_6$-$C_{20}$aryl; or $R_1$ is $C_2$-$C_{20}$alkyl interrupted by one or more O, or is $C_3$-$C_{20}$cycloalkyl, $C_6$-$C_{20}$aryl, $C_3$-$C_{20}$heteroaryl.

Or $R_1$ is for example $C_1$-$C_6$alkyl which is unsubstituted or substituted by one or more halogen or phenyl, which is unsubstituted or substituted by one or more $C_1$-$C_6$alkyl, halogen, $OR_3$, $SR_4$ and/or $NR_5R_6$; or $R_1$ is $C_1$-$C_6$alkoxy or benzyloxy.

Or $R_1$ is for example $C_1$-$C_{12}$alkyl, phenyl or $C_1$-$C_8$alkoxy. Preferably $R_1$ is $C_1$-$C_{12}$alkyl.

$R_{1a}$ for example is hydrogen, $C_1$-$C_{20}$alkyl, $C_2$-$C_{20}$alkyl interrupted by one or more O, $C_2$-$C_{12}$alkenyl, $C_3$-$C_{20}$cycloalkyl, $C_6$-$C_{20}$aryl, $C_3$-$C_{20}$heteroaryl, $C_1$-$C_{20}$alkoxy, $C_2$-$C_{20}$alkoxy interrupted by one or more O, $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_{3a}$, $SR_{4a}$, $NR_{5a}R_{6a}$, $COOR_{3a}$, (CO)($C_1$-$C_8$alkyl), $SO_2$—($C_1$-$C_4$haloalkyl), benzoyl, or

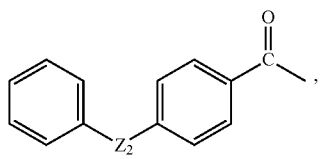

which benzoyl or

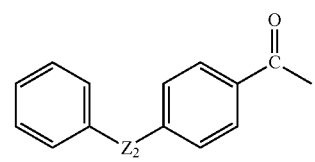

is unsubstituted or substituted by

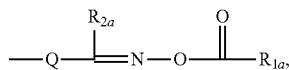

Or $R_{1a}$ for example is hydrogen, $C_1$-$C_{20}$alkyl, $C_2$-$C_{20}$alkyl interrupted by one or more O, $C_2$-$C_{12}$alkenyl, $C_3$-$C_{20}$cycloalkyl, $C_6$-$C_{20}$aryl, $C_3$-$C_{20}$heteroaryl, $C_1$-$C_{20}$alkoxy, $C_2$-$C_{20}$alkoxy interrupted by one or more O, $C_6$-$C_{20}$aryloxy or $C_3$-$C_{20}$heteroaryloxy.

Or $R_{1a}$ for example is hydrogen, $C_1$-$C_{20}$alkyl, $C_2$-$C_{20}$alkyl interrupted by one or more O, $C_2$-$C_{12}$alkenyl, $C_3$-$C_{20}$cycloalkyl or $C_6$-$C_{20}$aryl, in particular phenyl.

Or $R_{1a}$ for example is $C_1$-$C_{20}$alkyl, $C_2$-$C_{20}$alkyl interrupted by one or more O, $C_2$-$C_{12}$alkenyl or $C_3$-$C_{20}$cycloalkyl.

Or $R_{1a}$ for example is $C_1$-$C_{20}$alkyl, $C_2$-$C_{20}$alkyl interrupted by one or more O, or $C_6$-$C_{20}$aryl, in particular phenyl.

$R_{1a}$ preferably is $C_6$-$C_{20}$aryl.

$R_2$ for example is hydrogen, $(CO)R_{1a}$, $(CO)OR_3$ or $CONR_5R_6$;

or $R_2$ is $C_1$-$C_{20}$alkyl which is unsubstituted or substituted by one or more substituents selected from the group consisting of halogen, $OR_3$, $SR_4$, $NR_5R_6$, $(CO)OR_3$, $(CO)NR_5R_6$,

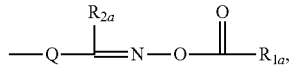

$C_3$-$C_8$cycloalkyl which is uninterrupted or interrupted by one or more O, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_4$haloalkyl, $OR_3$, $SR_4$ or $NR_5R_6$;

or $R_2$ is $C_2$-$C_{20}$alkyl interrupted by one or more O, which interrupted $C_2$-$C_{20}$alkyl is unsubstituted or substituted by one or more $C_3$-$C_8$cycloalkyl, OH, SH or $C_6$-$C_{20}$aryl;

or $R_2$ is $C_2$-$C_{12}$alkenyl, $C_3$-$C_{20}$cycloalkyl, $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_3$, $SR_4$, $NR_5R_6$, $COOR_3$, $(CO)R_{1a}$,

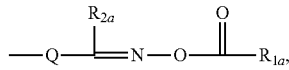

$C_1$-$C_{20}$alkyl, $C_2$-$C_{20}$alkyl which is interrupted by one or more O, phenyl, naphthyl, benzoyl and naphthoyl, which phenyl, naphthyl, benzoyl or naphthoyl is unsubstituted or substituted by one or more $OR_3$, $SR_4$ or $NR_5R_6$.

Or $R_2$ for example is hydrogen, $(CO)R_{1a}$, $(CO)OR_3$ or $CONR_5R_6$;

or $R_2$ is $C_1$-$C_{20}$alkyl which is unsubstituted or substituted by one or more substituents selected from the group consisting of halogen, $OR_3$, $SR_4$, $NR_5R_6$, $(CO)OR_3$, $(CO)NR_5R_6$,

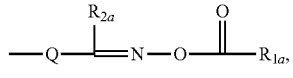

$C_3$-$C_8$cycloalkyl which is uninterrupted or interrupted by one or more O, $C_6$-$C_{20}$aryl, $C_3$-$C_{20}$heteroaryl, $C_6$-$C_{20}$aroyl and $C_3$-$C_{20}$heteroarylcarbonyl;

or $R_2$ is $C_2$-$C_{20}$alkyl interrupted by one or more O, which interrupted $C_2$-$C_{20}$alkyl is unsubstituted or substituted by one or more $C_3$-$C_8$cycloalkyl;

or $R_2$ is $C_2$-$C_{12}$alkenyl, $C_3$-$C_{20}$cycloalkyl, $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, $NO_2$, $OR_3$, $SR_4$, $NR_5R_6$, $COOR_3$, $(CO)R_{1a}$,

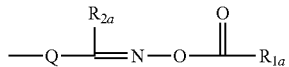

and $C_1$-$C_{20}$alkyl.

Or $R_2$ for example is $C_1$-$C_{20}$alkyl which is unsubstituted or substituted by one or more substituents selected from the group consisting of halogen, $OR_3$, $SR_4$, $NR_5R_6$, $(CO)OR_3$, $(CO)NR_5R_6$,

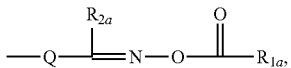

$C_3$-$C_8$cycloalkyl which is uninterrupted or interrupted by one or more O, $C_6$-$C_{20}$aryl, $C_3$-$C_{20}$heteroaryl, $C_6$-$C_{20}$aroyl and $C_3$-$C_{20}$heteroarylcarbonyl;

or $R_2$ is $C_2$-$C_{20}$alkyl interrupted by one or more O, $C_2$-$C_{12}$alkenyl, $C_3$-$C_{20}$cycloalkyl or $C_6$-$C_{20}$aryl.

Or $R_2$ for example is $C_1$-$C_{20}$alkyl which is unsubstituted or substituted by one or more substituents selected from the group consisting of halogen, $OR_3$, $SR_4$, $NR_5R_6$, $(CO)OR_3$, $(CO)NR_5R_6$,

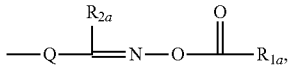

$C_3$-$C_8$cycloalkyl, or $R_2$ is $C_2$-$C_{20}$alkyl interrupted by one or more O, $C_2$-$C_{12}$alkenyl or $C_3$-$C_{20}$cycloalkyl.

Or $R_2$ for example is $C_1$-$C_{20}$alkyl, $C_2$-$C_{20}$alkyl interrupted by one or more O, $C_2$-$C_{12}$alkenyl or $C_3$-$C_{20}$cycloalkyl.

Or $R_2$ for example is $C_1$-$C_{20}$alkyl or $C_2$-$C_{20}$alkyl interrupted by one or more O.

Preferably $R_2$ is $C_1$-$C_{20}$alkyl.

$R_{2a}$ is for example hydrogen, $(CO)R_{1a}$, $(CO)OR_{3a}$, $CONR_{5a}R_{6a}$, $C_1$-$C_{20}$alkyl which is unsubstituted or substituted by one or more halogen, $OR_{3a}$, $SR_{4a}$, $NR_{5a}R_{6a}$, $(CO)OR_{3a}$, $(CO)NR_{5a}R_{6a}$ or $C_3$-$C_8$cycloalkyl which is uninterrupted or interrupted by one or more O;

or $R_{2a}$ is $C_2$-$C_{20}$alkyl interrupted by one or more O; or $R_{2a}$ is $C_2$-$C_{12}$alkenyl, $C_3$-$C_{20}$cycloalkyl, $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $OR_{3a}$, $SR_{4a}$, $NR_{5a}R_{6a}$, $COOR_{3a}$, $(CO)R_{1a}$, $(CO)NR_{5a}R_{6a}$ or $C_1$-$C_{20}$alkyl.

Or $R_{2a}$ is for example $C_1$-$C_{20}$alkyl which is unsubstituted or substituted by one or more halogen, $OR_{3a}$, $SR_{4a}$, $NR_{5a}R_{6a}$, $(CO)OR_{3a}$, $(CO)NR_{5a}R_{6a}$ or $C_3$-$C_8$cycloalkyl which is uninterrupted or interrupted by one or more O; or $R_{2a}$ is $C_2$-$C_{20}$alkyl interrupted by one or more O; or $R_{2a}$ is $C_2$-$C_{12}$alkenyl or $C_3$-$C_{20}$cycloalkyl.

Or $R_{2a}$ is for example $C_1$-$C_{20}$alkyl which is unsubstituted or substituted by one or more halogen, $OR_{3a}$, $SR_{4a}$, $NR_{5a}R_{6a}$, $(CO)OR_{3a}$ or $C_3$-$C_8$cycloalkyl which is uninterrupted or interrupted by one or more O; or $R_{2a}$ is $C_2$-$C_{20}$alkyl interrupted by one or more O; or $R_{2a}$ is $C_2$-$C_{12}$alkenyl or $C_3$-$C_{20}$cycloalkyl.

Or $R_{2a}$ is for example $C_1$-$C_{20}$alkyl, $C_2$-$C_{20}$alkyl interrupted by one or more O, $C_2$-$C_{12}$alkenyl or $C_3$-$C_{20}$cycloalkyl.

In particular $R_{2a}$ is $C_1$-$C_{20}$alkyl.

$R_3$ is for example hydrogen, $(CO)R_{1a}$, $(CO)OR_{3a}$, $C_1$-$C_{20}$alkyl which is unsubstituted or substituted by one or more halogen, $C_3$-$C_8$cycloalkyl which is uninterrupted or interrupted by one or more O; or $R_3$ is $C_2$-$C_{20}$alkyl interrupted by one or more O, which interrupted $C_2$-$C_{20}$alkyl is unsubstituted or substituted by one or more $C_3$-$C_8$cycloalkyl, OH or $(CO)OR_{3a}$; or $R_3$ is $C_2$-$C_{12}$alkenyl or $C_3$-$C_{20}$cycloalkyl; or $R_3$ is $C_6$-$C_{20}$aryl which is unsubstituted or substituted by one or more halogen or $C_1$-$C_{20}$alkyl.

Or $R_3$ is for example hydrogen, $(CO)R_{1a}$, $(CO)OR_{3a}$, $C_1$-$C_{20}$alkyl, $C_2$-$C_{20}$alkyl interrupted by one or more O, $C_2$-$C_{12}$alkenyl or $C_3$-$C_{20}$cycloalkyl;

or $R_3$ is $C_6$-$C_{20}$aryl which is unsubstituted or substituted by one or more halogen or $C_1$-$C_{20}$alkyl.

Or $R_3$ is for example hydrogen, $C_1$-$C_{20}$alkyl, $C_3$-$C_{20}$cycloalkyl or $C_6$-$C_{20}$aryl.

$R_{1a}$ for example is hydrogen, $C_1$-$C_{20}$alkyl, $C_2$-$C_{20}$alkyl interrupted by one or more O, $C_2$-$C_{12}$alkenyl, $C_3$-$C_8$cycloalkyl, $C_6$-$C_{20}$aryl, $C_3$-$C_{20}$heteroaryl, $C_1$-$C_{20}$alkanoyl or $C_3$-$C_{12}$alkenoyl.

Or $R_{3a}$ for example is hydrogen, $C_1$-$C_{20}$alkyl, $C_3$-$C_8$cycloalkyl, $C_6$-$C_{20}$aryl, $C_1$-$C_{20}$alkanoyl or $C_3$-$C_{12}$alkenoyl.

Or $R_{3a}$ for example is hydrogen, $C_1$-$C_{20}$alkyl, $C_3$-$C_8$cycloalkyl or $C_1$-$C_{20}$alkanoyl.

Or $R_{3a}$ for example is $C_1$-$C_{20}$alkyl.

$R_4$ for example is hydrogen, $C_1$-$C_{20}$alkyl which is unsubstituted or substituted by one or more substituents $OR_{3a}$, $(CO)OR_{3a}$, $C_3$-$C_8$cycloalkyl or $C_6$-$C_{20}$aryl; or $R_4$ is $C_2$-$C_{20}$alkyl interrupted by one or more O, which interrupted $C_2$-$C_{20}$alkyl is unsubstituted or substituted by one or more OH or $(CO)OR_{3a}$; or $R_4$ is $C_2$-$C_{12}$alkenyl or $C_3$-$C_{20}$cycloalkyl.

Or $R_4$ for example is hydrogen, $C_1$-$C_{20}$alkyl, $C_2$-$C_{20}$alkyl interrupted by one or more O, $C_2$-$C_{12}$alkenyl or $C_3$-$C_{20}$cycloalkyl.

Or $R_4$ for example is $C_1$-$C_{20}$alkyl.

$R_{4a}$ for example is hydrogen, $C_1$-$C_{20}$alkyl, $C_2$-$C_{20}$alkyl interrupted by one or more O, $C_2$-$C_{12}$alkenyl, $C_6$-$C_{20}$aryl, $C_3$-$C_{20}$heteroaryl, $C_1$-$C_{20}$alkanoyl or $C_3$-$C_{12}$alkenoyl.

Or $R_{4a}$ for example is hydrogen, $C_1$-$C_{20}$alkyl, $C_2$-$C_{20}$alkyl interrupted by one or more O, $C_2$-$C_{12}$alkenyl, $C_1$-$C_{20}$alkanoyl or $C_3$-$C_{12}$alkenoyl.

Or $R_{4a}$ for example is hydrogen, $C_1$-$C_{20}$alkyl, $C_2$-$C_{20}$alkyl interrupted by one or more O, or $C_1$-$C_{20}$alkanoyl.

Or $R_{4a}$ for example is hydrogen, $C_1$-$C_{20}$alkyl or $C_2$-$C_{20}$alkyl interrupted by one or more O. Or $R_{4a}$ for example is $C_1$-$C_{20}$alkyl.

$R_5$ and $R_6$ independently of each other are hydrogen, $C_1$-$C_{20}$alkyl which is unsubstituted or substituted by one or more halogen, $OR_{3a}$, $SR_{4a}$, $(CO)OR_{3a}$, $C_3$-$C_8$cycloalkyl or $C_6$-$C_{20}$aryl; or $R_5$ and $R_6$ independently of each other are $C_2$-$C_{20}$alkyl interrupted by one or more O, which interrupted $C_2$-$C_{20}$alkyl is unsubstituted or substituted by one or more OH or SH; or $R_5$ and $R_6$ independently of each other are $C_2$-$C_{12}$alkenyl, $C_3$-$C_{20}$cycloalkyl or $C_6$-$C_{20}$aryl; or $R_5$ and $R_6$ together with the N-atom to which they are attached form a 5- or 6-membered saturated or unsaturated ring which is uninterrupted or interrupted by O or $NR_{5a}$.

Or $R_5$ and $R_6$ independently of each other are hydrogen, $C_1$-$C_{20}$alkyl which is unsubstituted or substituted by one or more halogen, $OR_{3a}$, $SR_{4a}$, $(CO)OR_{3a}$, $C_3$-$C_8$cycloalkyl or $C_6$-$C_{20}$aryl; or $R_5$ and $R_6$ independently of each other are $C_2$-$C_{20}$alkyl interrupted by one or more O, $C_2$-$C_{12}$alkenyl, $C_3$-$C_{20}$cycloalkyl or $C_6$-$C_{20}$aryl; or $R_5$ and $R_6$ together with the N-atom to which they are attached form a 5- or 6-membered saturated or unsaturated ring which is uninterrupted or interrupted by O or $NR_{5a}$.

Or $R_5$ and $R_6$ independently of each other are hydrogen, $C_1$-$C_{20}$alkyl, $C_2$-$C_{20}$alkyl interrupted by one or more O, $C_3$-$C_{20}$cycloalkyl or $C_6$-$C_{20}$aryl;

or $R_5$ and $R_6$ together with the N-atom to which they are attached form a 5- or 6-membered saturated or unsaturated ring which is uninterrupted or interrupted by O or $NR_{5a}$.

Or $R_5$ and $R_6$ independently of each other are hydrogen, $C_1$-$C_{20}$alkyl, $C_2$-$C_{20}$alkyl interrupted by one or more O, in particular $C_1$-$C_{20}$alkyl.

$R_{5a}$ and $R_{6a}$ for example independently of each other are hydrogen, $C_1$-$C_{20}$alkyl, $C_2$-$C_{12}$alkenyl, $C_3$-$C_8$cycloalkyl, $C_6$-$C_{20}$aryl, $C_1$-$C_{20}$alkoxy;

or $R_{5a}$ and $R_{6a}$ together with the N-atom to which they are attached form a 5- or 6-membered saturated or unsaturated ring which is uninterrupted or interrupted by O.

Or $R_{5a}$ and $R_{6a}$ for example independently of each other are hydrogen, $C_1$-$C_{20}$alkyl or $C_3$-$C_8$cycloalkyl, in particular $C_1$-$C_{20}$alkyl.

$R_7$, $R_8$, $R_9$, $R_{10}$ and $R_{11}$ for example independently of each other are hydrogen, $C_1$-$C_{20}$alkyl, $OR_3$, $SR_4$, $NR_5R_6$, $COOR_3$, $(CO)R_{1a}$;

or $R_7$, $R_8$, $R_9$, $R_{10}$ and $R_{11}$ independently of each other are $C_1$-$C_{20}$alkyl substituted by one or more halogen, $OR_3$, $SR_4$, $NR_5R_6$, $(CO)OR_3$, $C_3$-$C_8$cycloalkyl which is uninterrupted or interrupted by one or more O or $C_6$-$C_{20}$aroyl;

or $R_7$, $R_8$, $R_9$, $R_{10}$ and $R_{11}$ independently of each other are $C_2$-$C_{20}$alkyl interrupted by one or more O;

or $R_7$, $R_8$, $R_9$, $R_{10}$ and $R_{11}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $OR_3$, $SR_4$, $NR_5R_6$, $COOR_3$, $(CO)R_{1a}$ or

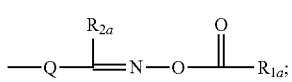

or $R_8$ and $R_9$, $R_9$ and $R_{10}$, or $R_{10}$ and $R_{11}$ are

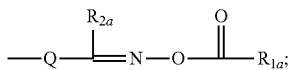

Or $R_7$, $R_8$, $R_9$, $R_{10}$ and $R_{11}$ for example independently of each other are hydrogen, $C_1$-$C_{20}$alkyl, $OR_3$, $SR_4$, $NR_5R_6$, $COOR_3$, $(CO)R_{1a}$;

or $R_7$, $R_8$, $R_9$, $R_{10}$ and $R_{11}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $OR_3$, $SR_4$, $NR_5R_6$, $COOR_3$, $(CO)R_{1a}$ or

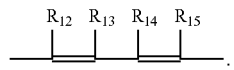

or $R_8$ and $R_9$, $R_9$ and $R_{10}$, or $R_{10}$ and $R_{11}$ are

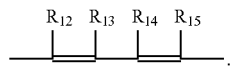

Or $R_7$, $R_8$, $R_9$, $R_{10}$ and $R_{11}$ for example independently of each other are hydrogen, $C_1$-$C_{20}$alkyl, $OR_3$, $COOR_3$, $(CO)R_{1a}$, $C_6$-$C_{20}$aryl or $C_3$-$C_{20}$heteroaryl; or $R_8$ and $R_9$, $R_9$ and $R_{10}$, or $R_{10}$ and $R_{11}$ are

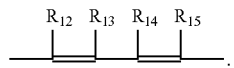

Or $R_7$, $R_8$, $R_9$, $R_{10}$ and $R_{11}$ for example independently of each other are hydrogen, $C_1$-$C_{20}$alkyl or $(CO)R_{1a}$; or $R_8$ and $R_9$ are

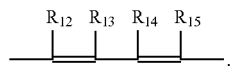

in particular hydrogen or $(CO)R_{1a}$ or $R_8$ and $R_9$ are

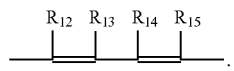

$R_{12}$, $R_{13}$, $R_{14}$ and $R_{15}$ for example independently of each other are hydrogen or $C_1$-$C_{20}$alkyl, in particular hydrogen.

$R_{16}$ and $R_{17}$ for example independently of each other are hydrogen or $C_1$-$C_{20}$alkyl, in particular hydrogen.

The compounds of the formula I and II are suitable as radical photoinitiators. Accordingly, subject of the invention is the use of a compound of the formula I or II as defined above for the photopolymerization of a composition comprising at least one ethylenically unsaturated photopolymerizable compound.

Another subject of the present invention therefore is a photopolymerizable composition comprising
(a) at least one ethylenically unsaturated photopolymerizable compound and
(b) as photoinitiator, at least one compound of the formula I or II as defined above.

The composition may comprise additionally to the photoinitiator (b) at least one further photoinitiator (c), and/or other additives (d).

The composition may comprise additionally to the photoinitiator (b) at least one further photoinitiator (c) or other additives (d), or both, at least one further photoinitiator (c) and other additives (d).

Other additives (d) for example are one or more components selected from thermal radical initiators, pigments, fillers, dispersants and sensitizers.

Said additives are described in more detail below.

Interesting is a photopolymerizable composition as described above, comprising 0.05 to 25% by weight of the photoinitiator (b), or the photoinitiators (b) and (c), based on the composition.

The unsaturated compounds (a) may include one or more olefinic double bonds. They may be of low (monomeric) or high (oligomeric) molecular mass.

Component (a) for example comprises a resin obtained by the reaction of a saturated or unsaturated polybasic acid anhydride with a product of the reaction of an epoxy resin and an unsaturated monocarboxylic acid.

Subject of the invention accordingly also is a photopolymerizable composition as described above, wherein the component (a) is a resin obtained by the reaction of a saturated or unsaturated polybasic acid anhydride with a product of the reaction of an epoxy resin and an unsaturated monocarboxylic acid.

Component (a) for example comprises an alkaline developable resin.

The polymerizable composition according to the invention preferably comprises the component (a) in an amount of from 2 to 98% by weight, more preferably from 5 to 90% by weight, in particular from 10 to 80% by weight, based on the whole solid contents of the polymerizable composition (i.e. the amount of all components without the solvent(s)).

Preferably, the alkaline developable resin has free carboxylic groups. The acid number is preferably from 50 to 600 mg KOH/g, more preferably 100 to 300 mg KOH/g. The acid numbers stated here are the acid number according to DIN EN 12634.

Examples of alkali developable resins are acrylic polymers having carboxylic acid function as a pendant group, such as copolymers obtained by copolymerizing an ethylenic unsaturated carboxylic acid such as (meth)acrylic acid, 2-carboxyethyl (meth)acrylic acid, 2-carboxypropyl (meth)acrylic acid, itaconic acid, citraconic acid, mesaconic acid, fumaric acid, crotonic acid, maleic acid, maleic anhydride, fumaric anhydride, half-ester of maleic acid, cinnamic acid, mono[2-(meth)acryloyloxyethyl]succinate, mono[2-(meth)acryloyloxyethyl]adipate, mono[2-(meth)acryloyloxyethyl]phthalate, mono[2-(meth)acryloyloxyethyl]hexahydrophthalate, mono[2-(meth)acryloyloxyethyl]maleate, mono[2-(meth)acryloyloxypropyl]succinate, mono[2-(meth)acryloyloxypropyl]adipate, mono[2-(meth)acryloyloxypropyl]phthalate, mono[2-(meth)acryloyloxypropyl]hexahydrophthalate, mono[2-(meth)acryloyloxypropyl]maleate, mono[2-(meth)acryloyloxybutyl]succinate, mono[2-(meth)acryloyloxybutyl]adipate, mono[2-(meth)acryloyloxybutyl]phthalate, mono[2-(meth)acryloyloxybutyl]hexahydrophthalate, mono[2-(meth)acryloyloxybutyl]maleate, 3-(alkylcarbamoyl)acrylic acid, α-chloroacrylic acid, monoesterified maleic acid, and ω-carboxypolycaprolactone mono(meth)acrylate, with one or more monomers selected from esters of (meth)acrylic acid, such as methyl (meth)acrylate, ethyl (meth)acrylate, propyl (meth)acrylate, butyl (meth)acrylate, benzyl (meth)acrylate, 2-ethylhexyl (meth)acrylate, hydroxyethyl (meth)acrylate, hydroxypropyl (meth)acrylate, tetrahydrofurfuryl (meth) acrylate, hydroxybutyl (meth)acrylate, glycerol mono(meth)acrylate, dihydroxypropyl (meth)acrylate, allyl (meth)acrylate, cyclohexyl (meth)acrylate, phenyl (meth)acrylate, methoxyphenyl (meth)acrylate, methoxyethyl (meth)acrylate, phenoxyethyl (meth)acrylate, methoxydiethyleneglycol (meth)acrylate, methoxytriethyleneglycol (meth)acrylate, methoxypropyl (meth)acrylate, methoxydipropyleneglycol (meth)acrylate, (3-trimethoxysilyl)propyl (meth)acrylate, (meth)acrylic acid trimethylsilyl ester, isobornyl meth(acrylate), dicyclopentadienyl (meth)acrylate, 2-hydroxy-3-phenoxypropyl (meth)acrylate, tricyclo[5.2.1.0$^{2,6}$]decan-8-yl (meth)acrylate, aminoethyl (meth)acrylate, N, N-dimethylaminoethyl (meth)acrylate, aminopropyl (meth)acrylate, N, N-dimethylaminopropyl (meth)acrylate, glycidyl (meth) acrylate, 2-methylglycidyl (meth)acrylate, 3,4-epoxybutyl (meth)acrylate, 6,7-epoxyheptyl (meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methystyrene, dimethoxystyrene, vinylbenzyl methyl ether, vinylbenzyl glycidyl ether, indene, 1-methylindene; 1-ethenyl-4-silylbenzen, 1-ethenyl-4-trimethylsilylbenzene, t-buthyl dimethylsilyl p-vinyl phenyl ester; amide type unsaturated compounds, such as (meth)acrylamide, diacetone acrylamide, N-methylolacrylamide, N-butoxymethacrylamide, N,N-dimethyl (meth)acrylamide, N,N-diethyl (meth)acrylamide, N,N-dibutyl (meth)acrylamide, N,N-diethylhexyl (meth)acrylamide, N,N-dicyclohexyl (meth)acrylamide, N,N-diphenyl (meth)acrylamide, N-methyl-N-phenyl (meth)acrylamide, N-hydroxyethyl-N-methyl (meth)acrylamide, N-methyl (meth)acrylamide, N-ethyl (meth)acrylamide, N-propyl (meth)acrylamide, N-butyl (meth)acrylamide, N-hydroxyethyl (meth)acrylamide, N-heptyl (meth)acrylamide, N-octyl (meth)acrylamide, N-ethyhexyl (meth)acrylamide, N-hydroxyethyl (meth) acrylamidecyclohexyl, N-benzyl (meth)acrylamide, N-phenyl (meth)acrylamide, N-tolyl (meth)acrylamide, N-hydroxyphenyl (meth)acrylamide, N-naphthyl (meth) acrylamide, N-phenylsulfonyl (meth)acrylamide, N-methylphenylsulfonyl (meth)acrylamide and N(meth) acryloylmorpholine; acetal ester or ketal ester compounds, such as norbornene, 2,3-bis(trimethylsilyloxycarbonyl)-5-norbornene, 2,3-bis(triethylsilyloxycarbonyl)-5-norbornene, 2,3-bis(t-butyldimethylsilyloxycarbonyl)-5-norbornene, 2,3-bis(trimethylgermyloxycarbonyl)-5-norbornene, 2,3-bis(triethylgermyloxycarbonyl)-5-norbornene, 2,3-bis(t-butyldimethylgermyloxycarbonyl)-5-norbornene, 2,3-bis(t-butyloxycarbonyl)-5-norbornene, 2,3-bis(benzyloxycarbonryl)-5-norbornene, 2,3-bis(tetrahydrofurane-2-yloxycarbonyl)-5-norbornene, 2,3-bis(cyclopentyloxycarbonyl)-5-norbornene, 2,3-bis(cyclohexyloxycarbonyl)-5-norbornene, 2,3-bis(cycloheptyloxycarbonyl)-5-norbornene, 2,3-bis(1-methoxyethoxycarbonyl)-5-norbornene, 2,3-bis(1-t-butoxyethoxycarbonyl)-5-norbornene, 2,3-bis(1-benzyloxyethoxycarbonyl)-5-norbornene, 2,3-bis[(cyclohexyl)(ethoxy)methoxycarbonyl]-5-norbornene, 2,3-bis(1-methyl-1-methoxyethoxycarbonyl)-5-norbornene, 2,3-bis(1-methyl-1-i-butoxyethoxycarbonyl)-5-norbornene, 2,3-bis[(benzyl)(ethoxy)methoxycarbonyl]-5-norbornene; 1-alkylcycloalkylester compounds, such as 1-metylcyclopropyl (meth)acrylate, 1-methylcyclobutyl (meth)acrylate, 1-methylcyclopentyl (meth)acrylate, 1-methylcyclohexyl (meth)acrylate, 1-methylcycloheptyl (meth)acrylate, 1-methylcyclooctyl (meth)acrylate, 1-methylcyclononyl (meth)acrylate, 1-ethylcyclodecyl (meth)acrylate, 1-ethylcyclopropyl (meth)acrylate, 1-ethylcyclobutyl (meth)acrylate, 1-ethylcyclopentyl (meth)acrylate, 1-ethylcyclohexyl (meth)acrylate, 1-ethylcycloheptyl (meth)acrylate, 1-ethylcyclooctyl (meth)acrylate, 1-ethylcyclononyl (meth)acrylate, 1-ethylcyclodecyl (meth)acrylate, 1-i-propylcyclopropyl (meth)acrylate, 1-i-propylcyclopentyl (meth)acrylate, 1-i-propylcyclohexyl (meth)acrylate, 1-i-propylcycloheptyl (meth)acrylate, 1-i-propylcyclooctyl (meth)acrylate, 1-i-propylcyclononyl (meth)acrylate, 1-i-propylcyclodecyl (meth)acrylate, 1-i-butylcyclopropyl (meth)acrylate, 1-i-butylcyclobutyl (meth)acrylate, 1-i-butylcyclopentyl (meth) acrylate, 1-i-butylcyclohexyl (meth)acrylate, 1-i-butylcyclooctyl (meth)acrylate, 1-i-butylcyclononyl (meth)acrylate, 1-i-butylcyclodecyl (meth)acrylate, 1-i-pentylcyclopropyl (meth)acrylate, 1-i-pentylcyclopentyl (meth)acrylate, 1-i-pentylcyclohexyl (meth)acrylate, 1-i-pentylcycloheptanyl (meth)acrylate, 1-i-pentylcyclooctyl (meth)acrylate, 1-i- pentylcyclononyl (meth)acrylate, 1-i-pentylcyclodecyl (meth)acrylate, 1-i-octylcyclopropyl (meth)acrylate, 1-i-octylcyclobutyl (meth)acrylate, 1-i-octylcycloheptyl (meth)acrylate, 1-i-octylcyclooctyl (meth)acrylate, 1-i-octylcyclononyl (meth)acrylate, 1-i-octylcyclodecyl (meth)acrylate; methacryl acids, such as 3-(methacryloyloxymethyl)oxetane, 3-(methacryloyloxymethyl)-3-ethyloxetane, 3-(methacryloyloxymethyl)-2-methyloxetane, 3-(methacryloyloxymethyl)-2-trifluoromethyloxetane, 3-(methacryloyloxyethyl)-2-pentafluoroethyloxetane, 3-(methacryloyloxymethyl)-2-phenyloxetane, 3-(methacryloyloxymethyl)-2,2-difluorooxetane, 3-(methacryloyloxymethyl)-2,2,4,-trifluorooxetane, 3-(methacryloyloxymethyl)-2,2,4,4-tetrafluorooxetane, 3-(methacryloyloxyethyl)oxetane, 3-(methacryloyloxyethyl)-3-ethyloxetane, 2-ethyl-3-(methacryloyloxyethyl)oxetane, 3-(methacryloyloxyethyl)-2-trifluoromethyloxetane, 3-(methacryloyloxyethyl)-2-pentafluoroethyloxetane, 3-(methacryloyloxyethyl)-2-phenyloxetane, 2,2-difluoro-3-(methacryloyloxyethyl)oxetane, 3-(methacryloyloxyethyl)-2,2,4-trifluorooxetane, 3-(methacryloyloxyethyl)-2,2,4,4,-tetrafluorooxetane; polycyclic compounds or anhydride, such as 5-carboxybicyclo[2.2.1]hept-2-ene, 5,6-dicarboxybicyclo[2.2.1]hept-2-ene, 5-carboxy-5-methylbicyclo[2.2.1]hept-2-ene, 5-carboxy-6-ethylbicyclo[2.2.1]hept-2-ene, 5-carboxy-6-methylbicyclo[2.2.1]hept-2-ene, 5-carboxy-6-ethylbicyclo[2.2.1]hept-2-ene, 5,6-dicarboxybicyclo[2.2.1]hept-2-ene anhydride; vinyl or allyl esters, such as vinyl acetate, vinyl propionate, vinyl butylate, vinyl pivalate, vinyl benzoate, vinyl trimethylacetate, vinyl diethylacetate, vinyl borate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, vinyl triethoxysilane, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethybutyl ether, vinyl hydroxyethoxyethyl ether, vinyl dimethylaminoethyl ether, vinyl diethylaminoethyl ether, vinyl butylaminoethyl ether, [(ethenyloxy)methyl]triethylsilane, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; crotonates, such as butyl crotonate, hexyl crotonate, glycerine monocrotonate; itaconates, such as dimethyl itaconate, diethyl itaconate, dibutyl itaconate; and maleates or fumarates, such as dimethyl maleate, dibutyl fumarate; polyolefin type compounds, such as butadiene, isoprene, chloroprene and the like; methacrylonitrile, methyl isopropenyl ketone, vinyl acetate, vinyl propionate, vinyl pivalate, maleimide, N-phenylmaleimide, N-methylphenylmaleimide, Nmethoxyphenylmaleimide, N-cyclohexylmaleimide, N-alkylmaleimide, maleic anhydride, polystyrene macromonomer, polymethyl (meth)acrylate macromonomer, polybutyl (meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferable examples of copolymers are copolymers of methyl (meth)acrylate/(meth)acrylic acid, copolymers of benzyl (meth)acrylate/(meth)acrylic acid, copolymers of methyl (meth)acrylate/ethyl (meth)acrylate/(meth)acrylic acid, copolymers of benzyl (meth)acrylate/(meth)acrylic acid/styrene, copolymers of benzyl (meth)acrylate/(meth)acrylic acid/hydroxyethyl (meth)acrylate, copolymers of benzyl (meth)acrylate/(meth)acrylic acid/glycidyl (meth)acrylate, copolymers of benzyl (meth)acrylate/(meth)acrylic acid/3-(methacryloyloxymethyl)oxetane, copolymers of methyl (meth)acrylate/butyl (meth)acrylate/(meth)acrylic acid/styrene, copolymers of methyl (meth)acrylate/benzyl (meth)acrylate/(meth)acrylic acid/hydroxyphenyl (meth)acrylate, copolymers of methyl (meth)acrylate/(meth)acrylic acid/polymethyl (meth)acrylate macromonomer, copolymers of benzyl (meth)acrylate/(meth)acrylic acid/polymethyl (meth)acrylate macromonomer, copolymers of tetrahydrofurfuryl (meth)acrylate/styrene/(meth)acrylic acid, copolymers of methyl (meth)acrylate/(meth)acrylic acid/polystyrene macromonomer, copolymers of benzyl (meth)acrylate/(meth)acrylic acid/polystyrene macromonomer, copolymers of benzyl (meth)acrylate/(meth)acrylic acid/2-hydroxyethyl (meth)acrylate/polystyrene macromonomer, copolymers of benzyl (meth)acrylate/(meth)acrylic acid/2-hydroxypropyl (meth)acrylate/polystyrene macromonomer, copolymers of benzyl (meth)acrylate/(meth)acrylic acid/2-hydroxy-3-phenoxypropyl (meth)acrylate/polymethyl (meth)acrylate macromonomer, copolymers of methyl (meth)acrylate/(meth)acrylic acid/2-hydroxyethyl (meth)acrylate/polystyrene macromonomer, copolymers of benzyl (metha)crylate/(meth)acrylic acid/2-hydroxyethyl (meth)acrylate/polymethyl (meth)acrylate macromonomer, copolymers of N-phenylmaleimide/benzyl (meth)acrylate/(meth)acrylic acid and styrene, copolymers of benzyl (meth)acrylate/(meth)acrylic acid/N-phenylmaleimide/mono-[2-(meth)acryloyloxyethyl]succinate/styrene, copolymers of allyl (meth)acrylate/(meth)acrylic acid/N-phenylmaleimide/mono-[2-(meth)acryloyloxyethyl]succinate/styrene, copolymers of benzyl (meth)acrylate/(meth)acrylic acid/N-phenylmaleimide/glycerol mono(meth)acrylate/styrene, copolymers of benzyl (meth)acrylate/ω-carboxypolycaprolactone mono(meth)acrylate/(meth)acrylic acid/N-phenylmaleimide/glycerol mono(meth)acrylate/styrene, and copolymers of benzyl (meth)acrylate/(meth)acrylic acid/N-cyclohexylmaleimide/styrene. Example of commercial product is Ripoxy SPC-2000 provided by Showa Denko K.K. The term "(meth)acrylate" in the context of the present application is meant to refer to the acrylate as well as to the corresponding methacrylate.

One or more monomers selected from the group consisting of silicon containing monomers such as silanes, such as tetraethylorthosilicate or tetraethoxysilane or chloro- or alkoxy functional silanes, olefins such as ethylene, propylene, styrene, vinylpyrrolidone, oxygen- or nitrogen-containing monomers such as acrylic derivatives, e.g. acrylic ester and acrylic acid, methacrylic acid and -ester, urethanes, mono- and di-functional alcohols, carboxylic acids, amines, isocyanates, epoxides, aromatic compounds such as aromatics carrying substituents such as alkyl groups and sulfonated aromatics, aromatic resins, imidazole and imidazole derivatives, pyrazoles, quartenary ammonium compounds, polyurethane prepolymers and epoxy resins.

The functional groups in the compound, which result in good alkaline solubility, are preferably carboxylic groups. However, also other groups, which result in alkaline solubility, are possible. Examples for such groups are phenolic groups, sulfonic acid groups and anhydride groups.

When the number of ethylenically unsaturated bonds, which are present in the molecular unit of the resin curable by the activated energy ray, is small, it is possible to use bis-phenol A type epoxy compounds to lower the viscosity of the ink.

The novolak type epoxy compounds are represented by phenol novolak type epoxy resins and cresol novolak type epoxy resins. Such compounds are typically produced by reacting epichlorohydrin with a novolak resin.

Typical examples of the aforementioned acid anhydride are dibasic acid anhydrides such as for example maleic anhydride, succinic anhydride, itaconic anhydride, phthalic anhydride, tetrahydrophthalic anhydride, hexahydrophthalic anhydride, methylhexahydrophthalic anhydride, endo-methylenetetrahydrophthalic anhydride, methyl-endomethylenetetrahydrophthalic anhydride, chlorendic anhydride, and methyltetrahydrophthalic anhydride; aromatic polycarboxylic anhydrides such as for example trimellitic anhydride, pyromellitic anhydride and benzophenone-tetracarboxylic dianhydride: and polycarboxylic anhydride derivatives such as 5-(2,5-dioxotetrahydrofuryl)-3-methyl-3-cyclohexene-1,2-dicarboxylic anhydride.

Further examples of alkaline developable resins (a) are polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid (for example, EB9696 from UCB Chemicals; KAYARAD TCR1025 from Nippon Kayaku Co. Ltd.; NK OLIGO EA-6340, EA-7440 from Shin-Nakamura Chemical Co., Ltd.). Other examples of such binders are described in JP2002-206014A, JP2004-69754A, JP2004-302245A, JP2005-77451A, JP2005-316449A, JP2005-338328A and JP3754065B2.

Further examples of alkaline developable resins are the above-mentioned polymers or oligomers having at least one ethylenically unsaturated groups.

Further examples are reaction products obtained by adding an epoxy group containing unsaturated compound to a part of the carboxyl groups of a carboxylic acid group containing polymer (for ex., ACA200, ACA200M, ACA210P, ACA230AA, ACA250, ACA300, ACA320 from Daicel Co. and Ripoxy SPC-1000 provided by Showa Denko K. K.). As the carboxylic acid containing polymer, the abovementioned binder polymers which are resulting from the reaction of an unsaturated carboxylic acid compound with one or more polymerizable compounds, for example, copolymers of (meth)acrylic acid, benzyl (meth)acrylate, styrene and 2-hydroxyethyl (meth)acrylate, copolymers of (meth)acrylic acid, styrene and α-methylstyrene, copolymers of (meth)acrylic acid, N-phenylmaleimide, styrene and benzyl (meth)acrylate, copolymers of (meth)acrylic acid and styrene, copolymers of (meth)acrylic acid and benzyl (meth)acrylate, copolymers of tetrahydrofurfuryl (meth)acrylate, styrene and (meth)acrylic acid and the like. Examples of the unsaturated compounds having an epoxy group are given below in the formula (V-1)-(V-15);

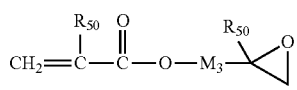
(V-1)

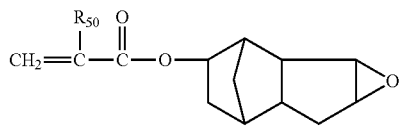
(V-2)

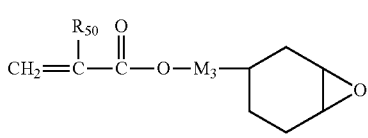
(V-3)

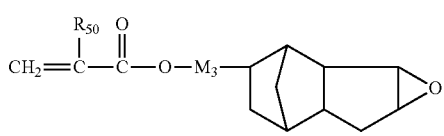
(V-4)

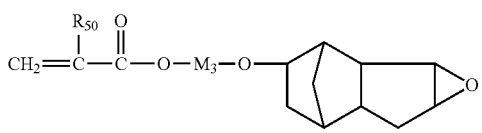
(V-5)

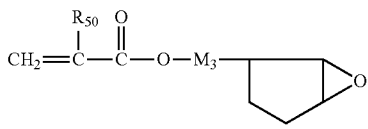
(V-6)

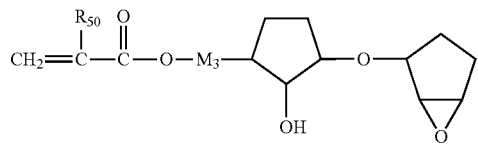
(V-7)

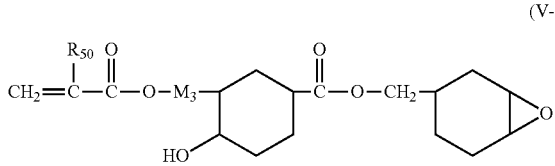
(V-8)

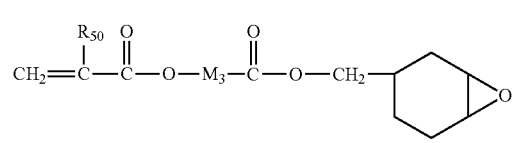
(V-9)

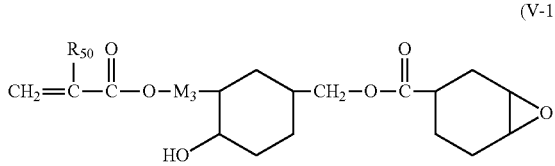
(V-10)

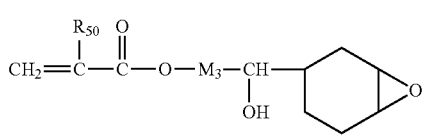
(V-11)

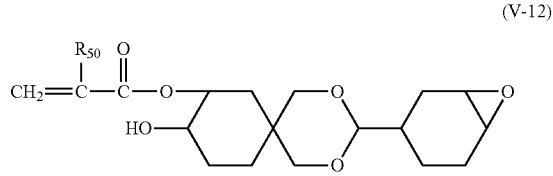
(V-12)

-continued

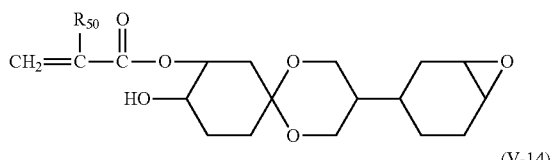
(V-13)

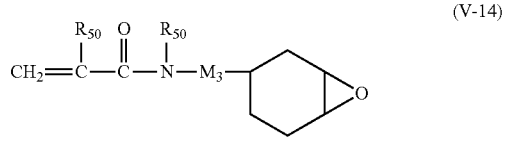
(V-14)

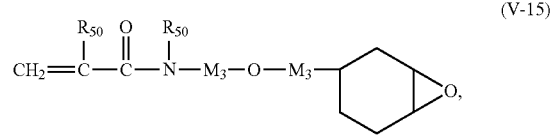
(V-15)

wherein $R_{50}$ is hydrogen or methyl group, $M_3$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methylstyrene and acrylic acid or a copolymer of methyl methacrylate and acrylic acid with 3,4-epoxycyclohexylmethyl (meth)acrylate.

Other examples are products obtained by addition reaction of an epoxy group containing unsaturated compounds to a part of or all of the carboxyl groups of a carboxylic acid group containing polymers followed by further reaction with polybasic acid anhydride (for ex., Ripoxy SPC-3000 provided by Showa Denko K.K.).

Unsaturated compounds having a hydroxy group such as 2-hydroxyethyl (meth)acrylate and glycerol mono(meth)acrylate can be used instead of the above-mentioned epoxy group containing unsaturated compounds as the reactant for carboxylic acid group containing polymers.

Other examples are half esters of anhydride containing polymers, for example reaction products of a copolymer of maleic anhydride and one or more other polymerizable compounds with (meth)acrylates having an alcoholic hydroxyl group such as 2-hydroxyethyl (meth)acrylate or having an epoxy group for example such as the compounds described in the formula (V-1)-(V-15).

Reaction products of polymers having alcoholic hydroxyl groups such as copolymers of 2-hydroxyethyl (meth)acrylate, (meth)acrylic acid, benzyl (meth)acylate and styrene, with (meth)acrylic acid or (meth)acryl chloride can also be used.

Other examples are reaction products of polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy groups containing (meth)acrylic compounds to all of the carboxyl groups of a carboxylic acid containing polymer as mentioned above.

Another example is polyimide resin having ethylenically unsaturated groups and at least one carboxyl function. The polyimide binder resin in the present invention can be a polyimide precursor, for example, a poly(amic acid).

Specific examples of alkaline developable resins are:

Acrylpolymer type resins such as

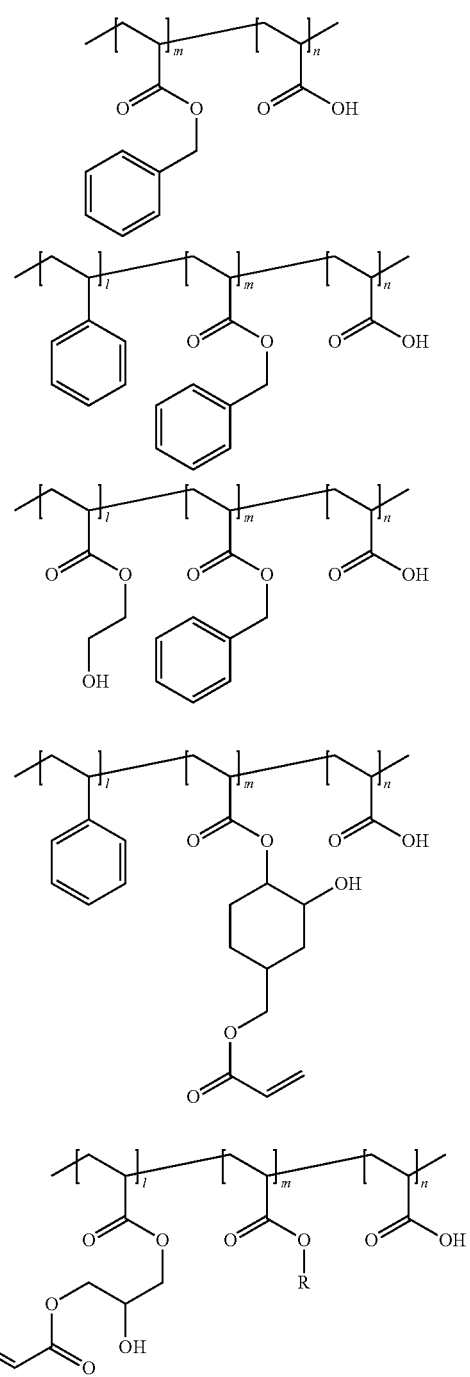

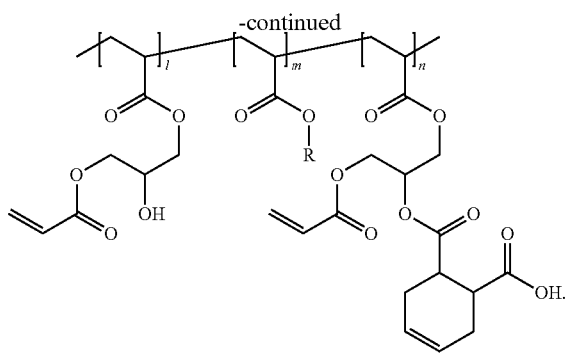

Cardo type resin (fluorene epoxy acrylate based resin)

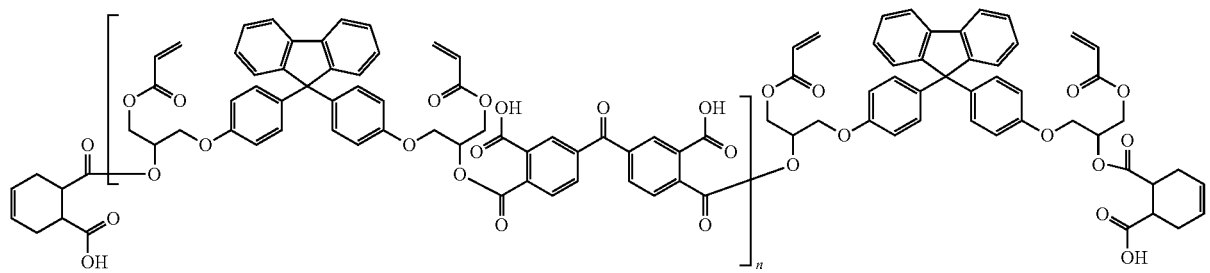

For example, a content of the binder resin may be 2-98%, preferably 5-90% and especially 10-80% by weight based on a total weight of the solid contents in the radically polymerizable composition.

Component (a) for example comprises an acrylate monomer.

The acrylate monomer refers to an acrylate monomer or oligomer that contains one or more acryloyl or methacryloyl moieties or combinations thereof.

Examples of compounds containing a double bond are (meth)acrylic acid, alkyl, hydroxyalkyl or aminoalkyl (meth)acrylates, for example methyl, ethyl, n-butyl, i-butyl, t-butyl, n-propyl, i-propyl, n-hexyl, cyclohexyl, 2-ethylhexyl, isobornyl, benzyl, 2-hydroxyethyl, 2-hydroxypropyl, methoxyethyl, ethoxyethyl, glycerol, phenoxyethyl, methoxydiethylene glycol, ethoxydiethylene glycol, polyethylene glycol, polypropylene glycol, glycidyl, N,N-dimethylaminoethyl, and N,N-diethylaminoethyl (meth)acrylates. Other examples are (meth)acrylonitrile, (meth)acrylamide, N-substituted (meth)acrylamides such as N,N-dimethyl (meth)acrylamide, N,N-diethyl (meth)acrylamide, N,N-dibutyl (meth)acrylamide, N-methyl (meth)acrylamide, N-ethyl (meth)acrylamide, N-butyl (meth)acrylamide, and N-(meth)acryloylmorpholine, vinyl esters such as vinyl acetate, vinyl ethers such as i-butyl vinyl ether, styrene, alkyl-, hydroxy- and halostyrenes, N-vinylpyrrolidone, N-vinylcaprolactam, N-vinyl acetoamide, N-vinyl formamide, vinyl chloride and vinylidene chloride.

Examples of polyunsaturated compounds of relatively high molecular mass (oligomers) are polyesters, polyurethanes, polyethers and polyamides, which contain ethylenically unsaturated carboxylates.

Particularly suitable examples are esters of an ethylenically unsaturated carboxylic acid with a polyol or polyepoxide.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acids are preferred.

Suitable polyols are aromatic, in particular, aliphatic and cycloaliphatic polyols. Examples of aromatic polyols are hydroquinone, 4,4'-dihydroxybiphenyl, 2,2-bis(4-hydroxyphenyl)ethane, 2,2-bis(4-hydroxyphenyl)propane, 2,2-bis(4-hydroxyphenyl)hexafluoropropane, 9,9-bis(4-hydroxyphenyl)fluorene, novolacs and resols. Examples of aliphatic and cycloaliphatic polyols are alkylenediols having preferably 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, triethanolamine, trimethylolethane, trimethylolpropane, pentaerythritol, pentaerythritol monooxalate, dipentaerythritol, ethers of pentaerythritol with ethylene glycol or propylene glycol, ethers of dipentaerythritol with ethylene glycol or propylene glycol, sorbitol, 2,2-bis[4-(2-hydroxyethoxy)phenyl]methane, 2,2-bis[4-(2-hydroxyethoxy)phenyl]propane and 9,9-bis[4-(2-hydroxyethoxy)phenyl]fluorene. Other suitable polyols are polymers and copolymers containing hydroxyl groups in the polymer chain or in side groups, examples being homopolymers or copolymers comprising vinyl alcohol or comprising hydroxyalkyl (meth)acrylates. Further polyols which are suitable are esters and urethanes having hydroxyl end groups.

The polyols may be partially or completely esterified with one unsaturated carboxylic acid or with different unsaturated carboxylic acids, and in partial esters the free hydroxyl groups may be modified, for example etherified or esterified with other carboxylic acids.

Examples of esters based on polyols are trimethylolpropane tri(meth)acrylate, trimethylolpropane tri(acryloyloxypropyl) ether, trimethylolethane tri(meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl) ether, tri pentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth) acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

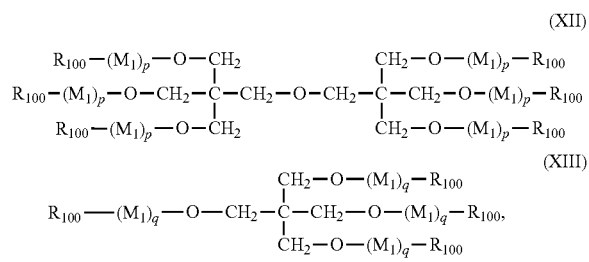

wherein
$M_1$ is —($CH_2CH_2O$)— or —[$CH_2CH(CH_3)O$]—,
$R_{100}$ is —$COCH=CH_2$ or —$COC(CH_3)=CH_2$,
p is 0 to 6 (total of p: 3-24), and q is 0 to 6 (total of q: 2-16).

Examples of polyepoxides are those based on the above-mentioned polyols and epichlorohydrin. Typical examples are bis(4-glycidyloxyphenyl)methane, 2,2-bis(4-glycidyloxyphenyl)propane, 2,2-bis(4-glycidyloxyphenyl) hexafluoropropane, 9,9-bis(4-glycidyloxyphenyl)fluorene, bis[4-(2-glycidyloxyethoxy)phenyl]methane, 2,2-bis[4-(2-glycidyloxyethoxy)phenyl]propane, 2,2-bis[4-(2-glycidyloxyethoxy)phenyl]hexafluoropropane, 9,9-bis[4-(2-glycidyloxyethoxy)phenyl]fluorene, bis[4-(2-glycidyloxypropoxy)phenyl]methane, 2,2-bis[4-(2-glycidyloxypropoxy)phenyl]propane, 2,2-bis[4-(2-glycidyloxypropoxy)phenyl]hexafluoropropane, 9,9-bis[4-(2-glycidyloxypropoxy)phenyl]fluorene, glycerol diglycidyl ether and glycidyl ethers of phenol and cresol novolacs.

Typical examples based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryloxy)propoxyethoxy}phenyl]fluorene, glycerol 1,3-diglycerolate diacrylate and reaction products of epoxy resins based on novolacs with (meth)acrylic acid.

Preferred multifunctional (meth)acrylate monomers or oligomers include pentaerythritol tetraacrylate, dipentaerythritol pentaacrylate, dipentaerythritol hexaacrylate, ditrimethylolpropane tetraacrylate, pentaerythritol triacrylate, tris(2-hydroxy ethyl) isocyanurate triacrylate.

Specific examples are:
Dipentaerythritol-hexaacrylate (DPHA). Dipentaerythritol-pentaacrylate (DPPA)

Examples of commercially available acrylate monomer or oligomers having two acryloyl or methacryloyl moieties are Aronix®M-210, Aronix®M-240, Aronix®M-6200 (TOAGOSEI Co., LDT.) KAYARAD HDDA, KAYARAD HX-220, KAYARAD HX-620, KAYARAD R-526, KAYARAD UX-2201, KAYARAD MU-2100 (NIPPON KAYAKU Co., LTD.), VISCOAT-260, VISCOAT-355HP (OSAKA ORGANIC CHEMICAL INDUSTRY LTD.).

Examples of commercially available acrylate monomer or oligomers having three or more acryloyl or methacryloyl moieties are Aronix®M-309, Aronix®M-400, Aronix®M-1310, Aronix®M-1960, Aronix®M-7100, Aronix®M-8530, Aronix®TO-1450 (TOAGOSEI Co., LDT.), KAYARAD TMPTA, KAYARAD DPHA, KAYARAD DPCA-20, KAYARAD MAX-3510 (NIPPON KAYAKU Co., LTD.), VISCOAT-295, VISCOAT-300, VISCOAT-GPT, VISCOAT-3PA, VISCOAT-400 (OSAKA ORGANIC CHEMICAL INDUSTRY LTD.).

Examples of commercially available urethane acrylate monomer or oligomers having two or more acryloyl or methacryloyl moieties are NEW FRONTIER R-1150 (DAIICHI KOGYO SEIYAKU CO., LTD.) KAYARAD DPHA-40H, KAYARAD UX-5000 (NIPPON KAYAKU Co., LTD.), UN-9000H (Negami Chemical Industrial Co., Ltd.)

The amount of acrylate present in the radiation curable composition ranges from about 2% to 80% and preferably from about 5% to 70% based on the whole solid contents of the composition, i.e. the amount of all components without the solvent(s).

It is of course possible to add other known photoinitiators (c) to the photocurable composition.

The use of the further photoinitiator is not critical. The photoinitiator (c) is for example selected from benzophenones, bis-imidazole, aromatic α-hydroxyketones, benzylketals, aromatic α-aminoketones, phenylglyoxalic acid esters, mono-acylphosphinoxides, bisacylphosphinoxides, tris-acylphosphinoxides, oximesters derived from aromatic ketones and/or oxime esters of the carbazol type.

Examples of such photoinitiators are camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone, 4,4'-bis(chloromethyl)benzophenone, 4-chlorobenzophenone, 4-phenylbenzophenone, 3,3'-dimethyl-4-methoxy-benzophenone, [4-(4-methylphenylthio) phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone, thioxanthones, thioxanthone derivatives, polymeric thioxanthones as for example OMNIPOL TX; ketal compounds, as for example benzildimethylketal (Irgacure® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (Darocure®1173), 1-hydroxy-cyclohexyl-phenylketone (Irgacure®184), 1-(4-dodecylbenzoyl)-1-hydroxy-1-methyl-ethane, 1-(4-i-propylbenzoyl)-1-hydroxy-1-methyl-ethane, 1-[4-(2-hydroxyethoxy)-phenyl]-2-hydroxy-2-methyl-1-propan-1-one (Irgacure®2959); 2-hydroxy-1-{4-[4-(2-hydroxy-2-methyl-propionyl)-benzyl]-phenyl}-2-methyl-propan-1-one (Irgacure®127); 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane (Irgacure® 907), (2-Benzyl-2-(dimethylamino)-1-[4-(4-morpholinyl)phenyl]-1-butanone) (Irgacure® 369), 2-(4-methylbenzyl)-2-(dimethylamino)-1-[4-(4-morpholinyl)phenyl]-1-butanone (Irgacure® 379), (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzyl ketals, e.g. dimethyl benzyl ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)propoxy]-ethyl ester (Irgacure® 754); ketosulfones, e.g. ESACURE KIP 1001 M; oximeesters, e.g. 1,2-octane-dione 1-[4-(phenylthio)phenyl]-2-(O-benzoyloxime), etha-none 1-[9-ethyl-6-(2-methylbenzoyl)-9H-carbazol-3-yl]-1-(O-acetyloxime), methanone [8-[[(acetyloxy)imino][2-(2,2,3,3-tetrafluoropropoxy)phenyl]methyl]-11-(2-ethylhexyl)-11H-benzo[a]carbazol-5-yl](2,4,6-trimethylphenyl), ethanone 1-[9-ethyl-6-(2-methyl-4-(2,2-di methyl-1, 3-dioxolanyl)methoxybenzoyl)-9H-carbazol-3-yl]-1-(O-acetyloxime), N-acetoxy-N-{3-[9-ethyl-6-(naphthalene-1-carbonyl)-9H-carbazol-3-yl]-1-methyl-3-acetoxyimino-propyl}-acetamide, 9H-thioxanthene-2-carboxaldehyde 9-oxo-2-(O-acetyloxime), [(E)-[1-(cyclohexylmethyl)-2-oxo-2-(4-phenylsulfanylphenyl)ethylidene]amino] cyclopropanecarboxylate), [(E)-[1-(cyclohexylmethyl)-2-oxo-2-(4-phenylsulfanylphenyl)ethylidene]amino]acetate, [(E)-[1-(cyclohexylmethyl)-2-[9-ethyl-6-(thiophene-2-carbonyl)carbazol-3-yl]-2-oxo-ethylidene]amino]acetate, [(E)-[1-(o-tolyl)-2-oxo-2-(4-phenylsulfanylphenyl)ethylidene] amino]acetate, [(E)-1-[9-ethyl-6-(thiophene-2-carbonyl) carbazol-3-yl]ethylideneamino]acetate, [(E)-1-[9-ethyl-6-(thiophene-2-carbonyl)carbazol-3-yl]propylideneamino] acetate, oxime esters described in WO07/062963, WO07/071797, WO07/071497, WO05/080337, JP2010-049238, WO2008078678, JP2010-15025 and JP2010-49238, peresters, e,g. benzophenone tetracarboxylic peresters as described for example in EP 126541, monoacyl phosphine oxides, e.g. (2,4,6-trimethylbenzoyl)diphenylphosphine oxide (Irgacure® TPO), ethyl (2,4,6 trimethylbenzoyl phenyl) phosphinic acid ester; bisacylphosphine oxides, e.g. bis(2,6-dimethoxybenzoyl)-(2,4,4-trimethyl-pentyl)phosphine oxide, bis(2,4,6-trimethylbenzoyl)phenylphosphine oxide (Irgacure® 819), bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl[1,3,5]triazine, 2-methyl-4,6-bis-trichloromethyl-[1,3,5]triazine, hexaaryl-bisimidazole/coinitiators systems, e.g. ortho-chlorohexaphenyl-bisimidazole combined with 2-mercaptobenzothiazole, ferrocenium compounds, or titanocenes, e.g. bis(cyclopentadienyl)-bis(2,6-difluoro-3-pyrryl-phenyl) titanium (Irgacure®784). Further, borate compounds can be used as coinitiators. As additional photoinitiators oligomeric compounds such as for example oligomeric alpha hydroxyl ketones, e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP provided by Fratelli Lamberti, or oligomeric alpha amino ketones may be employed as well.

Specific examples are:

(2-Benzyl-2-(dimethylamino)-1-[4-(4-morpholinyl)phenyl]-1-butanone), 2-(4-methylbenzyl)-2-(dimethylamino)-1-[4-(4-morpholinyl)phenyl]-1-butanone, 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime).

The composition according to the invention may comprise as component (d) a colorant. As colorant pigments or dyes or mixtures of pigment(s) and dye(s) may be present in the composition. The pigments which can be comprised in the composition according to the present invention, including a pigmented color filter resist composition, are preferably processed pigments.

The red pigment comprises, for example, an anthraquinone type pigment alone, a diketopyrolopyrole type pigment alone, a mixture of them or a mixture consisting of at least one of them and a disazo type yellow pigment or an isoindoline type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177, C. I. Pigment Red 242 and C. I. Pigment Red 254, and C. I. Pigment Yellow 83 or C. I. Pigment Yellow 139 ("C.I." refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 222, 244, 255, 264, 272 and C.I. Pigment Yellow 12, 13, 14, 17, 20, 24, 31, 53, 55, 93, 95, 109, 110, 128, 129, 138, 139, 150, 153, 154,155, 166, 168, 185, 199, 213 and C.I. Pigment Orange 43 and 71.

Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes.

The green pigment comprises for instance a halogenated phthalocyanine type pigment alone or its mixture with a bisazo type yellow pigment, an quinophthalone type yellow pigment or a metal complex, in particular C. I. Pigment Green 7 alone, C. I. Pigment Green 36 alone, C.I. Pigment Green 58 alone, or a mixture consisting of at least one member of C. I. Pigment Green 7, C. I. Pigment Green 36, C.I. Pigment Green 58 and C. I. Pigment Yellow 83, C. I. Pigment Yellow 138 or C. I. Pigment Yellow 150. Other suitable green pigments are C.I. Pigment Green 15, 25 and 37.

Examples for suitable green dyes are C. I. Acid Green 3, 9, 16, C. I. Basic Green 1 and 4.

Examples for suitable blue pigments are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60. Other suitable pigments are C. I. Pigment Violet 14,19, 23, 29, 32, 37, 177 and C. I. Orange 73.

The blue dye comprises, for example, a methane type dye, an anthraquinone type dye, an azo type dye, a metal complex azo type dye, a triaryl methane type dye or a phthalocyanine type dye.

Examples for suitable blue dyes are C. I. Solvent Blue 11, 25, 37, 45, 49, 68, 78, 94, C. I. Direct Blue 25, 86, 90, 108, C. I. Acid Blue 1, 3, 7, 9, 15, 83, 90, 103, 104, 158, 161, 249, C. I. Basic Blue 1, 3, 7, 9, 25, 105, and C. I. Disperse Blue 198 and C.I. Mordant Blue 1.

The pigment of the photopolymeric composition for black matrix preferably comprises at least one member selected from the group consisting of carbon black, titanium black, iron oxide, lactone, lactam and perylene. Preferred example is carbon black. However, a mixture of other pigments which, in total, give the black appearance, can also be used. For example, also C. I. Pigment Black 1, 7, 31, 32 and Irgaphor® black S0100(BASF SE) can be used alone or in combination.

Other examples of the dyes used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, 31, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

The pigments in the color filter resist composition have preferably a mean particle diameter smaller than the wavelength of visible light (400 nm to 700 nm). Particularly preferred is a mean pigment diameter of <100 nm.

The concentration of the pigment in the total solid component (pigments of various colors and resin) is for example in the range of 5% to 80% by weight, in particular in the range of 20% to 65% by weight.

The concentration of the dye in the total solid component (dyes of various colors and resin) is for example in the range of 0.5% to 95% by weight, in particular in the range of 0.5% to 70% by weight.

If necessary, the pigments may be stabilized in the photosensitive composition by pretreatment of the pigments with a dispersant to improve the dispersion stability of the pigment in the liquid formulation. Suitable additives are described below.

Additives (d) are optionally present in the composition of the invention, such as dispersing agents, surfactant, adhesion promoters, photosensitizer and the like.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least pigment derivative.

Suitable surfactants include anionic surfactants such as alkylbenzene- or alkylnaphthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOE-ISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to 30 parts by weight, based on 100 parts by weight of the colorant composition.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth)acrylamides, and such block co-polymers and/or comb polymers modified by post modification; polyethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPER-BYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, BASF's EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohols or ethoxylated fatty alcohols, polyols such as aliphatic 1,2-diols or epoxidized soy bean oil, waxes, resin acids and resin acid salts may be used for this purpose.

Suitable pigment derivatives are, for example, copper phthalocyanine derivatives such as BASF's EFKA® 6745, Lubrizol's SOLSPERSE® 5000, 12000, BYK's SYNER-GIST 2100 and azo derivatives such as EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive comprising a dispersant or a mixture of dispersants as well as a photopolymerizable composition as described above as further additive comprising a pigment or a mixture of pigments or a dye or a mixture of dyes or a mixture of one or more pigments with one or more dyes.

In the invention, the content of the dispersing agent is preferably from 1 to 80% by mass, more preferably from 5 to 70% by mass, even more preferably from 10 to 60% by mass, based on the mass of the pigment.

Further suitable additives (d) are for example adhesion improving agents. The curable composition of the invention may contain an adhesion improving agent for increasing adhesion to a hard surface, such as of a support. The adhesion improving agent may be a silane coupling agent, a titanium coupling agent or the like.

Photopolymerization can also be accelerated by adding further photosensitizers or coinitiators (as component (d)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

Specific examples of such compounds are

1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfuryl-thioxanthone, 3,4-di-[2-(2-methoxyethoxy)ethoxycarbonyl]-thioxanthone, 1,3-dimethyl-2-hydroxy-9Hthioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3,-tetramethylbutyl)thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)benzophenone, 4-(4-tolylthio)benzophenone, 1-[4-(4-benzoyl-phenylsulfanyl)-phenyl]-2-methyl-2-(toluene-4-sulfonyl)-propan-1-one, 4-benzoyl-N,N,N-trimethyl benzenemethanaminium chloride, 2-hydroxy-3-(4-benzoyl-phenoxy)-N,N,N-trimethyl-1-propanaminium chloride monohydrate, 4-(13-acryloyl1,4,7,10,13-pentaoxatridecyl)-benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyloylcoumarin, 3-benzoyl-5,7-dimethoxycoumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyloyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP09-179299-A and JP09-325209-A, for example 7-[{4-chloro-6-(diethylamino)-S-triazine-2-yl}amino]-3-phenylcoumarin;

4. 3-(Aroylmethylene)-Thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP08-305019A;

6. Other Compounds acetophenone, 3-methoxyacetophenone, 4-phenylacetophenone, benzil, 4,4'-bis(dimethylamino)benzil, 2-acetyl-naphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate, poly(propylenegylcol)-4-(dimethylamino) benzoate.

A photosensitizer is for example selected from the group consisting of benzophenone and its derivatives, thioxanthone and its derivatives, anthraquinone and its derivatives, or coumarin and its derivatives.

To accelerate the photopolymerization, it is possible to add amines, for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP KokaiHei 6-68309.

To accelerate the polymerization thermally, it is possible to add thermal curing promoter, e.g., oxime sulfonates, as are described, for example, in WO2012/101245, hydroxylamine esters, as are described, for example, in WO2012/108835, in WO2001090113, in WO03029332 and in WO04081100, peroxides, such as organic peroxides or hydroperoxides, as are described, for example, in JP2003015288 and in JP10010718, and azo compounds, are described, for example, in JP2003015288.

The choice of additive(s) is made depending on the field of application and on properties required for this field. The additives described above are customary in the art and accordingly are added in amounts which are usual in the respective application.

Thermal inhibitors (as further additive (d)) are intended to prevent premature polymerization, examples being hydroquinone, hydroquinone derivatives, p-methoxyphenol, β-naphthol or sterically hindered phenols, such as 2,6-di-t-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethylphosphine, triphenyl phosphate or tribenzyl phosphate, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer.

Light stabilizers which can be added in a small quantity are UV absorbers, for example those of the hydroxyphenyl-benzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are
1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphen-yl)benzotriazole, 2-(2'-hydroxy-5'-(1,1,3,3-tetramethyl butyl)phenyl) benzotriazole, 2-(3',5'-di-tert-butyl-2'-hydroxyphenyl)-5-chlorobenzotriazole, 2-(3'-tert-butyl-2'-hydroxy-5'-methylphen-yl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tertamyl-2'-hydroxyphenyl)benzotrhazole, 2-(3',5'-bis-(α,α-dimethylbenzyl)-2'-hydroxy-phenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyl-oxy)carbonylethy-1]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxy-carbonlyethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—$CH_2CH_2$—COO$(CH_2)_3$]$_2$— where R=3'-tert-butyl-4'-hydroxy-5'-2H-benzotri-azol-2-yl-phenyl.

2. 2-Hydroxybenzophenones, for example the 4-hydroxy-, 4-methoxy-, 4-octoxy-, 4-decyloxy, 4-dodecyloxy-, 4-benzyloxy-, 4,2',4'-tri hydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tertbutylbenzoyl)re¬sorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbo-methoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethane-diyl)-bis(3,3,5,5-tetramethyl-piperazinone), 4-benzoyl-2,2,6,6-tetramethylpiperidine, 4-stearyl-oxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetra-methyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropylamino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione and 3-dodecyl-1-(1,2,2,6,6-pentamethyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyloxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethyl-phenyl) 1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethyl¬phenyl)-1,3,5-triazine, 2-[2-hydroxy-4-(2-hydroxy-3-butyloxy-propyloxy)phenyl]-4,6-bis(2,4-dimethyl-phenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phen-yl]-4,6-bis(2,4-dimethyl-phenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phos-phite, distearyl pentaerythrityl diphosphite, tris(2,4-di-tert-butylphenyl) phosphite, diisodecyl pentaerythrityl diphosphite, bis(2,4-di-tert-butylphenyl) pentaerythrityl diphosphite, bis(2,6-di-tert-butyl-4-methylphenyl) pentaerythrityl diphosphite, bis-isodecyloxy pentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbityl triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl) methyl phosphite and bis(2,4-di-tert-butyl-6-methylphenyl) ethyl phosphite.

The composition of the present invention may comprise one or more solvents. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, ethylene glycol monomethyl ether, ethylene glycol monoethyl ether, ethylene glycol monopropyl ether, ethylene glycol monobutyl ether, ethylene glycol dimethyl ether, ethylene glycol diethyl ether, ethylene glycol dipropyl ether, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol dipropyl ether, diethylene glycol monomethyl ether, diethylene glycol monoethyl ether, diethylene glycol dimethyl ether, diethylene glycol diethyl ether, ethylene glycol monomethyl ether acetate, ethylene glycol monoethyl ether acetate, ethylene glycol monopropyl ether acetate, ethylene glycol monobutyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, ethyl acetate, n-butyl acetate, ethyl propionate, propyl propionate, butyl propionate, ethyl 3-ethoxypropionate, methyl 3-methoxypropionate, 2-heptanone, 2-pentanone, and ethyl lactate.

The compositions according to this invention can comprise additionally a crosslinking agent which is activated by an acid or a base, for example as described in JP 10 221843-A, and a compound which generates acid or base thermally or by actinic radiation and which activates a crosslinking reaction. Use is made, in addition to the free-radical hardeners, of cationic photo or thermal initiators such as sulfonium-, phosphonium- or iodonium salts, for example Irgacure®250, Irgacure®270, San-Aid SI series, SI-60L, SI-80L, SI-100L, SI-110L, S1-145, S1-150, S1-160, SI-180L produced by Sanshin Chemical, cyclopentadienyl-arene-iron(II) complex salts, for example ($\eta^6$-isopropylbenzene)($\eta^5$-cyclopentadienyl)iron(II) hexafluorophosphate, as well as oxime sulfonic acid esters, for example described in EP 780729. Also pyridinium and i-quinolinium salts as described e.g. in EP 497531 and EP 441232 may be used in combination with the new photoinitiators. Examples of bases are imidazole and its derivatives for example Curezole OR series and CN series provided by Shikoku Chemicals.

Further the compositions according to the invention may comprise crosslinking agents which can be activated by an acid. The crosslinking agents which can be activated by acid or base include compounds having epoxy or oxetane groups. There may be used a solid or liquid known epoxy or oxetane compound and said compound is used depending on required characteristics. A preferred epoxy resin is a bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; a bisphenol A type epoxy resin such as Epiculon N-3050, N-7050, N-9050 produced by Dainippon Ink & Chemicals Inc., XAC-5005, GT-7004, 6484T, 6099; a bisphenol F type epoxy resin such as YDF-2004, YDF2007 produced by NSCC Epoxy Manufacturing Co., Ltd., etc.; a bisphenol fluorene type epoxy resin such as OGSOL PG, PG-100, EG, EG-210 produced by Osaka Gas Chemicals; a diglycidyl phthalate resin such as Blemmer DGT produced by Nippon Oil and Fats Co., Ltd., etc.; a heterocyclic epoxy resin such as TEPIC produced by Nissan Chemical Industries, Ltd., Araldite PT810 produced by Ciba Specialty Chemicals Inc., etc.; a bixylenol type epoxy resin such as YX-4000 produced by Yuka Shell Co., etc.; a biphenol type epoxy resin such as YL6056 produced by Yuka Shell Co., etc.; a tetraglycidyl xylenoylethane resin such as ZX-1063 produced by NSCC Epoxy Manufacturing Co., Ltd., etc.; a novolak type epoxy resin such as EPPN-201, EOCN-103, EOCN-1020, EOCN-1025 and BRRN produced by Nippon Kayaku Co., Ltd., ECN-278, ECN-292 and ECN-299 produced by Asahi Chemical Industry Co., Ltd., GY-1180, ECN-1273 and ECN-1299 produced by BASF Japan Ltd., YDCN-220L, YDCN-220HH, YDCN-702, YDCN-704, YDPN-601 and YDPN-602 produced by NSCC Epoxy Manufacturing Co., Ltd., Epiculon-673, N-680, N-695, N-770 and N-775 produced by Dainippon Ink & Chemicals Inc., etc.; a novolak type epoxy resin of bisphenol A such as EPX-8001, EPX-8002, EPPX-8060 and EPPX8061 produced by Asahi Chemical Industry Co., Ltd., Epiculon N-880 produced by Dainippon Ink & Chemicals Inc., etc.; a chelate type epoxy resin such as EPX-49-69 and EPX-49-30 produced by Asahi Denka Kogyo K.K., etc.; a glyoxal type epoxy resin such as YDG-414 produced by NSCC Epoxy Manufacturing Co., Ltd., etc.; an amino group-containing epoxy resin such as YH-1402 and ST-110 produced by NSCC Epoxy Manufacturing Co., Ltd., YL-931 and YL-933 produced by Yuka Shell Co., etc.; a rubber-modified epoxy resin such as Epiculon TSR-601 produced by Dainippon Ink & Chemicals Inc., EPX-84-2 and EPX-4061 produced by Asahi Denka Kogyo K.K., etc.; a dicyclopentadiene phenolic type epoxy resin such as DCE-400 produced by Sanyo-Kokusaku Pulp Co., Ltd., etc.; a silicone-modified epoxy resin such as X-1359 produced by Asahi Denka Kogyo K.K., etc.; an e-caprolactone-modified epoxy resin such as Plaque G-402 and G-710 produced by Daicel Co., etc. and others. Further, partially esterified compounds of these epoxy compounds (e.g. esterified by (meth)acrylates) can be used in combination. Examples of oxetane compounds are 3-ethyl-3-hydroxymethyloxetane (oxetane alcohol), 2-ethylhexyloxetane, xylene bisoxetane, 3-ethyl-3[[(3-ethyloxetane-3-yl)methoxy]methyl]oxetane (Aron Oxetane series) provided by Toagosei Co., Ltd.

The photopolymerizable compositions can be used for various purposes, for example as printing ink, e.g. screen printing inks, inks for offset- or flexo printing, as a clear finish, as a white or colored finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists, solder resists, electroplating resists, or permanent resists, both liquid and dry films, as photostructurable dielectric, for printed circuit boards and electronic circuits, as resists to manufacture color filters for a variety of display applications or to generate structures in the manufacturing process of plasma-display panels and electroluminescence displays, (as for example described in U.S. Pat. No. 5,853,446, EP863534, JP 09-244230-A, JP10-62980-A, JP08-171863-A, U.S. Pat. No. 5,840,465, EP855731, JP05-271576-A, JP 05-67405-A) for the production of holographic data storage (HDS) material, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and integrated circuits, or as coatings for optical fibres, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE19700064 and EP678534.

The novel photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators can also be used for the polymerization of radiation-curable powder coatings. The powder coatings can be based on solid resins and monomers containing reactive double bonds, for example maleates, vinyl ethers, acrylates, acrylamides and mixtures thereof.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

The novel radiation-sensitive compositions further find application as negative resists, having a very high sensitivity to light and being able to be developed in an aqueous alkaline medium without swelling. They are suitable for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

The novel composition also relates to a photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of exposing a layer of the resin composition selectively to an actinic ray through a photomask having a pattern and developing the unexposed part of the layer.

The solder resist is a substance which is used during the soldering of a given part to a printed circuit board for the purpose of preventing molten solder from adhering to irrelevant portions and protecting circuits. It is, therefore, required to possess such properties as high adhesion, insulation resistance, resistance to soldering temperature, resistance to solvents, resistance to alkalis, resistance to acids, and resistance to plating.

Because the photocurable compositions according to the invention have a good thermal stability and are sufficiently resistant to inhibition by oxygen, they are particularly suitable for the production of color filters or color mosaic systems, such as described, for example, in EP320264. Color filters usually are employed in the manufacturing of flat panel displays such as LCD's, PDP (plasma panel display), EL (electroluminessence) display, and projection systems, image sensors, CCD (charge coupled device), and CMOS (complementary metal oxide semiconductor) sensors for scanner, digital camera and video camera.

The color filters usually are prepared by forming red, green and blue pixels and a black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating to actinic radiation and subsequent development of the pattern in an aqueous alkaline developer solution and optionally a heat treatment. Thus, by subsequently applying a red, green and blue pigmented coating, in any desired order, on top of each other with this process a color filter layer with red, green and blue color pixels can be produced.

The development is carried out by washing out the areas which were not polymerized with a suitable alkali developing solution. This process is repeated to form the image having plural colors.

In the light-sensitive resin composition of the present invention, with a process in which at least one or more picture elements are formed on a transparent substrate and then an exposure is given from a side of the transparent substrate, on which the above picture elements are not formed, the above picture elements can be utilized as a light-shielding mask. In this case, for example, in the case where an overall exposure is given, a position adjustment of a mask gets unnecessary and a concern on a position slippage thereof is removed. And, it is possible to cure all of the part on which the above picture elements are not formed. Further, in this case, it is possible as well to develop and remove a part of the portion on which the above picture elements are not formed by using partially a light-shielding mask.

Since in either case, no gap is formed between the picture elements which are formed formerly and those which are formed later, the composition of the present invention is suitable for, for example, a forming material for a color filter. To be concrete, the coloring matters, dyes and pigments of red, green and blue colors are added to the light-sensitive resin composition of the present invention, and the processes for forming an image are repeated to form the picture elements of red, green and blue colors. Then, the light-sensitive resin composition to which, for example, the black coloring materials, dyes and pigments are added is provided on an overall face. An overall exposure (or a partial exposure via a light-shielding mask) can be provided thereon to form the picture elements of a black color all over the spaces (or all but a partial region of the light-shielding mask) between the picture elements of red, green and blue colors.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

A metal support, glass, ceramics, and a synthetic resin film can be used as a support for a color filter. Glass and a synthetic resin film which is transparent and have an excellent dimension stability is particularly preferred.

The thickness of the light-sensitive resin composition layer is usually 0.1 to 50 micrometers, in particular 0.5 to 5 micrometers.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 5 to about 60 minutes.

The compositions according to this invention can also comprise latent pigments which are transformed into finely dispersed pigments during the heat treatment of the latent pigment containing photosensitive pattern or coating. The heat treatment can be performed after exposure or after development of the latent pigment-containing photoimageable layer. Such latent pigments are soluble pigment precursors which can be transformed into insoluble pigments by means of chemical, thermal, photolytic or radiation induced methods as described, for example, in U.S. Pat. No. 5,879,855. This transformation of such latent pigments can be enhanced by adding a compound which generates acid at actinic exposure or by adding an acidic compound to the composition. Therefore, a color filter resist can also be prepared, which comprises a latent pigment in a composition according to this invention.

Examples of color filters, especially with respect to the above described combinations of pigments and ionic impurity scavenger are given in EP320264. It is understood, that the photoinitiators according to the present invention, i.e. the compounds of the formula I or II in the color filter formulations described in EP 320264 can replace the triazine initiator compounds. Suitable components for a color filter compositions are described above in more detail.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. Nos. 5,368,976; 5,800,952; 5,882,843; 5,879, 855; 5,866,298; 5,863,678; JP 06-230212A; EP320264; JP 09-269410A; JP 10-221843A; JP 01-090516A; JP 10-171119A, U.S. Pat. Nos. 5,821,016, 5,847,015, 5,882, 843, 5,719,008, EP881541, or EP902327.

The photoinitiators of the present invention can be used in color filter resists, for example, such as those given as examples above, or can partially or fully replace the known photoinitiators in such resists. It is understood by a person skilled in the art that the use of the new photoinitiators of the present invention is not limited to the specific binder resins, crosslinkers and formulations of the color filter resist examples given hereinbefore but can be used in conjunction with any radically polymerizable component in combination with a dye or color pigment or latent pigment to form a photosensitive color filter ink or color filter resist.

Accordingly, subject of the invention also is a color filter prepared by providing red, green and blue (RGB) colour elements and, optionally a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder and a photopolymerization initiator of formula I or II, as described above. The monomer and binder components, as well as suitable pigments are as described above. In the manufacture of color filters the transparent electrode layer can either be applied on the surface of the transparent substrate or can be provided on the surface of the red, green and blue picture elements and the black matrix. The transparent substrate is for example a glass substrate which can additionally have an electrode layer on its surface.

It is preferred to apply a black matrix between the color areas of different color in order to improve the contrast of a color filter.

The photosensitive compositions of the present invention, as already stated above, are also suitable for the preparation of the black matrix of color filters. Said black matrix composition for example comprises a photoinitiator compound of the formula I or II of the present invention, an organic binder, in particular an organic binder, which is an epoxy acrylate resin having a carboxyl group, a black coloring material, a polymer dispersant, in particular a polymer dispersant containing a basic functional group.

The person skilled in the art is familiar with such formulations. Examples of suitable black matrix compositions and the components (other than the photoinitiator) as described above are given in JP Patent No. 3754065, the disclosure of which hereby is incorporated by reference.

Instead of forming a black matrix using a photosensitive composition and patterning the black photosensitive composition photolithographically by patternwise exposure (i.e. through a suitable mask) to form the black pattern separating the red green and blue coloured areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

There are different methods known how and at which step in the color filter manufacturing process the black matrix can be applied. It can either be applied directly on the transparent substrate prior to formation of the red, green and blue (RGB) colour filter as already mentioned above, or it can be applied after the RGB colour filter is formed on the substrate.

In a different embodiment of a color filter for a liquid crystal display, according to U.S. Pat. No. 626,796, the black matrix can also be applied on the substrate opposite to the RGB color filter element-carrying substrate, which is separated from the former by a liquid crystal layer.

If the transparent electrode layer is deposited after applying the RGB color filter elements and—optionally—the black matrix, an additional overcoat film as aprotective layer can be applied on the color filter layer prior to deposition of the electrode layer, for example, as described in U.S. Pat. No. 5,650,263.

To form an overcoat layer of a color filter, photosensitive resin or thermosetting resin compositions are employed. The photosensitive composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009A, JP1-130103A and JP1-134306A. In this regard, it is difficult to selectively form a protective layer with good precision using the above-mentioned thermosetting resins. The photosensitive composition, however, allows to easily remove the unnecessary parts of the protective layer by photolithography.

It is obvious to those skilled in the art, that the photosensitive compositions of the present invention can be used for generating red, green and blue color pixels and a black matrix, for the manufacture of a color filter, regardless of the above described differences in processing, regardless, of additional layers which can be applied and regardless of differences in the design of the color filter. The use of a composition according to the present invention to form colored elements shall not be regarded as limited by different designs and manufacturing processes of such color filters.

The photo-sensitive composition of the present invention can suitably be used for forming a color filter but will not be limited to this application. It is useful as well for a recording material, a resist material, a protective layer, a dielectric layer, in display applications and display elements, a paint, and a printing ink.

The photosensitive compositions according to the invention are also suitable for manufacturing interlayer insulating layers or dielectric layers in a liquid crystal display, and more particularly in a reflection type liquid crystal display including an active matrix type display having a thin film transistor (TFT) as a switching device, and a passive matrix type without a switching device.

In recent years, liquid crystal displays have, for example, been widely used for pocket-type TV sets and terminal devices for communication by virtue of its small thickness and light weight. A reflection type liquid crystal display without necessity of using a back light is in particular in demand because it is ultra-thin and light-weight, and it can significantly reduce power consumption. However, even if a back light is removed out of a presently available transmission type color liquid crystal display and a light reflection plate is added to a lower surface of the display, it would cause a problem in that the efficiency of utilizing lights is low, and it is not possible to have practical brightness. As a solution to this problem, there have been suggested various reflection type liquid crystal displays for enhancing an efficiency of utilizing lights. For instance, a certain reflection type liquid crystal display is designed to include a pixel electrode having reflection function.

The reflection type liquid crystal display includes an insulating substrate and an opposing substrate spaced away from the insulating substrate. A space between the substrates is filled with liquid crystals. A gate electrode is formed on the insulating substrate, and both the gate electrode and the insulating substrate are covered with a gate insulating film. A semiconductor layer is then formed on the gate insulating film above the gate electrode. A source electrode and a drain electrode are also formed on the gate insulating film in contact with the semiconductor layer. The source electrode, the drain electrode, the semiconductor layer, and the gate electrode cooperate with one another to thereby constitute a bottom gate type TFT as a switching device.

An interlayer insulating film is formed covering the source electrode, the drain electrode, the semiconductor layer, and the gate insulating film therewith. A contact hole is formed throughout the interlayer insulating film on the drain electrode. A pixel electrode made of aluminum is formed on both the interlayer insulating film and an inner sidewall of the contact hole. The drain electrode of the TFT is eventually in contact with the pixel electrode through the interlayer insulating film. The interlayer insulating layer is generally designed to have a roughened surface by which the pixel electrode acts as a reflection plate which diffuses lights to get a wider angle for viewing (angle of visibility).

The reflection type liquid crystal display remarkably enhances an efficiency of using lights by virtue that the pixel electrode acts as a light reflection plate.

In the above-mentioned reflection type liquid crystal display, the interlayer insulating film is designed to have projections and recesses by photolithography. To form and control a fine shape of the projections and recesses in micrometer order for surface roughness and to form contact holes, photolithography methods using positive and negative photoresists are used. For these resists the compositions according to the invention are especially suitable.

The photosensitive compositions according to the invention can further be used for manufacturing spacers, which control a cell gap of the liquid crystal part in liquid crystal display panels. A transparent column spacer has been widely used in the LCD technology, but the transparent spacer disturbs polarized light reducing the contrast ratio. One of a possible solution is to mix with a black colorant not to scatter but to absorb the polarized light, i.e. a black column spacer. Black column spacer is also used in the LCD technology. In case of black column spacer, one or more further black colorants or mixture of other color colorants described above colorant is used.

Since the properties of light transmitted or reflected through the liquid crystal layer in a liquid crystal display are dependent on the cell gap, the thickness accuracy and uniformity over the pixel array are critical parameters for the performance of the liquid crystal display unit. In a liquid crystal cell, the spacing between the substrates in the cell is maintained constant by sparsely distributing glass or polymer spheres about several micrometers in diameter as spacers between the substrates. The spacers are thus held between the substrates to maintain the distance between the substrates at a constant value. The distance is determined by the diameter of the spacers. The spacers assure the minimum spacing between the substrates; i.e., they prevent a decrease in distance between the substrates. However, they cannot prevent the substrates from being separated apart from each other, i.e. the increase in distance between the substrates. Additionally, this method of using spacer beads has problems of the uniformity in the diameter of spacer beads and difficulty in the even dispersion of spacer beads on the panel, as well as non-uniform orientation and decrease in brightness and/or optical aperture depending on the location of spacers on pixel array region. Liquid crystal displays having a large image display area have recently been attracting much attention. However, the increase in the area of a liquid crystal cell generally produces the distortion of the substrates constituting the cell. The layer structure of the liquid crystal tends to be destroyed due to the deformation of the substrate. Thus, even when spacers are used for maintaining the spacing between the substrates constant, a liquid crystal display having a large image display area is unfeasible because the display experiences disturbances. Instead of the above spacer sphere dispersion method, a method of forming columns in the cell gap as spacers has been proposed. In this method, columns of a resin are formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In recent years, as the spread of the touch panel type liquid crystal displays such as mobile audio players and handheld game platforms, the mechanical stress to liquid crystal panel tends to grow. The demand for spacer that controls the cell gap to raise mechanical strength becomes strong thus the multi-spacer method is used. According to the multi-spacer method, when cell gap narrows by pressure from the outside, adding to main-spacer that controls the cell gap normally lower sub-spacer supports the cell gap against external stress. The multi-spacer can follow the contraction of liquid crystal at low temperature conditions by main-spacer and prevent to generate bubbles inside the liquid crystal.

The multi-spacer which contains main-spacer and sub-spacer is formed in the same step using, for example, a halftone mask as described in JPA-2011065133. The photosensitive compositions according to the invention are eligible for manufacturing process using halftone mask.

In a color liquid crystal display panel, such spacers are formed in the nonimaging area under black matrix of color filter elements. Therefore, the spacers formed using photosensitive compositions do not decrease brightness and optical aperture.

Photosensitive compositions for producing protective layer with spacers for color filters are disclosed in JP 2000-81701A and dry film type photoresists for spacer materials are also disclosed in JP 11-174459A and JP 11-174464A. As described in the documents, the photosensitive compositions, liquid and dry film photoresists, are comprising at least an alkaline or acid soluble binder polymer, a radically polymerizable monomer, and a radical initiator. In some cases, thermally crosslinkable components such as epoxide and carboxylic acid may additionally be included.

The steps to form spacers using a photosensitive composition are as follows:

a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a postbaking is carried out to thermally cure the composition.

The photocurable compositions according to the invention are suitable for producing spacers for liquid crystal displays (as described above) because of their high sensitivity.

The photosensitive compositions according to the invention are also suitable for manufacturing microlens arrays used in liquid crystal display panels, image sensors and the like.

Microlenses are microscopic passive optical components that fit on active optoelectronic devices such as detectors, displays, and light emitting devices (light-emitting diodes, transversal and vertical cavity lasers) to improve their optical input or output quality. The areas of applications are wide and cover areas such as telecommunications, information technology, audio-visual services, solar cells, detectors, solid-state light sources, and optical interconnects.

Present optical systems use a variety of techniques to obtain efficient coupling between microlenses and microoptical devices.

The microlens arrays are used for condensing illuminating light on the picture element regions of a nonluminescent display device, such as a liquid crystal display devices, to increase the brightness of the display, for condensing incident light or as a means for forming an image on the photoelectric conversion regions of a line image sensor used for example in facsimiles and the like to improve the sensitivity of these devices, and for forming an image to be printed on a photosensitive means used in liquid crystal printers or light emitting diode (LED) printers.

The most common application is their use to improve the efficiency of photodetector arrays of a solid-state image sensing device such as a charge coupled device (CCD). In a detector array, the collection of as much light as possible in each detector element or pixel is wanted. If a microlens is put on top of each pixel, the lens collects incoming light and focuses it onto an active area that is smaller than the size of the lens.

According to the prior-art, microlens arrays can be produced by a variety of methods; for each of them compositions according to the present invention may be employed.

(1) A method for obtaining convex lenses wherein a pattern of the lenses in a planar configuration is drawn on a thermoplastic resin by a conventional photolithographic technique or the like, and then the thermoplastic resin is heated to a temperature above the softening point of the resin to have flowability, thereby causing a sag in the pattern edge (so called "reflowing") (see, e.g., JP 60-38989A, JP 60-165623A, JP 61-67003A, and JP 2000-39503A). In this method, when the thermoplastic resin used is photosensitive, a pattern of the lenses can be obtained by exposure of this resin to light.

(2) A method for forming a plastic or glass material by the use of a mold or a stamper. As lens material, a photocurable resin and a thermosetting resin can be used in this method (see, e.g., WO99/38035).

(3) A method for forming convex lenses on the basis of a phenomenon in which when a photosensitive resin is exposed to light in a desired pattern by the use of an aligner, unreacted monomers move from the unexposed regions to the exposed regions, resulting in a swell of the exposed regions (see, e.g., Journal of the Research Group in Microoptics Japanese Society of Applied Physics, Colloquium in Optics, Vol. 5, No. 2, pp. 118-123 (1987) and Vol. 6, No. 2, pp. 87-92(1988)).

On the upper surface of a supporting substrate, a photosensitive resin layer is formed. Thereafter, with the use of a separate shading mask, the upper surface of the photosensitive resin layer is illuminated with light from a mercury lamp or the like, so that the photosensitive resin layer is exposed to the light. As a result, the exposed portions of the photosensitive resin layer swell into the shape of convex lenses to form the light condensing layer having a plurality of microlens.

(4) A method for obtaining convex lenses wherein a photosensitive resin is exposed to light by a proximity exposure technique in which a photomask is not brought into contact with the resin, to cause a blur at the pattern edge, so that the amount of photochemical reaction products is distributed depending upon the degree of blurring at the pattern edge (see, e.g., JP 61-153602A).

(5) A method for generating a lens effect wherein a photosensitive resin is exposed to light with a particular intensity distribution to form a distribution pattern of refractive index depending upon the light intensity (see, e.g., JP 60-72927A and JP 60-166946A). The photosensitive compositions according to the invention can be used in any one of the above-mentioned methods to form microlens arrays using photocurable resin compositions.

A particular class of techniques concentrates on forming microlenses in thermoplastic resins like photoresist. An example is published by Popovic et al. in the reference SPIE 898, pp. 23-25 (1988). The technique, named reflow technique, comprises the steps of defining the lenses' footprint in a thermoplastic resin, e.g. by photolithography in a photosensitive resin like a photoresist, and subsequently heating this material above its reflow temperature. The surface tension draws the island of photoresist into a spherical cap with a volume equal to the original island before the reflow. This cap is a plano-convex microlens. Advantages of the technique are, amongst others, the simplicity, the reproducibility, and the possibility of integration directly on top of a light-emitting or light-detecting optoelectronic device.

In some cases, an overcoat layer is formed on the patterned lens units with a rectangular shape prior to reflowing to avoid a sagging of the island of the resin in the middle without reflow into a spherical cap in the reflow step. The overcoat acts as a permanent protective layer. The coating layer is also made of a photosensitive composition. Microlens arrays can also be fabricated by the use of a mold or a stamper as, for example, disclosed in EP0932256. A process of manufacturing the planar microlens array is as follows: a release agent is coated on a shaping surface of a stamper on which convex portions are densely arranged, and a photocurable synthetic resin material having a high refractive index is set on the shaping surface of the stamper. Next, the base glass plate is pushed onto the synthetic resin material, thereby spreading the synthetic resin material, and the synthetic resin material is cured by irradiating with ultraviolet radiation or by heating and is shaped to form the convex microlenses. Thereafter the stamper is peeled off. Then, a photocurable synthetic resin material having a low refractive index is additionally coated onto the convex microlenses as an adhesive layer and a glass substrate which is made into a cover glass plate is pushed onto the synthetic resin material, thereby spreading the same. The synthetic resin material is then cured and finally the planar microlens array is formed.

As disclosed in U.S. Pat. No. 5,969,867, a similar method using a mold is applied for the production of a prism sheet, which is used as a part of backlight units for color liquid crystal display panels to enhance the brightness. A prism sheet forming a prism row on one side is mounted on the light-emitting surface of the backlight. For fabricating a prism sheet, an active energy ray-curable composition is cast and spread in a lens mold which is made of metal, glass or resin and forms the lens shape of the prism row, etc., after which a transparent substrate sheet is placed onto it and active energy rays from an active energy ray-emitting source are irradiated through the sheet for curing. The prepared lens sheet is then released from the lens mold to obtain the lens sheet.

The active energy ray-curable composition used to form the lens section must have a variety of properties, including adhesion to the transparent substrate, and suitable optical characteristics.

Lenses at least with some photoresists in the prior art are not desirable for some applications since the optical transmittance in the blue end of the optical spectrum is poor. Because the photocurable compositions according to the invention have low yellowing properties, both thermally and photochemically, they are suitable for the production of microlens arrays as described above.

The novel radiation-sensitive compositions are also suitable for photolithographic steps used in the production process of plasma display panels (PDP), particularly for the imaging forming process of barrier rib, phosphor layer and electrodes.

The PDP is a planar display for displaying images and information by virtue of the emission of light by gas discharge. By the construction of panel and the method of operation, it is known in two types, i.e. DC (direct current) type and AC (alternating current) type.

By way of example, the principle of the DC type color PDP will be briefly explained. In the DC type color PDP, the space intervening between two transparent substrates (generally glass plates) is divided into numerous minute cells by latticed barrier ribs interposed between the transparent substrates. In the individual cells a discharge gas, such as He or Xe, is sealed. On the rear wall of each cell there is a phosphor layer which, on being excited by the ultraviolet light generated by the discharge of the discharge gas, emits visible light of three primary colors. On the inner faces of the two substrates, electrodes are disposed as opposed to each other across the relevant cells. Generally, the cathodes are formed of a film of transparent electroconductive material such as NESA glass. When a high voltage is applied between these electrodes formed on the fore wall and the rear wall, the discharge gas which is sealed in the cells induces plasma discharge and, by virtue of the ultraviolet light radiated consequently, incites the fluorescent elements of red, blue, and green colors to emit lights and effect the display of an image. In the full-color display system, three fluorescent elements severally of the three primary colors of red, blue, and green mentioned above jointly form one picture element.

The cells in the DC type PDP are divided by the component barrier ribs of a lattice, whereas those in the AC type PDP are divided by the barrier ribs which are arranged parallel to each other on the faces of the substrates. In either case, the cells are divided by barrier ribs. These barrier ribs are intended to confine the luminous discharge within a fixed area to preclude false discharge or cross talk between adjacent discharge cells and ensure ideal display.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

The compounds of the formula I or II are also suitable as photoinitiators in the holographic data storage application. Said photoinitiators generate radicals and initiate polymerization of monomer upon irradiation with blue laser radiation, suitable for holographic data storage. The wavelength range of the blue laser is 390-420 nm, preferably 400-410 nm and particularly 405 nm. Holographic storage systems (holographic recording media) are for example used to record and to retrieve a large amount of data with fast access time. The photoinitiators of the invention are for example in particular suitable for systems as described for example in WO03/021358.

The holographic data storage system is preferably comprised of a matrix network of low-refractive index matrix precursors and high-refractive index photopolymerizable monomers.

The matrix precursor and photoactive monomer can be selected such that (a) the reaction by which the matrix precursor is polymerized during the cure is independent from the reaction by which the photoactive monomer will be polymerized during writing of a pattern, e.g. data, and (b) the matrix polymer and the polymer resulting from polymerization of the photoactive monomer (the photopolymer) are compatible with each other. The matrix is considered to be formed when the photorecording material, i.e. the matrix material plus the photoactive monomer, photoinitiator and/or additives, exhibits an elastic modulus of at least about $10^5$ Pa, generally about $10^5$ Pa to about $10^9$ Pa.

The media matrix is formed by in-situ polymerization which yields as cross-linked network in the presence of the photopolymerizable monomers which remain "dissolved" and unreacted. The matrix containing un-reacted, photopolymerizable monomers can also be formed by other means, for example by using a solid-resin matrix material in which the photoreactive, liquid monomer is homogeneously distributed. Then, monochromatic exposure generates the holographic pattern, which according to the light intensity distribution, polymerizes the photoreactive monomers in the solid pre-formed matrix. The unreacted monomers (where light intensity was at a minimum) diffuse through the matrix, producing a modulation of the refractive index that is determined by the difference between the refractive indices of the monomer and the matrix and by the relative volume fraction of the monomer. The thickness of the recording layer is in the range of several micrometers up to a thickness of one millimeter. Because of such thick holographic data storage layers it is required that the photoinitiator combines high photoreactivity with low absorbance, in order to render the layer transparent at the laser wavelength to assure that the extent of photopolymerization is as little as possible dependent on the exposure depth into the recording layer.

It was found that the photoinitiators of the present invention combine high reactivity with low absorbance at 405 nm and are suitable for this application. Dyes and sensitizers can also be added to the formulations. Suitable dyes and sensitizers for blue laser radiation are for example coumarines, xanthones, thioxanthones, see list above. In particular relevant are thioxanthones, coumarins and benzophenones as mentioned under items 1., 2. and 3. in the list given above.

It was found that the photoinitiators allow photopolymerization of monomers in thick layers, such as required for holographic data storage, with high sensitivity and yield recording layers which are sensitive to blue laser radiation. The photoinitiators, when applied at a concentration of 2-8 wt % in the photosensitive layer of 20 micron thickness yield an absorbance of the layer which comprises the photoinitiator, of less than 0.4, preferably less than 0.2 at the laser wavelength.

The photoinitiators are in particular suitable for the preparation of optical articles (for example optical waveguides) or holographic recording media e.g. comprising a polymer and an organic photoinitiator as described above, having a maximum absorption at a UV wavelength in the range of 340-450 nm, wherein the refractive index contrast adjusted sensitivity is greater than $3 \times 10^{-6} \Delta n/(mJ/cm^2)$. For example, the polymer is formed by polymerizing a material comprising component 1 and component 2, wherein component 1 comprises a NCO-terminated pre-polymer and component 2 comprises a polyol. Component 1 is, for example, diphenylmethane diisocyanate, toluene diisocyanate, hexamethylene diisocyanate, a derivative of hexamethylene diisocyanate, a methylenebiscyclohexylisocyanate, a derivative of methylenebiscyclohexylisocyanate. Component 2 is for example a polyol of propylene oxide. Preferably, the photoactive monomer is an acrylate monomer. In such media the shrinkage induced by writing is usually less than 0.25%.

Photocuring further is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel photoinitiators for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists. When used in image-forming materials the novel photoinitiators provide excellent performance in generating so called printout images, whereby a color change is induced due to irradiation. To form such printout images different dyes and/or their leuco form are used and examples for such print out image systems can be fount e.g. in WO96/41240, EP706091, EP511403, U.S. Pat. Nos. 3,579,339 and 4,622,286.

The novel photoinitiator is also suitable for a photopatternable composition for forming a dielectric layer of a multilayer layer circuit board produced by a sequential build-up process.

The invention, as described above, provides compositions, as well as a process, for producing pigmented and nonpigmented paints and varnishes, powder coatings, printing inks, printing plates, adhesives, pressure sensitive adhesives, dental compositions, gel coats, photoresists for electronics, etch resists, both liquid and dry films, solder resists, resists to manufacture color filters for a variety of display applications (a color filter resist contains pigments, pigments and dyes (i.e. hybrid systems) or dyes alone), resists to generate structures in the manufacturing processes of plasma-display panels (e.g. barrier rib, phosphor layer, electrode), electroluminescence displays and LCD (e.g. interlayer insulating layers, spacers, multi-spacers, microlens arrays), for encapsulating electrical and electronic components, for producing magnetic recording materials, micromechanical parts, waveguides, optical switches, plating masks, colour proofing systems, glass fibre cable coatings, screen printing stencils, three-dimensional objects by means of stereolithography, image recording materials for holographic recordings (e.g. for holographic data storage (HDS)), microelectronic circuits, decolorizing materials, formulations containing microcapsules, photoresist materials for a UV and visible laser direct imaging system and for forming dielectric layers in a sequential build-up layer of a printed circuit board, bank/pixel definition layers for OLED, sealants for LCD and OLED, insulation/passivation layers for LCD and OLED, insulation for metal wiring/transparent conductive films for touch panel, coatings for touch panel, decorative inks for touch panel, protective films for touch panel or etching resists for touch panel; wherein the process comprises irradiating a composition as described above with electromagnetic radiation in the range from 150 to 600 nm, or with electron beam or with X-rays.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are, for example, silicon wafers. The layer thickness of the photosensitive layer for photographic materials and offset printing forms is generally from about 0.5 μm to 10 μm, while for printed circuits it is from 0.1 μm to about 100 μm. Following the coating of the substrates, the solvent is removed, generally by drying, to leave a coat of the photoresist on the substrate.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methyl-pyrrolidone, dioxane, tetrahydrofuran, 2-methoxyethanol, 2-ethoxyethanol, 1-methoxy-2-propanol, 1,2-dimethoxyethane, ethyl acetate, n-butyl acetate, ethyl 3-ethoxypropionate, 2-methoxypropylacetate, methyl-3-methoxypropionate, 2-heptanone, 2-pentanone, and ethyl lactate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, or a glass substrate by transferring the layer via lamination.

The quantity applied (coat thickness) and the nature of the substrate (layer support) are dependent on the desired field of application. The range of coat thicknesses generally comprises values from about 0.1 μm to more than 100 μm, for example 0.1 μm to 1 cm, preferably 0.5 μm to 1000 μm.

Following the coating of the substrates, the solvent is removed, generally by drying, to leave an essentially dry resist film of the photoresist on the substrate.

The photosensitivity of the novel compositions can extend in general from about 150 nm to 600 nm, for example 190-600 nm, (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, low-, medium-, high- and super high-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED, OLED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as $F_2$ excimer lasers at 157 nm exposure, KrF excimer lasers for exposure at 248 nm and ArF excimer lasers for exposure at 193 nm are also suitable. Lasers in the visible region can also be employed.

The term "imagewise" exposure includes both, exposure through a photomask comprising a predetermined pattern, for example a slide, a chromium mask, a stencil mask or a reticle, as well as exposure by means of a laser or light beam, which for example is moved under computer control over the surface of the coated substrate and in this way produces an image. Suitable UV laser exposure systems for the purpose are, for example, provided by Etec and Orbotech (DP-100™ DIRECT IMAGING SYSTEM). Other examples of laser light sources are, for example excimer lasers, such as $F_2$ excimer lasers at 157 nm exposure, KrF excimer lasers for exposure at 248 nm and ArF excimer lasers for exposure at 193 nm. Further suitable are solid state UV lasers (e.g. Gemini from ManiaBarco, DI-2050 from PENTAX) and violet laser diodes with 405 nm output (DI-2080, DI-PDP from PENTAX). Lasers in the visible region can also be employed. And the computer-controlled irradiation can also be achieved by electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37. Following the imagewise exposure of the material and prior to development, it may be advantageous to carry out thermal treatment for a short time. After the development a thermal post bake can be performed to harden the composition and to remove all traces of solvents. The temperatures employed are generally 50-250° C., preferably 80-220° C.; the duration of the thermal treatment is in general between 0.25 and 60 minutes.

The invention therefore also provides a process for the photopolymerization of compounds containing ethylenically unsaturated double bonds, i.e. monomeric, oligomeric or polymeric compounds containing at least one ethylenically unsaturated double bond, which comprises adding to these compounds at least one photoinitiator of the formula I or II as described above and irradiating the resulting composition with electromagnetic radiation, in particular light of the wavelength 150 to 600 nm, in particular 190-600 nm, with electron beam, or with X-rays.

In other words, adding to these compounds containing ethylenically unsaturated double bonds at least one photoinitiator of the formula I, II, III, IV or V as described above and irradiating the resulting composition with electromagnetic radiation, in particular light of the wavelength 150 to 600 nm, in particular 190-600 nm, with electron beam, or with X-rays.

The invention further provides a coated substrate which is coated on at least one surface with a composition as described above.

Interesting also is a process for the photographic production of relief images, in which a coated substrate as described above is subjected to imagewise exposure and then the unexposed portions are removed with a developer. Imagewise exposure may be effected by irradiating through a mask or by means of a laser or electron beam as already described above. Of particular advantage in this context is the laser beam exposure already mentioned above.

The compounds of the invention have a good thermal stability, low volatility, good storage stability and high solubility, and are also suitable for photopolymerisations in the presence of air (oxygen). Further, they cause only low yellowing in the compositions after photopolymerization.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

SYNTHESIS EXAMPLES

Example 1

Preparation of OE-1

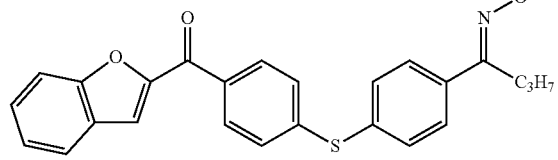

1.1: Preparation of IM-1

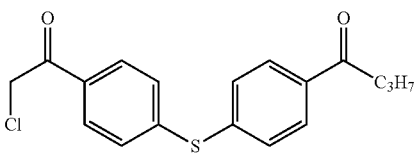

To 7.36 g of aluminum chloride in dichloromethan (50 mL) are added 9.31 g of diphenyl sulfide in portions at 0° C. Then, 5.56 g of chloroacetyl cholide is added at 0° C. and stirred for 2 hours at room temperature. To the reaction mixture, 7.33 g of aluminum chloride and 5.59 g of n-butyryl chloride are added to the mixture at 0° C., and then the mixture is stirred overnight. After the reaction mixture is poured onto ice water, the organic layer is extracted with dichloromethane. The solution is dried over MgSO$_4$, concentrated, and the residue is purified by column chromatography, giving 10.35 g of IM1 as white powder.

1.2: Preparation of IM-2

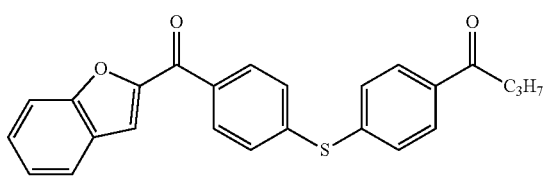

To 1.0 g of the diketone (IM-1) in 30 ml of acetone, 1.11 g of potassium carbonate and 0.73 g of salicylaldehyde are added and stirred under reflux for 3 hours. The reaction mixture is allowed to warm to room temperature, water is added and acidified by adding aq. HCl. The precipitate is collected by filtration and dried to give 1.0 g of IM-2.

1.3: Preparation of IM-3

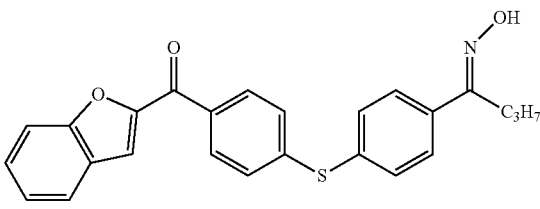

To 1.0 g of IM-2 in CH$_3$(CO)OC$_2$H$_5$ (AcOEt) (10 ml), 0.35 g of hydroxyl ammonium chloride and 5 ml of pyridine are added. The mixture is stirred under reflux for 3 hours. The reaction mixture is allowed to warm to room temperature and then is poured into water. The organic layer is extracted with AcOEt and dried over MgSO$_4$. After concentration, the crude product is purified by column chromatography, giving 283 mg of IM-3 as pale yellow solid.

1.4: Preparation of OE-1

To 283 mg of IM-3 in AcOEt (14 ml), 78.5 mg of acetyl chloride and 111 mg of triethyl amine are added and stirred for 3 hours at room temperature. The reaction mixture is poured into water and extracted with AcOEt. After concentration, the crude product is purified by column chromatography, giving 226 mg of OE-1 as pale yellow solid.

Example 2

Preparation of OE-2

OE-2 is prepared according to the method as described in example 1 except using the corresponding acid chloride. The structure and physical data are collected in the following table 1.

Example 3

Preparation of OE-3

OS-3 is prepared according to the method as described in example 1 except using the corresponding acid chloride and 2-hydroxy-1-naphthaldehyde instead of salicylaldehyde. The structure and physical data are collected in the following table 1.

Example 4

Preparation of OE-4

OE-4 is prepared according to the method as described in example 1 except using diphenylether instead of diphenylsulfide. The structure and physical data are collected in the following table 1.

Example 5

Preparation of OE-5

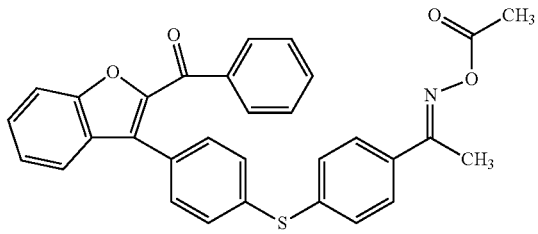 [SMILES: CC(=O)O/N=C(\C)c1ccc(Sc2ccc(-c3c(C(=O)c4ccccc4)oc4ccccc34)cc2)cc1]

5.1: Preparation of IM-4

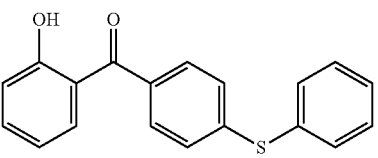 [SMILES: O=C(c1ccc(Sc2ccccc2)cc1)c1ccccc1O]

To 2.95 g of aluminum chloride in dichloromethan (20 mL) are added 5.59 g of diphenyl sulfide in portions at 0° C. Then, 3.42 g of 2-methoxybenzoyl choride is added at 0° C. and stirred for 2 hours at room temperature. After the reaction mixture is poured onto ice water, the organic layer is extracted with dichloromethane. The solution is dried over $MgSO_4$, concentrated, and the residue is purified by column chromatography, giving 2.80 g of IM-4 as yellow solid.

5.2: Preparation of IM-6

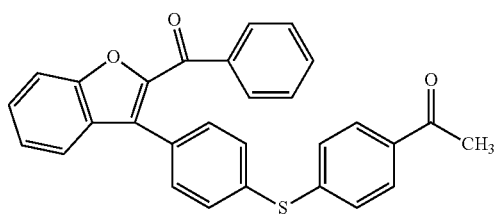 [SMILES: CC(=O)c1ccc(Sc2ccc(-c3c(C(=O)c4ccccc4)oc4ccccc34)cc2)cc1]

To 1.00 g of diketone (IM-4) in 13 ml of acetone, 0.46 g of potassium carbonate and 0.46 g of 2-chloroacetophenone are added, and stirred under reflux overnight. After the reaction mixture is allowed to warm to room temperature, water is added, extracted by ethyl acetate and dried over $Mg_2SO_4$. The organic layer is evaporated, giving 1.0 g of IM-5. IM-5 is converted to IM-6 by means of Friedel-Crafts acetylation.

5.3: Preparation of OE-5

IM-6 is converted to OE-5 according to the method as described in example 1.4. The corresponding physical data are collected in the following table 1.

Examples 6-11

Preparation of OE6-OE11

The compounds OE6-OE11 are prepared according to the method as described in example 1. The structures and physical data are collected in table 1.

Examples 12-31, 33-73

Preparation of OE12-OE31 and OE33-OE73

The oxime ester compounds OE12-OE31 and OE33-OE73 are prepared according to the method as described in example 1 using the corresponding ketone for oximation followed ba esterification.

Example 32

Preparation of OE32

The compound OE32 is prepared according to the method as described in example 1 via diketone (IM-7) and oxime (IM-8). The crude product is purified by recrystallization from $CH_3COOC_2H_5$ (AcOEt)/hexane, giving OE32 as a mixture of EZ (93:7) isomers.

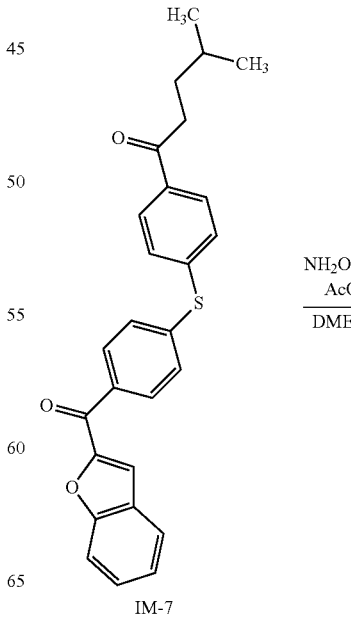

IM-7

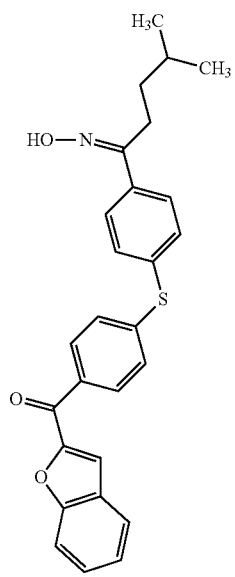

IM-8
mixture of E/Z
isomers

AcCl, Et3N / AcOEt →

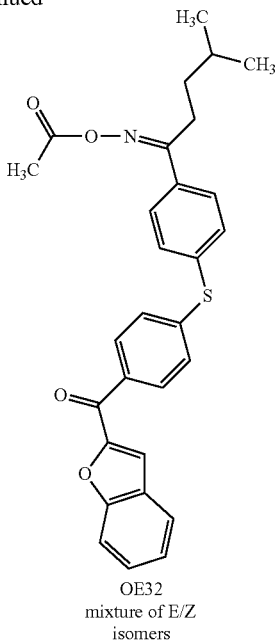

OE32
mixture of E/Z
isomers

Ac=acetyl; DME=dimethylether; Et=ethyl
$^1$H-NMR data
IM-7(CDCl$_3$): 0.88-0.98(d, 2H), 1.50-1.75(m, 3H), 2.80-2.88(t, 2H), 7.28-8.06 (m, 13H), IM-8(DMSO-d6): 0.78-0.92(m, 6H), 1.20-1.60(m, 3H), 2.42-2.76(m, 2H), 7.34-8.02 (m, 13H), 10.68-11.30(two singlet, 1H)

Example 74-75

A mixture of oxime EZ isomers (IM-8) is purified by column chromatography, giving a single component of oxime isomer E (IM-9) and Z (IM-10). OE74 and OE75 are prepared via conventional esterification manner from IM-9 and IM-10, respectively:

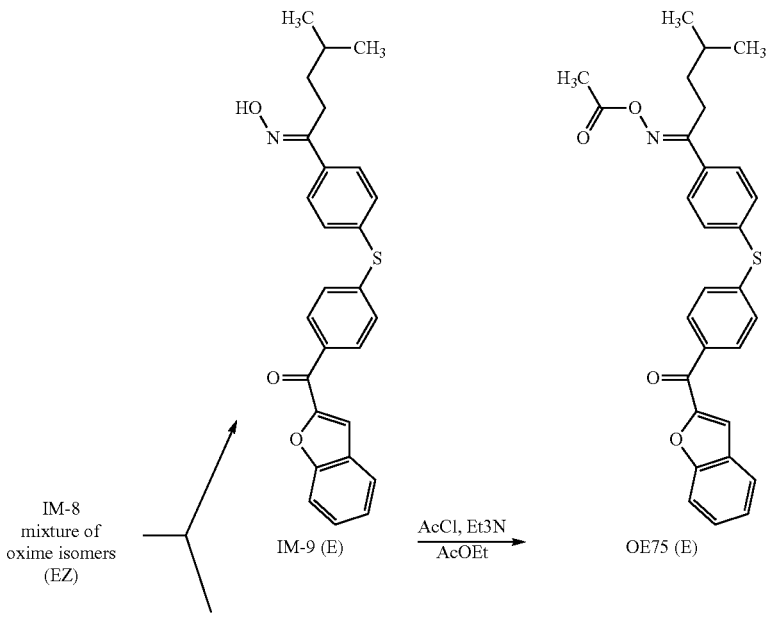

-continued

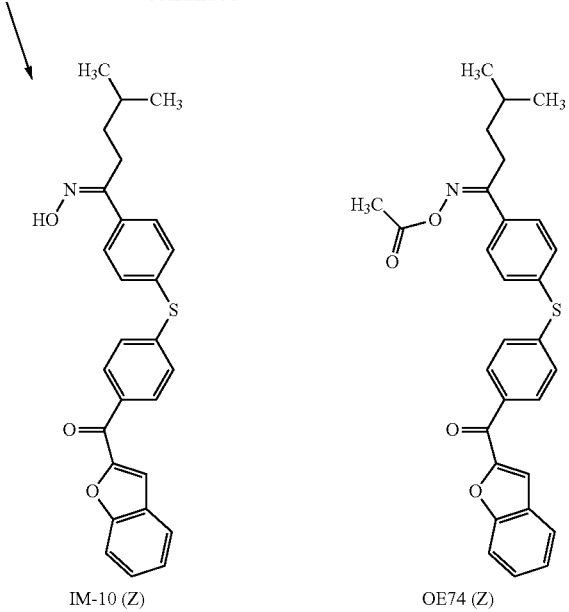

IM-10 (Z)　　　　　OE74 (Z)

¹H-NMR data
IM-9: (DMSO-d6) 0.84-0.92(m, 6H), 1.30-1.60(m, 3H), 2.64-2.76(m, 2H), 7.34-7.98 (m, 13H), 11.30(s, 1H)
IM-10: (DMSO-d6) 0.78-0.84(m, 6H), 1.20-1.38(m, 3H), 2.42-2.54(m, 2H), 7.34-8.02 (m, 13H), 10.68(s, 1H)

The oxime ester compounds (OE) are formed in E/Z isomeric mixtures. Only in single cases a differentiation and separation of said forms is indicated.

TABLE 1

| Oxime Ester | Structure | ¹H NMR in CDCl₃ |
|---|---|---|
| OE-1 | (benzofuran-C(=O)-C6H4-S-C6H4-C(=N-O-C(=O)CH3)-C3H7) | 0.96-1.02 (t, 3H), 1.54-1.66 (m, 2H), 2.50 (s, 3H), 2.78-2.86 (t, 2H), 7.28-7.32 (d, 1H), 7.32-7.36 (d, 2H), 7.46-7.50 (d, 2H), 7.52 (s, 1H), 7.68-7.74 (m, 3H), 7.95-7.99 (d, 2H) |
| OE-2 | (benzofuran-C(=O)-C6H4-S-C6H4-C(=N-O-C(=O)CH3)-C7H15) | 0.84-0.90 (t, 3H), 1.22-1.42 (m, 8H), 1.54-1.60 (m, 2H), 2.71 (s, 3H), 2.82-2.87 (t, 2H), 7.31-7.40 (m, 3H), 7.48-7.56 (m, 4H), 7.62-7.66 (d, 1H), 7.72-7.76 (d, 3H), 7.98-7.82 (d, 2H) |

TABLE 1-continued

| Oxime Ester | Structure | ¹H NMR in CDCl₃ |
|---|---|---|
| OE-3 | naphthofuran-C(=O)-C₆H₄-S-C₆H₄-C(CH₃)=N-O-C(=O)-CH₃ | 2.29 (s, 3H), 2.42 (s, 3H), 7.38-7.42 (d, 2H), 7.52-7.56 (d, 2H), 7.55-7.77 (m, 3H), 7.76-7.80 (d, 2H), 7.92-7.95 (d, 1H), 7.97-7.80 (d, 1H), 8.04 (s, 1H), 8.03-.07 (d, 2H), 8.19-8.22 (d, 1H) |
| OE-4 | naphthofuran-C(=O)-C₆H₄-O-C₆H₄-C(CH₃)=N-O-C(=O)-CH₃ | 2.29 (s, 3H), 2.42 (s, 3H), 7.13-7.19 (m, 4H), 7.55-7.60 (t, 1H), 7.65-7.70 (t, 1H), 7.74-7.78 (d, 1H), 7.80-7.85 (d, 2H), 7.92-7.96 (d, 1H), 7.97-7.81 (d, 1H) 8.07 (s, 1H), 8.16-8.23 (m, 3H), |
| OE-5 | benzofuran(2-benzoyl, 3-C₆H₄-S-C₆H₄-C(CH₃)=N-O-C(=O)-CH₃) | 2.28 (s, 3H), 2.39 (s, 3H), 7.31-7.42 (m, 7H), 7.46-7.50 (d, 2H), 7.52-7.58 (m, 2H), 7.64-7.72 (m, 4H), 7.87-7.91 (d, 2H) |
| OE6 | benzothiophene-C(=O)-C₆H₄-S-C₆H₄-C(C₃H₇)=N-O-C(=O)-CH₃ | 0.96-1.06 (t, 3H), 1.60-1.68 (m, 2H), 2.28 (s, 3H), 2.80-2.88 (t, 2H), 7.36-7.52 (m, 6H), 7.72-7.76 (d, 2H), 7.84-7.94 (m, 5H) |
| OE7 | benzofuran(3-C₂H₅, 2-C(=O)-C₆H₄-S-C₆H₄-C(C₃H₇)=N-O-C(=O)-CH₃) | 0.96-1.06 (t, 3H), 1.60-1.68 (m, 2H), 2.28 (s, 3H), 2.80-2.88 (t, 2H), 7.36-7.52 (m, 6H), 7.72-7.76 (d, 2H), 7.84-7.94 (m, 5H) |

TABLE 1-continued

| Oxime Ester | Structure | ¹H NMR in CDCl₃ |
|---|---|---|
| OE8 | 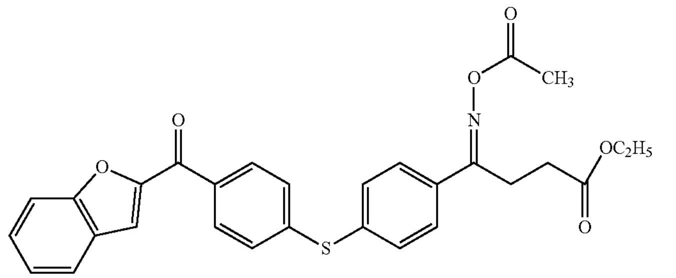 [SMILES: CCOC(=O)CCC(=NOC(C)=O)c1ccc(Sc2ccc(C(=O)c3cc4ccccc4o3)cc2)cc1] | 1.22-1.27 (t, 3H), 2.3 (s, 3H), 2.56-2.62 (t, 2H), 3.14-3.20 (t, 2H), 4.10-4.18 (q, 2H), 7.32-7.4 (m, 3H), 7.48-7.53 (m, 3H), 7.56 (s, 1H), 7.62-7.66 (d, 1H), 7.72-7.76 (m, 3H), 7.99-8.20 (d, 2H) |
| OE9 | 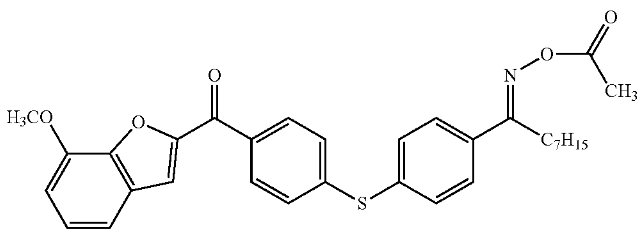 | 0.82-0.92 (t, 3H), 1.20-1.44 (m, 8H), 1.52-1.62 (m, 2H), 2.66 (s, 3H), 2.80-2.90 (t, 2H), 4.03 (s, 3H), 6.94-6.98 (d, 1H), 7.21-7.31 (m, 2H), 7.34-7.39 (d, 2H), 7.48-7.52 (d, 2H), 7.56 (s, 1H), 7.70-7.74 (d, 2H), 7.82-7.86 (d, 2H) |
| OE10 | 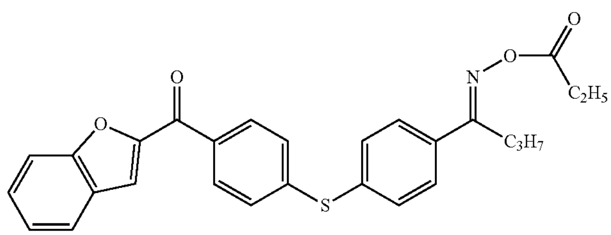 | 0.98-1.06 (t, 3H), 1.25-1.30 (t, 3H), 1.58-1.68 (m, 2H), 2.53-2.59 (q, 2H), 2.82-2.86 (t, 2H), 7.32-7.40 (m, 3h), 7.49-7.56 (m, 3H), 7.55 (s, 1H), 7.63-7.66 (d, 1H), 7.72-7.76 (m, 3H), 7.98-8.02 (d, 2H) |
| OE11 | 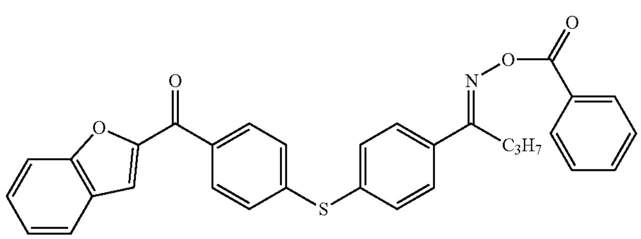 | 1.04-1.08 (t, 3H), 1.70-1.98 (m, 2H), 2.94-3.02 (q, 2H), 7.31-7.37 (t, 1H), 7.37-7.41 (d, 2H), 7.48-7.56 (m, 6H), 760-7.66 (t, 2H), 7.72-7.75 (t, 1H), 7.81-7.85 (d, 2H), 7.99-7.82 (d, 2H). 810-8.14 (d, 2H) |
| OE12 | 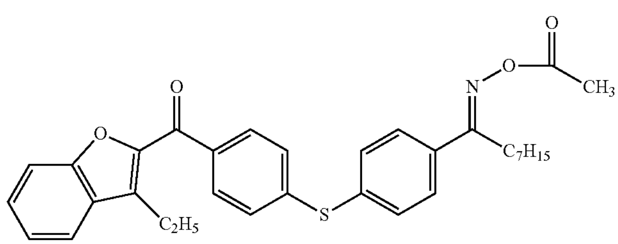 | 0.86-0.92 (t, 3H), 1.22-1.62 (m, 12H), 2.27 (s, 3H), 2.82-2.87 (t, 2H), 3.12-3.20 (q, 2H), 7.31-8.10 (m, 12H) |
| OE13 | 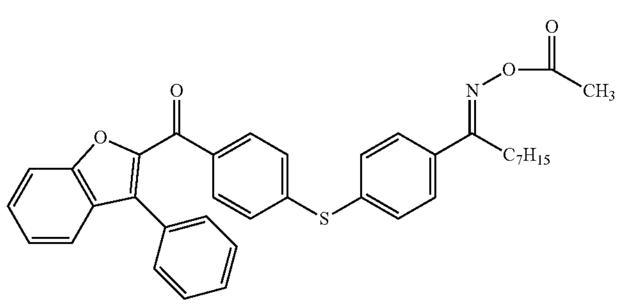 | 0.82-0.94 (t, 3H), 1.20-1.42 (m, 8H), 1.50-1.60 (m, 2H), 2.27 (s, 3H), 2.80-2.90 (t, 2H), 7.18-7.82 (m, 17H) |

TABLE 1-continued

| Oxime Ester | Structure | $^1$H NMR in CDCl$_3$ |
|---|---|---|
| OE14 | isomeric form of OE20 | 0.88 (t, 9H), 0.84-0.94 (d, 3H), 1.08-1.36 (m, 2H), 1.82-1.96 (m, 1H), 2.27 (s, 3H), 270-2.92 (m, 2H), 7.32-8.06 (m, 13H) |
| OE15 | 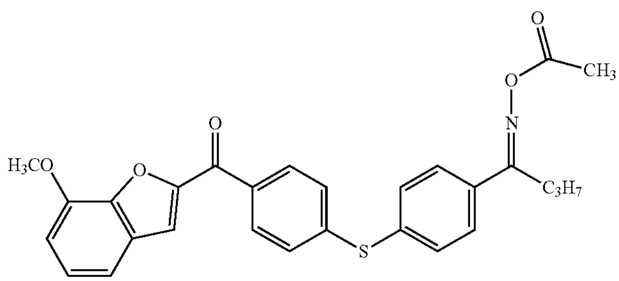 | 0.98-1.04 (t, 3H), 1.58-1.68 (m, 2H), 2.278 s, 3H), 2.80-2.89 (t, 2H), 4.4 (s, 3H), 6.95-8.08 m, 12H) |
| OE16 | 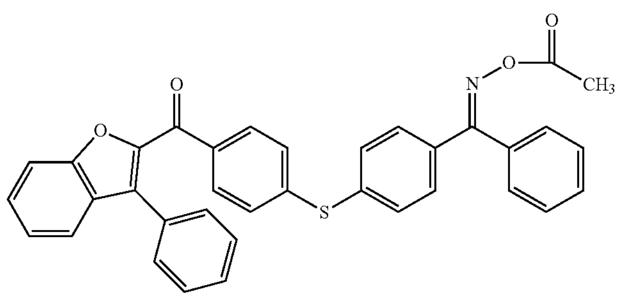 [SMILES: CC(=O)O/N=C(\c1ccccc1)c1ccc(Sc2ccc(C(=O)c3oc4ccccc4c3-c3ccccc3)cc2)cc1] | 2.27 (s, 3H), 7.19-8.22 (m, 17H) |
| OE17 | 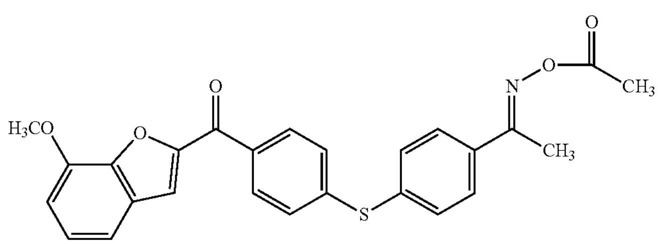 [SMILES: COc1cccc2cc(C(=O)c3ccc(Sc4ccc(/C(C)=N/OC(C)=O)cc4)cc3)oc12] | 2.28 (s, 3H), 2.41 (s, 3H), 4.04 (s, 3H), 7.75-8.08 (m, 12H) |
| OE18 | 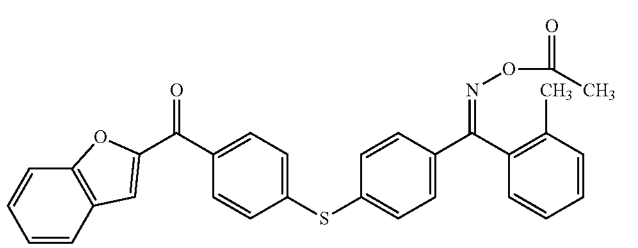 [SMILES: CC(=O)O/N=C(/c1ccc(Sc2ccc(C(=O)c3cc4ccccc4o3)cc2)cc1)c1ccccc1C] | 2.12 (s, 3H), 2.28 (s, 3H), 7.19-8.22 (m, 17H) |

TABLE 1-continued

| Oxime Ester | Structure | $^1$H NMR in CDCl$_3$ |
|---|---|---|
| OE19 | 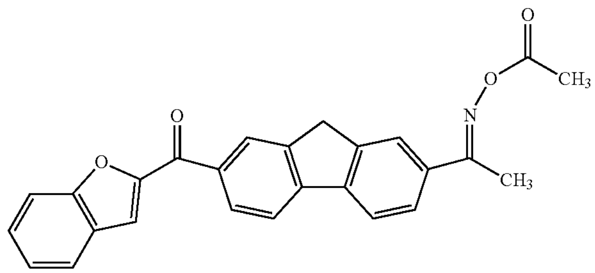 [SMILES: CC(=O)O/N=C(\C)c1ccc2c(c1)Cc1cc(C(=O)c3cc4ccccc4o3)ccc1-2] | 2.30 (s, 3H), 2.48 (s, 3H), 4.07 (s, 2H), 7.33-8.29 (m, 11H) |
| OE20 | isomeric form of OE14 | 0.82 (t, 9H), 0.90-0.99 (m, 4H), 1.10-1.35 (m, 2H), 2.08 (s, 3H), 2.52-2.88 (m, 2H), 7.32-8.06 (m, 13H) |
| OE21 | 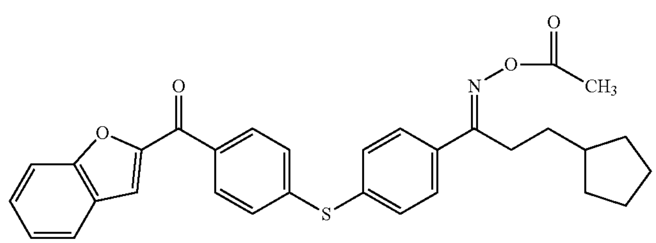 [SMILES: CC(=O)O/N=C(\CCC1CCCC1)c1ccc(Sc2ccc(C(=O)c3cc4ccccc4o3)cc2)cc1] | 1.05-1.20 (t, 2H), 1.50-1.70 (m, 6H), 1.75-1.86 (m, 3H), 2.27 (s, 3H) 2.80-2.89 (t, 2H), 7.32-8.02 m, 13H) |
| OE22 | 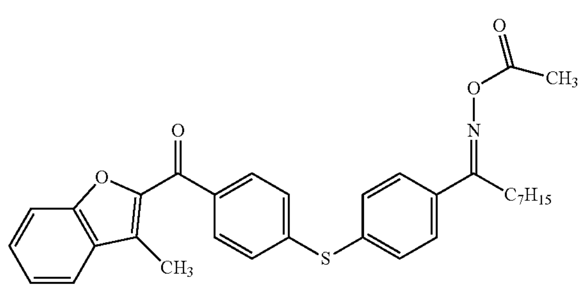 | 0.84-0.92 (t, 3H), 1.20-1.44 (m, 8H), 1.50-1.60 (m, 2H), 2.27 (s, 3H), 2.66 (s, 3H), 2.80-2.90 (t, 2H), 7.30-8.10 (m, 12H) |
| OE23 | 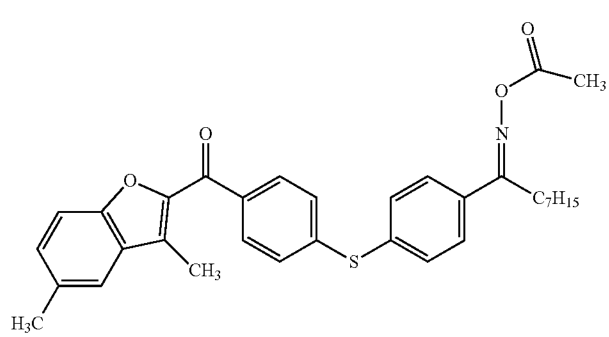 | 0.82-0.92 (t, 3H), 1.22-1.40 (m, 8H), 1.52-1.62 (m, 2H), 2.27 (s, 3H), 2.49 (s, 3H), 2.63 (s, 3H), 2.80-2.90 (t, 2H), 7.28-8.06 (m, 11H) |

TABLE 1-continued

| Oxime Ester | Structure | $^1$H NMR in CDCl$_3$ |
|---|---|---|
| OE24 | 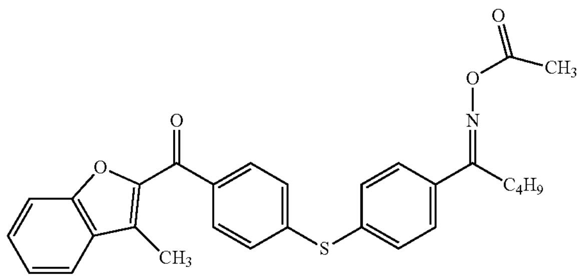 | 0.92-0.98 (t, 3H), 1.35-1.46 (m, 2H), 1.52-1.60 (m, 2H), 2.27 (s, 3H), 2.65 (s, 3H), 2.80-2.88 (t, 2H), 7.32-8.06 (m, 12H) |
| OE25 | 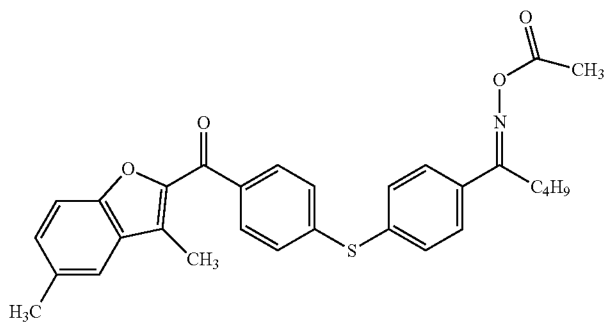 | 0.92-0.98 (t, 3H), 1.36-1.46 (m, 2H), 1.52-1.60 (m, 2H), 2.27 (s, 3H), 2.49 (s, 3H), 2.63 (s, 3H), 2.82-2.88 (t, 2H), 7.28-8.06 (m, 11H) |
| OE26 | 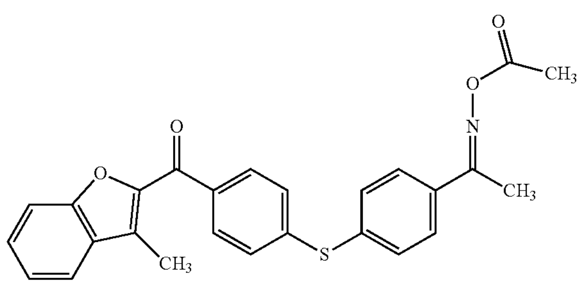 [SMILES: CC(=O)ON=C(C)c1ccc(Sc2ccc(C(=O)c3oc4ccccc4c3C)cc2)cc1] | 2.28 (s, 3H), 2.41 (s, 3H), 2.66 (s, 3H), 2.80-2.90 (t, 2H), 7.32-8.06 (m, 12H) |
| OE27 | 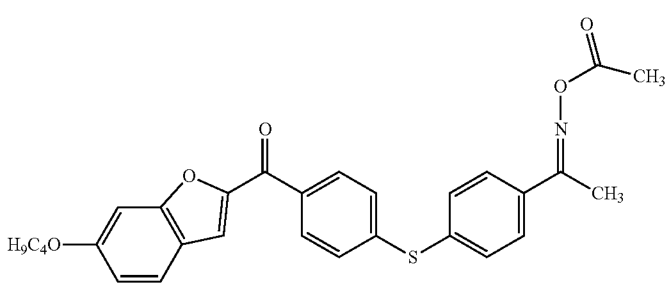 | 0.96-1.04 (t, 3H), 1.48-1.56 (, 2H), 1.78-1.86 (m, 2H), 2.28 (s, 3H), 2.41 (s, 3H), 4.00-4.06 (t, 2H), 6.94-7.98 (m, 12H) |
| OE28 | 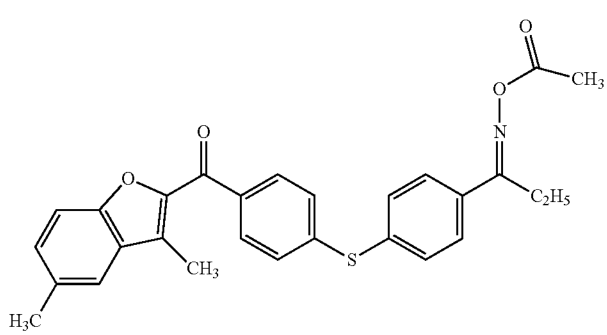 | 1.18-1.24 (t, 3H), 2.28 (s, 3H), 2.49 (s, 3H), 2.63 (s, 3H), 2.82-2.90 (t, 2H), 7.38-8.04 (m, 11H) |

TABLE 1-continued

| Oxime Ester | Structure | $^1$H NMR in CDCl$_3$ |
|---|---|---|
| OE29 | 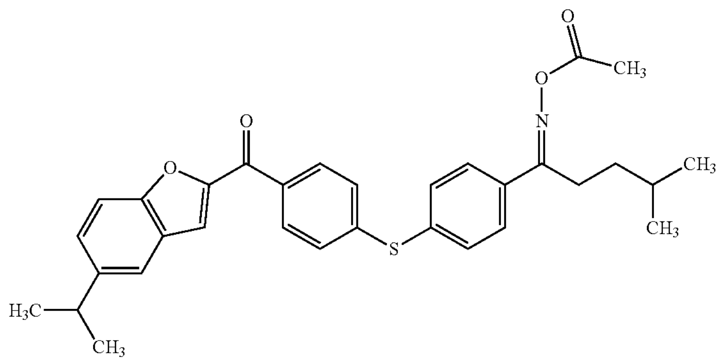 [SMILES: CC(=O)ON=C(CCC(C)C)c1ccc(Sc2ccc(C(=O)c3cc4cc(C(C)C)ccc4o3)cc2)cc1] | 0.92-0.98 (d, 6H), 1.26-1.32 (d, 6H), 1.42-1.50 (m, 2H), 1.60-1.70 (m, 1H), 2.27 (s, 3H), 2.80-2.88 (m, 2H), 2.98-3.08 (m, 1H), 7.36-8.01 (m, 12H) |
| OE30 | 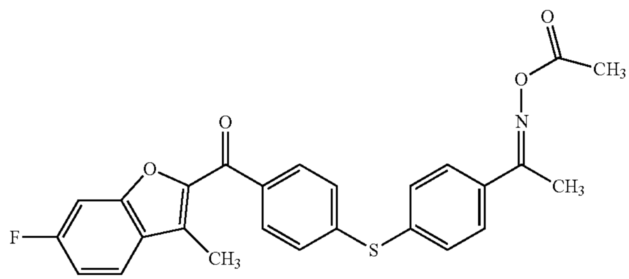 [SMILES: CC(=O)ON=C(C)c1ccc(Sc2ccc(C(=O)c3oc4cc(F)ccc4c3C)cc2)cc1] | 2.28 (s, 3H), 2.41 (s, 3H), 2.64 (s, 3H), 7.08-8.04 (m, 11H) |
| OE31 | 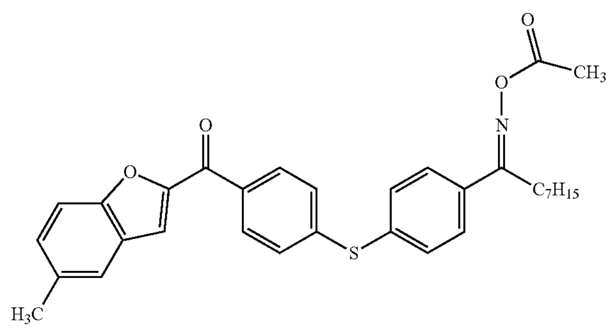 | 0.84-0.92 (t, 3H), 1.22-1.40 (m, 8H), 1.52-1.62 (m, 2H), 2.27 (s, 3H), 2.80-2.88 (t, 2H), 7.20-8.02 (m, 12H) |
| OE32 | mixture of E/Z form | 0.82-0.98 (d, 6H), 1.36-1.70 (m, 3H), 2.05-2.27 (m, 3H), 2.66-2.86 (m, 2H), 7.31-8.06 (m, 13H), |
| OE33 | 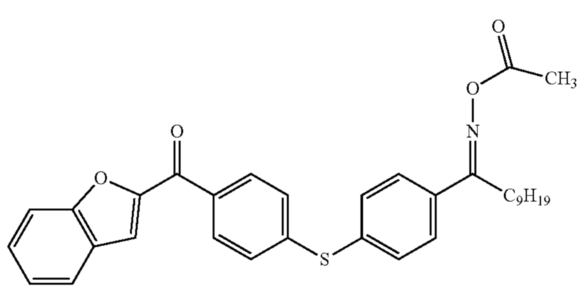 | 0.82-0.90 (t, 3H), 1.20-1.40 (m, 12H), 1.50-1.60 (m, 2H), 2.27 (s, 3H), 2.80-2.90 (t, 2H), 7.31-8.02 (m, 13H) |

TABLE 1-continued

| Oxime Ester | Structure | $^1$H NMR in CDCl$_3$ |
|---|---|---|
| OE34 | 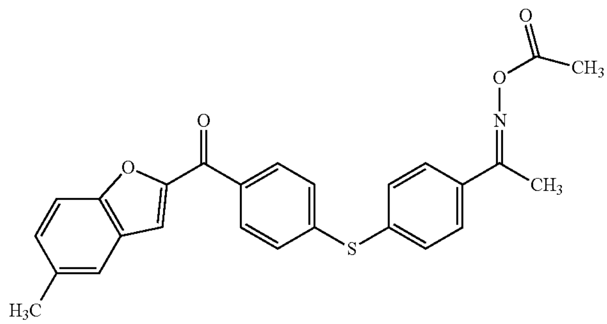 [SMILES: CC(=O)ON=C(C)c1ccc(Sc2ccc(C(=O)c3cc4cc(C)ccc4o3)cc2)cc1] | 2.28 (s, 3H), 2.41 (s, 3H), 7.20-8.01 (m, 14H) |
| OE35 | 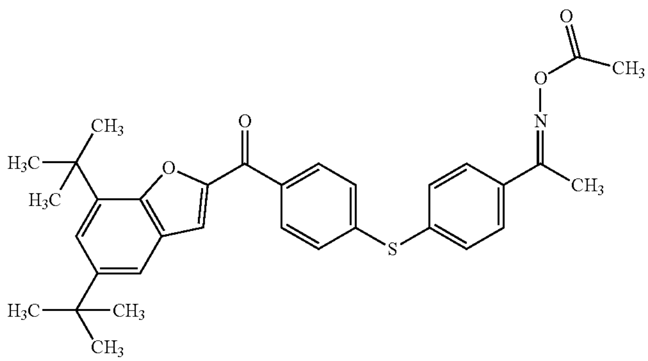 [SMILES: CC(=O)ON=C(C)c1ccc(Sc2ccc(C(=O)c3cc4cc(C(C)(C)C)cc(C(C)(C)C)c4o3)cc2)cc1] | 1.39 (s, 9H), 1.55 (s, 9H), 2.28 (s, 3H), 2.41 (s, 3H), 2.64 (s, 3H), 7.36-8.06 (m, 11H) |
| OE36 | 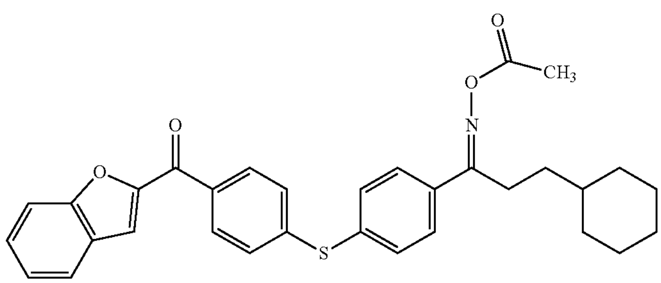 [SMILES: CC(=O)ON=C(CCC1CCCCC1)c1ccc(Sc2ccc(C(=O)c3cc4ccccc4o3)cc2)cc1] | 0.84-0.98 (m, 2H), 1.08-1.38 (m, 4H), 1.40-1.50 (m, 2H), 1.60-1.78 (m, 5H), 2.27 (s, 3H), 2.80-2.88 (m, 2H), 7.31-8.01 (m, 13H) |
| OE37 | 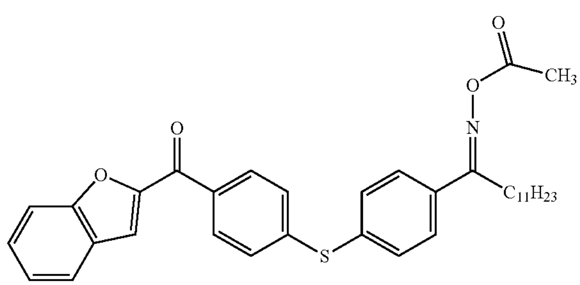 | 0.82-0.92 (t, 3H), 1.18-1.38 (m, 16H), 1.50-1.60 (m, 2H), 2.27 (s, 3H), 2.80-2.90 (t, 2H), 7.31-8.02 (m, 13H) |
| OE38 | 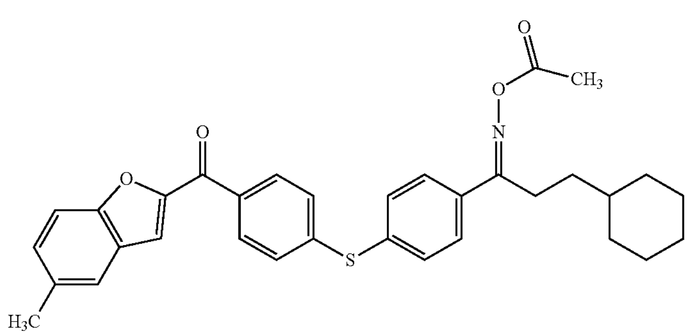 [SMILES: CC(=O)ON=C(CCC1CCCCC1)c1ccc(Sc2ccc(C(=O)c3cc4cc(C)ccc4o3)cc2)cc1] | 0.84-0.98 (m, 2H), 1.08-1.38 (m, 4H), 1.40-1.50 (m, 2H), 1.60-1.78 (m, 5H), 2.27 (s, 3H), 2.80-2.88 (m, 2H), 7.20-7.81 (m, 12H) |

TABLE 1-continued

| Oxime Ester | Structure | $^1$H NMR in CDCl$_3$ |
|---|---|---|
| OE39 | 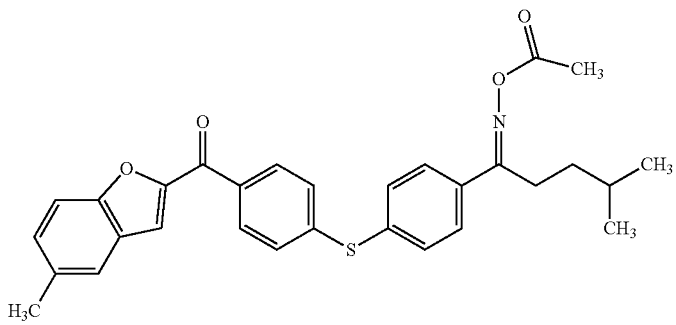 [SMILES: CC(=O)ON=C(CCC(C)C)c1ccc(Sc2ccc(C(=O)c3cc4cc(C)ccc4o3)cc2)cc1] | 0.94-0.98 (d, 6H), 1.40-1.50 (m, 2H), 1.60-1.70 (m, 1H), 2.27 (s, 3H), 2.80-2.88 (m, 2H), 7.21-8.02 (m, 12H), |
| OE40 | 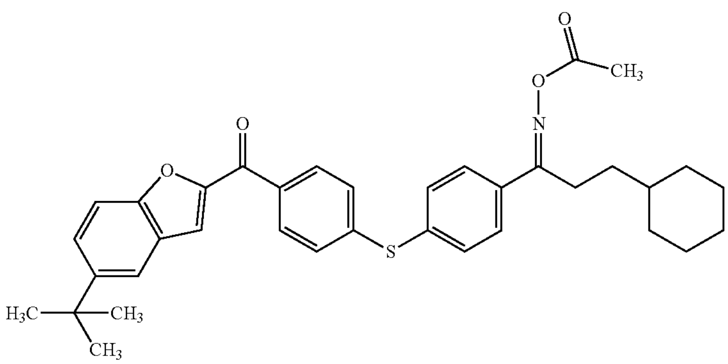 [SMILES: CC(=O)ON=C(CCC1CCCCC1)c1ccc(Sc2ccc(C(=O)c3cc4cc(C(C)(C)C)ccc4o3)cc2)cc1] | 0.84-0.98 (m, 2H), 1.08-1.38 (m, 4H), 1.40-1.50 (m, 2H), 1.4 (s, 9H), 1.60-1.78 (m, 5H), 2.27 (s, 3H), 2.80-2.88 (m, 2H), 7.31-8.00 (m, 12H) |
| OE41 | 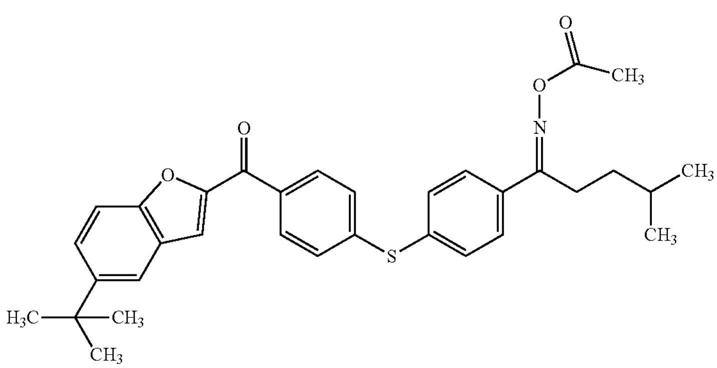 [SMILES: CC(=O)ON=C(CCC(C)C)c1ccc(Sc2ccc(C(=O)c3cc4cc(C(C)(C)C)ccc4o3)cc2)cc1] | 0.94-0.98 (d, 6H), 1.39 (s, 9H), 1.40-1.50 (m, 2H), 1.60-1.70 (m, 1H), 2.27 (s, 3H), 2.80-2.88 (m, 2H), 7.32-8.01 (m, 12H) |
| OE42 | 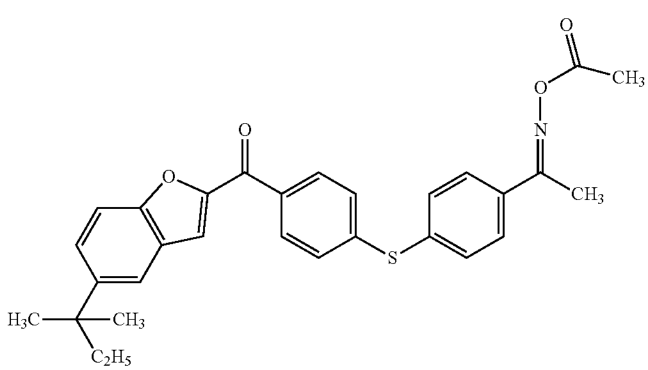 [SMILES: CCC(C)(C)c1ccc2oc(C(=O)c3ccc(Sc4ccc(C(C)=NOC(C)=O)cc4)cc3)cc2c1] | 0.64-0.74 (t, 3H), 1.35 (s, 6H), 1.66-1.74 (q, 2H), 2.28 (s, 3H), 2.41 (s, 3H), 7.35-8.02 (m, 12H) |

TABLE 1-continued
| Oxime Ester | Structure | $^1$H NMR in CDCl$_3$ |
|---|---|---|
| OE43 | 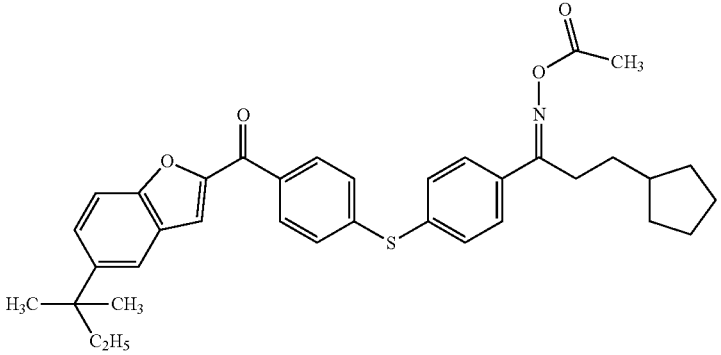 [SMILES: CCC(C)(C)c1ccc2oc(C(=O)c3ccc(Sc4ccc(C(CCC5CCCC5)=NOC(C)=O)cc4)cc3)cc2c1] | 0.64-0.74 (t, 3H), 1.08-1.20 (m, 2H), 1.34 (s, 6H), 1.50-1.88 (m, 11H), 2.27 (s, 3H), 2.80-2.90 (t, 2H), 7.36-8.02 (m, 12H) |
| OE44 | 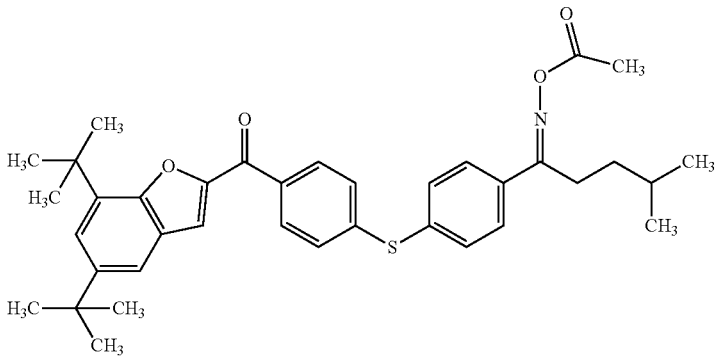 [SMILES: CC(=O)ON=C(CCC(C)C)c1ccc(Sc2ccc(C(=O)c3cc4cc(C(C)(C)C)cc(C(C)(C)C)c4o3)cc2)cc1] | 0.94-0.98 (d, 6H), 1.39 (s, 9H), 1.40-1.50 (m, 2H), 1,54 (s, 9H), 1.60-1.70 (m, 1H), 2.27 (s, 3H), 2.80-2.88 (m, 2H), 7.32-8.01 (m, 11H) |
| OE45 | 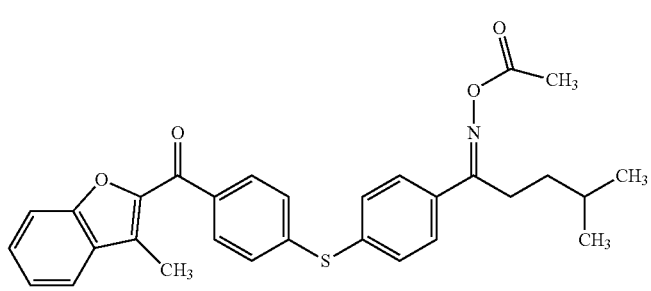 [SMILES: CC(=O)ON=C(CCC(C)C)c1ccc(Sc2ccc(C(=O)c3oc4ccccc4c3C)cc2)cc1] | 0.94-0.98 (d, 6H), 1.40-1.50 (m, 2H), 1.60-1.70 (m, 1H), 2.27 (s, 3H), 2.66 (s, 3H), 2.80-2.88 (m, 2H), 7.31-8.06 (m, 12H) |
| OE46 | 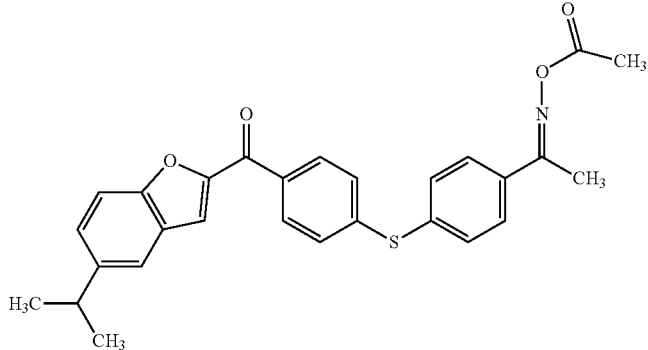 [SMILES: CC(=O)ON=C(C)c1ccc(Sc2ccc(C(=O)c3cc4cc(C(C)C)ccc4o3)cc2)cc1] | 1.28-1.36 (d, 6H), 2.27 (s, 3H), 2.41 (s, 3H), 2.98-3.08 (m, 1H), 7.34-8.00 (m, 12H) |

TABLE 1-continued
| Oxime Ester | Structure | $^1$H NMR in CDCl$_3$ |
|---|---|---|
| OE47 | 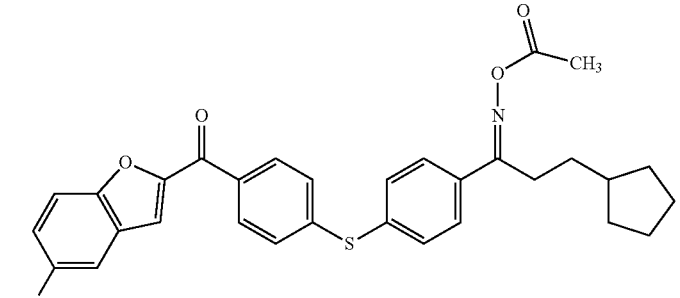 | 1.05-1.20 (t, 2H), 1.50-1.70 (m, 6H), 1.75-1.86 (m, 3H), 2.27 (s, 3H), 2.49 (s, 3H), 2.80-2.89 (t, 2H), 7.32-8.10 m, 12H) |
| OE48 | 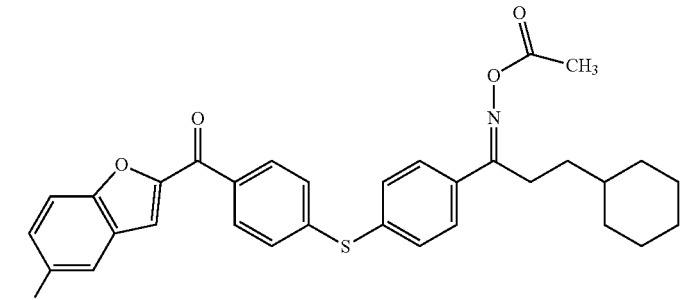 | 0.84-0.98 (m, 2H), 1.08-1.38 (m, 4H), 1.40-1.50 (m, 2H), 1.60-1.78 (m, 5H), 2.27 (s, 3H), 2.48 (s, 3H), 2.80-2.88 (m, 2H), 7.34-8.05 (m, 12H) |
| OE49 | 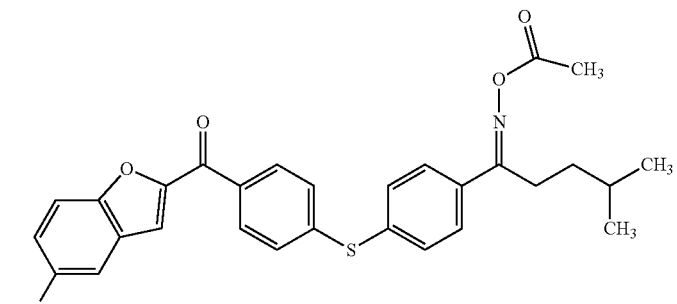 | 0.94-0.98 (d, 6H), 1.40-1.50 (m, 2H), 1.60-1.70 (m, 1H), 2.27 (s, 3H), 2.48 (s, 3H), 2.80-2.88 (m, 2H), 7.34-8.05 (m, 12H) |
| OE50 | 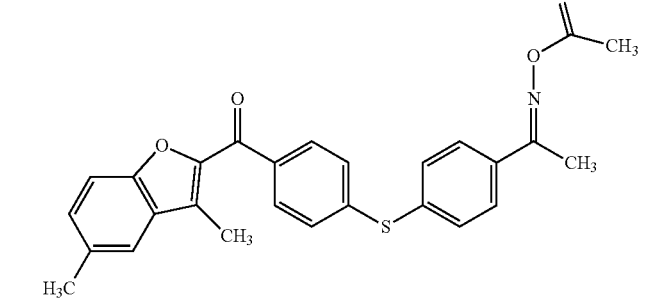 | 2.27 (s, 3H), 2.41 (s, 3H), 2.50 (s, 3H), 2.51 (s, 3H), 7.30-8.02 (m, 11H) |

TABLE 1-continued

| Oxime Ester | Structure | $^1$H NMR in CDCl$_3$ |
|---|---|---|
| OE51 | 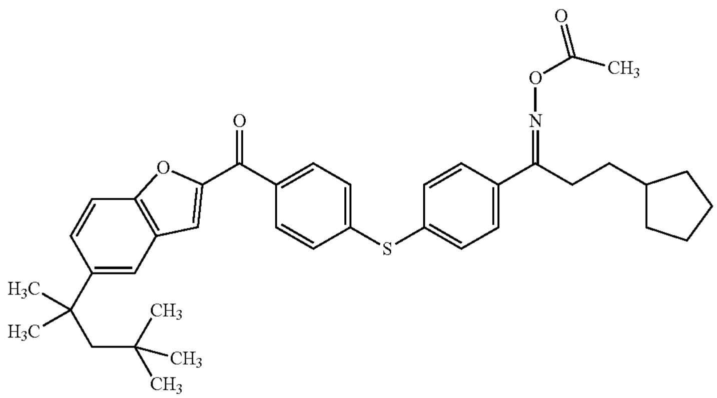 [SMILES: CC(=O)ON=C(CCC1CCCC1)c1ccc(Sc2ccc(C(=O)c3cc4cc(C(C)(C)CC(C)(C)C)ccc4o3)cc2)cc1] | 0.73 (s, 9H), 1.05-1.20 (t, 2H), 1.46 (s, 6H), 1.75-1.86 (m, 3H), 1.50-1.70 (m, 6H), , 2.27 (s, 3H) 2.80-2.89 (t, 2H), 7.32-8.10 m, 12H) |
| OE52 | 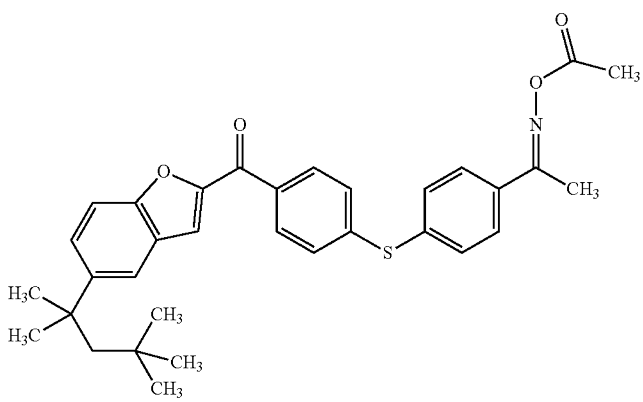 [SMILES: CC(=O)ON=C(C)c1ccc(Sc2ccc(C(=O)c3cc4cc(C(C)(C)CC(C)(C)C)ccc4o3)cc2)cc1] | 0.73 (s, 9H), 1.45 (s, 6H), 1.82 (s, 2H), 2.30 (s, 3H) 2.43 (s, 3H), 7.40-8.06 (m, 12H) |
| OE53 | 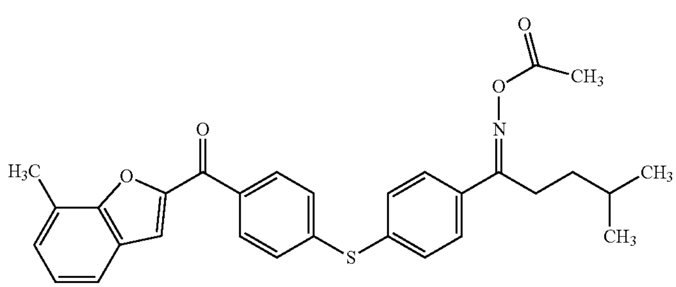 [SMILES: CC(=O)ON=C(CCC(C)C)c1ccc(Sc2ccc(C(=O)c3cc4cccc(C)c4o3)cc2)cc1] | 0.94-0.98 (d, 6H), 1.40-1.50 (m, 2H), 1.60-1.70 (m, 1H), 2.29 (s, 3H), 2.63 (s, 3H), 2.80-2.88 (m, 2H), 7.25-8.08 (m, 12H) |
| OE54 | 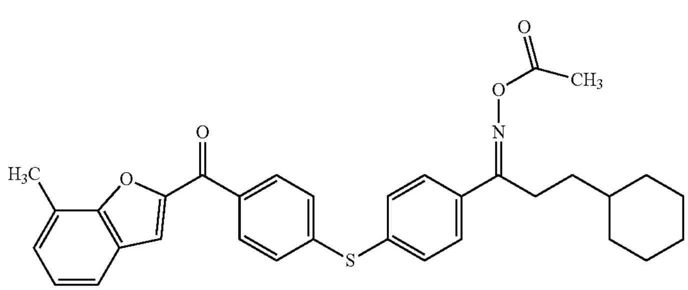 [SMILES: CC(=O)ON=C(CCC1CCCCC1)c1ccc(Sc2ccc(C(=O)c3cc4cccc(C)c4o3)cc2)cc1] | 0.84-0.98 (m, 2H), 1.08-1.38 (m, 4H), 1.40-1.50 (m, 2H), 1.60-1.78 (m, 5H), 2.29 (s, 3H), 2.63 (s, 3H), 2.80-2.88 (m, 2H), 7.25-8.08 (m, 12H) |

TABLE 1-continued

| Oxime Ester | Structure | $^1$H NMR in CDCl$_3$ |
|---|---|---|
| OE55 | 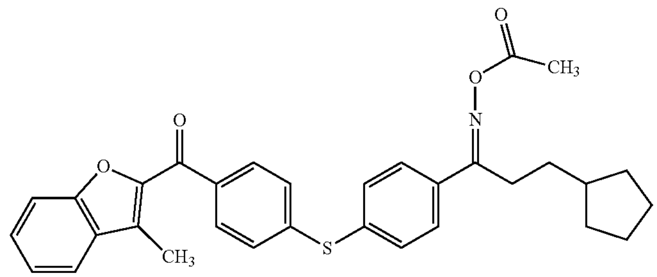 [SMILES: CC(=O)ON=C(CCC1CCCC1)c1ccc(Sc2ccc(C(=O)c3oc4ccccc4c3C)cc2)cc1] | 1.05-1.20 (t, 2H), 1.50-1.70 (m, 6H), 1.75-1.86 (m, 3H), 2.27 (s, 3H), 2.66 (s, 3H), 2.80-2.89 (t, 2H), 7.32-8.08 m, 12H) |
| OE56 | 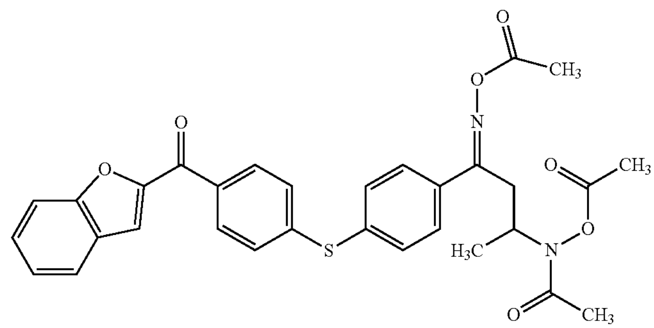 [SMILES: CC(=O)ON=C(CC(C)N(OC(C)=O)C(C)=O)c1ccc(Sc2ccc(C(=O)c3cc4ccccc4o3)cc2)cc1] | 1.16-1.22 (d, 3H), 1.90 (s, 3H), 2.28 (s, 3H), 2.30 (s, 3H), 3.07-3.30 (m, 2H), 4.80-4.95 (m, 1H), 7.32-8.04 (m, 13H) |
| OE57 | 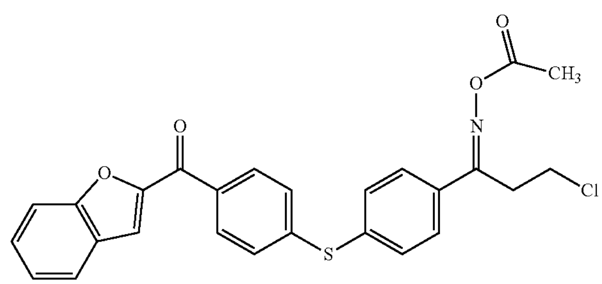 [SMILES: CC(=O)ON=C(CCCl)c1ccc(Sc2ccc(C(=O)c3cc4ccccc4o3)cc2)cc1] | 2.02-2.16 (m, 2H), 2.27 (s, 3H), 3.30-3.06 (m, 2H), 3.58-3.64 (t, 2H), 7.32-8.04 (m, 13H) |
| OE58 | 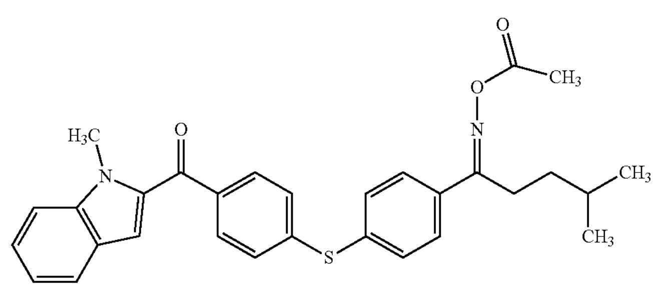 [SMILES: CC(=O)ON=C(CCC(C)C)c1ccc(Sc2ccc(C(=O)c3cc4ccccc4n3C)cc2)cc1] | 0.94-0.98 (d, 6H), 1.40-1.50 (m, 2H), 1.60-1.70 (m, 1H), 2.27 (s, 3H), 2.80-2.88 (m, 2H), 4.10 (s, 3H), 7.15-7.88 (m, 13H) |
| OE59 | 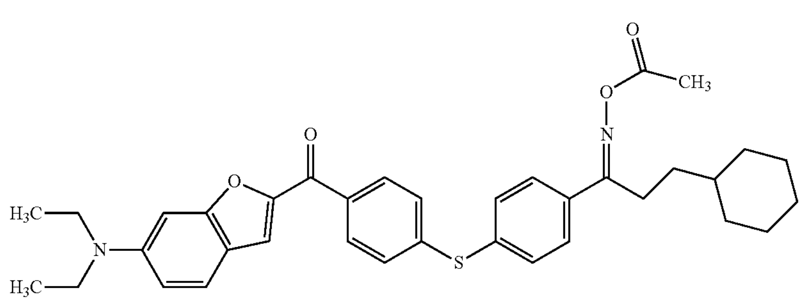 [SMILES: CCN(CC)c1ccc2cc(C(=O)c3ccc(Sc4ccc(C(CCC5CCCCC5)=NOC(C)=O)cc4)cc3)oc2c1] | 0.82-1.80 (m, 17H), 2.26 (s, 3H), 2.78-2.86 (t, 2H), 3.40-3.50 (q, 4H), 6.75-7.96 (m, 12H) |

TABLE 1-continued

| Oxime Ester | Structure | ¹H NMR in CDCl₃ |
|---|---|---|
| OE60 | 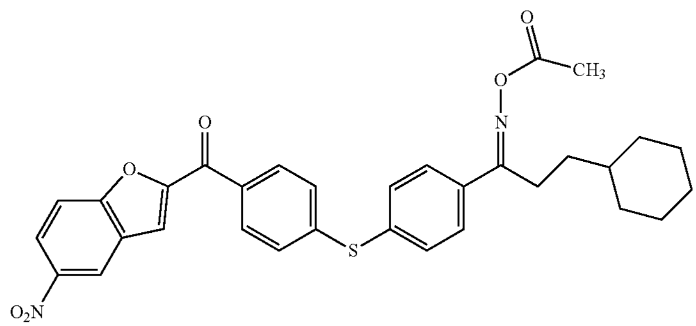 [SMILES: CC(=O)ON=C(CCC1CCCCC1)c1ccc(Sc2ccc(C(=O)c3cc4cc([N+](=O)[O-])ccc4o3)cc2)cc1] | 0.84-0.98 (m, 2H), 1.08-1.38 (m, 4H), 1.40-1.50 (m, 2H), 1.60-1.78 (m, 5H), 2.27 (s, 3H), 2.80-2.88 (m, 2H), 7.34-8.70 (m, 12H) |
| OE61 | 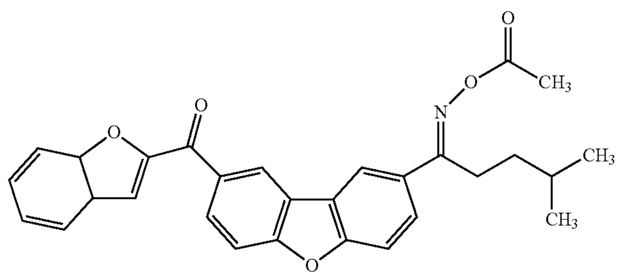 | 0.94-0.98 (d, 6H), 1.40-1.50 (m, 2H), 1.60-1.70 (m, 1H), 2.29 (s, 3H), 2.90-3.00 (t, 2H), 7.24-8.78 (m, 11H) |
| OE62 | 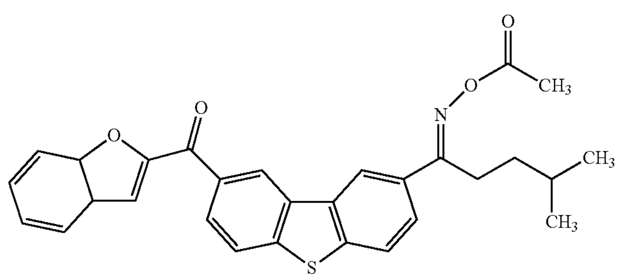 [SMILES: CC(=O)O/N=C(\CCC(C)C)c1ccc2sc3ccc(C(=O)C4=CC5C=CC=CC5O4)cc3c2c1] | 0.94-0.98 (d, 6H), 1.40-1.50 (m, 2H), 1.60-1.70 (m, 1H), 2.29 (s, 3H), 2.90-3.00 (t, 2H), 7.32-8.92 (m, 11H) |
| OE63 | 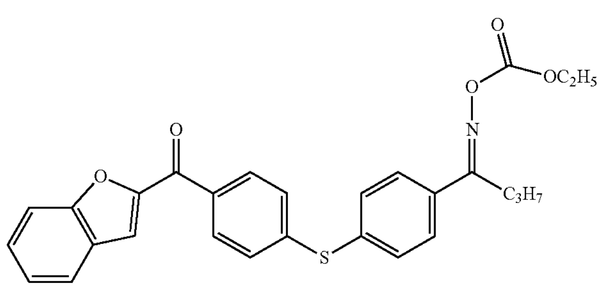 | 0.82-0.92 (t, 3H), 1.18-1.43 (t, 3H), 1.50-1.62 (m, 2H), 2.82-2.90 (t, 2H), 4.33-4.40 (q, 2H), 7.32-8.04 (m, 13H) |
| OE64 | 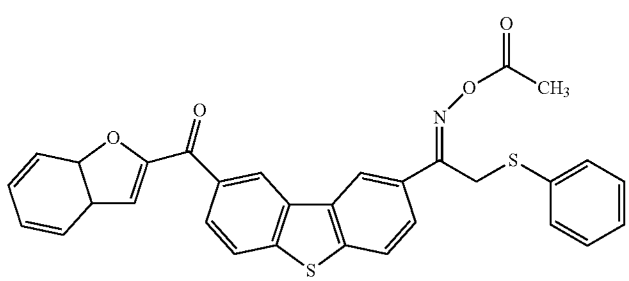 [SMILES: CC(=O)O/N=C(\CSc1ccccc1)c1ccc2sc3ccc(C(=O)C4=CC5C=CC=CC5O4)cc3c2c1] | 2.01 (s, 3H), 4.16 (s, 2H), 7.28-8.04 (m, 18H) |

TABLE 1-continued

| Oxime Ester | Structure | $^1$H NMR in CDCl$_3$ |
|---|---|---|
| OE65 | 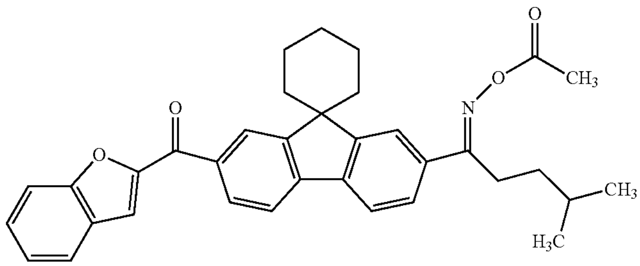 [SMILES: CC(=O)O/N=C(\CCC(C)C)c1ccc2c(c1)C1(CCCCC1)c1cc(C(=O)c3cc4ccccc4o3)ccc1-2] | 2.27 (s, 3H), 3.05-3.10 (t, 2H), 4.30-4.35 (t, 2H), 6.98-8.35 (m, 12H) |
| OE66 | 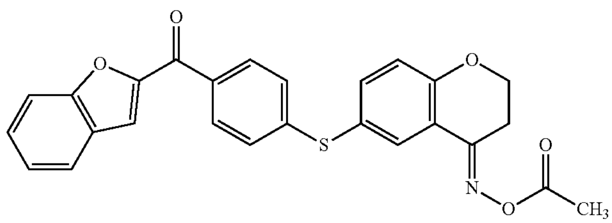 [SMILES: CC(=O)O/N=C1\CCOc2ccc(Sc3ccc(C(=O)c4cc5ccccc5o4)cc3)cc21] | 2.27 (s, 3H), 3.05-3.10 (t, 2H), 4.30-4.35 (t, 2H), 6.98-8.35 (m, 12H) |
| OE67 | 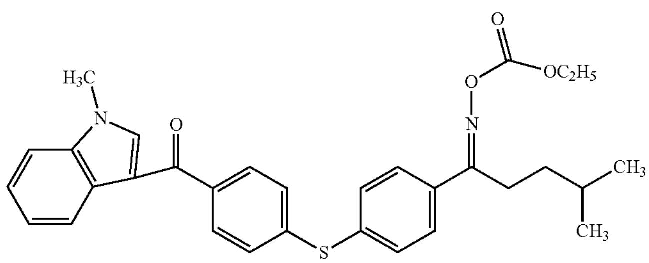 [SMILES: CCOC(=O)ON=C(CCC(C)C)c1ccc(Sc2ccc(C(=O)c3cn(C)c4ccccc34)cc2)cc1] | 0.94-0.98 (d, 6H), 1.40-1.50 (m, 2H), 1.60-1.70 (m, 1H), 2.27 (s, 3H), 2.80-2.88 (m, 2H), 3.87 (s, 3H), 7.34-8.44 (m, 13H) |
| OE68 | 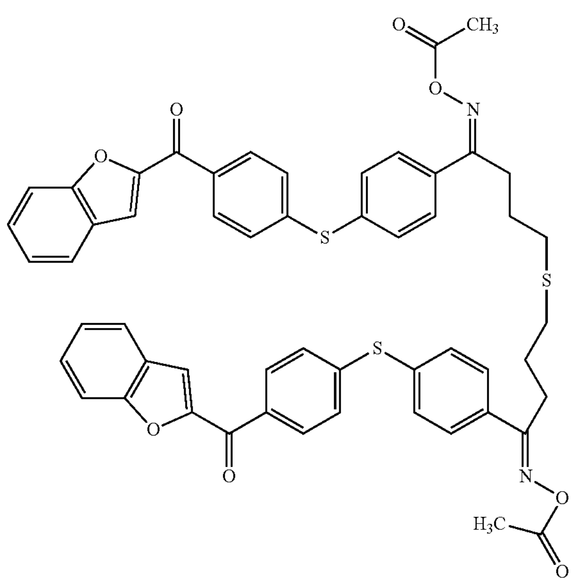 [SMILES: CC(=O)O/N=C(/CCCSCCC/C(=N\OC(C)=O)c1ccc(Sc2ccc(C(=O)c3cc4ccccc4o3)cc2)cc1)c1ccc(Sc2ccc(C(=O)c3cc4ccccc4o3)cc2)cc1] | 1.82-1.98 (m, 4H), 2.28 (s, 6H), 2.64-2.74 (t, 4H), 2.92-3.00 (t, 4H), 7.30-8.04 (m, 26H) |

TABLE 1-continued

| Oxime Ester | Structure | $^1$H NMR in CDCl$_3$ |
| --- | --- | --- |
| OE69 | 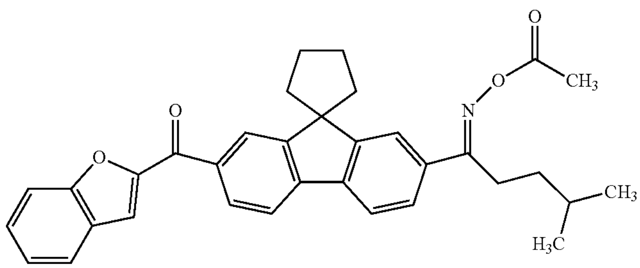 [SMILES: CC(=O)O/N=C(\CCC(C)C)c1ccc2c(c1)C1(CCCC1)c1cc(C(=O)c3cc4ccccc4o3)ccc1-2] | 0.85-1.02 (m, 6H), 1.36-1.72 (m, 3H), 2.06-2.18 (m, 8H), 2.29 (s, 3H), 2.70-2.92 (m, 2H), 7.28-8.40 (m, 11H) |
| OE70 | 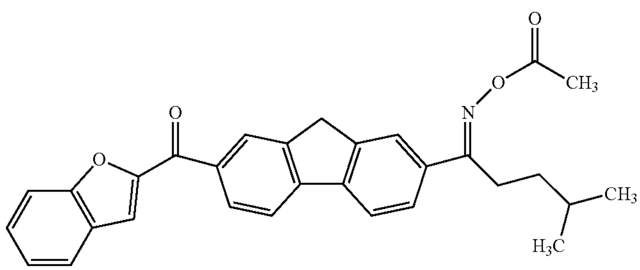 [SMILES: CC(=O)O/N=C(\CCC(C)C)c1ccc2c(c1)Cc1cc(C(=O)c3cc4ccccc4o3)ccc1-2] | 0.85-1.02 (m, 6H), 1.36-1.42 (m, 3H), 2.29 (s, 3H), 2.70-2.92 (m, 2H), 4.08 (s, 2H), 7.28-8.30 (m, 11H |
| OE71 | 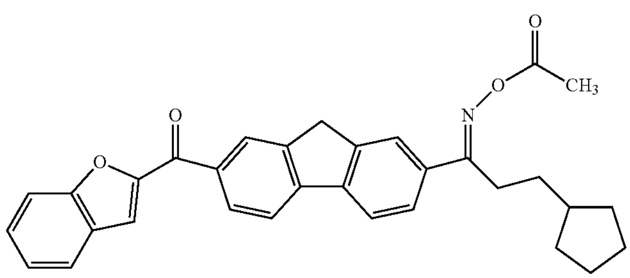 [SMILES: CC(=O)O/N=C(\CCC1CCCC1)c1ccc2c(c1)Cc1cc(C(=O)c3cc4ccccc4o3)ccc1-2] | 0.85-1.20 (m, 2H), 1.50-1.70 (m, 6H), 1.75-1.86 (m, 3H), 2.29 (s, 3H), 2.70-2.92 (m, 2H), 4.08 (s, 2H), 7.28-8.30 (m, 11H) |
| OE72 | 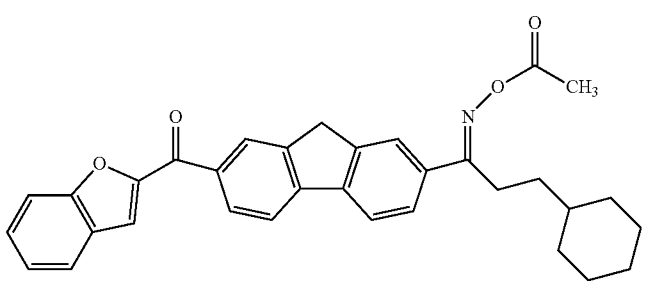 [SMILES: CC(=O)O/N=C(\CCC1CCCCC1)c1ccc2c(c1)Cc1cc(C(=O)c3cc4ccccc4o3)ccc1-2] | 0.85-0.98 (m, 2H), 1.08-1.38 (m, 4H), 1.40-1.50 (m, 2H), 1.60-1.78 (m, 5H), 2.27 (s, 3H), 2.80-2.88 (m, 2H), 4.08 (s, 2H), 7.28-8.30 (m, 11H) |
| OE73 | 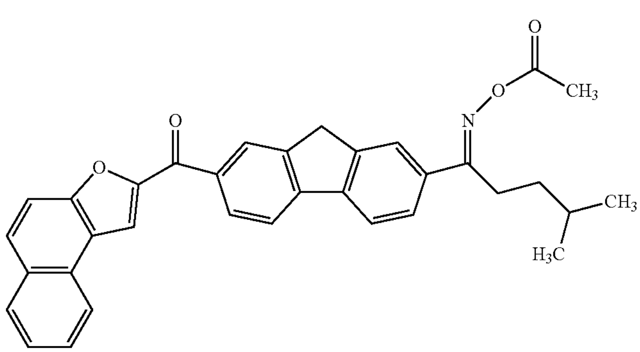 [SMILES: CC(=O)O/N=C(\CCC(C)C)c1ccc2c(c1)Cc1cc(C(=O)c3cc4c(ccc5ccccc54)o3)ccc1-2] | 0.85-1.02 (m, 6H), 1.36-1.42 (m, 3H), 2.29 (s, 3H), 2.70-2.92 (m, 2H), 4.08 (s, 2H), 7.28-8.22 (m, 13H) |

TABLE 1-continued

| Oxime Ester | Structure | $^1$H NMR in CDCl$_3$ |
|---|---|---|
| OE74 | 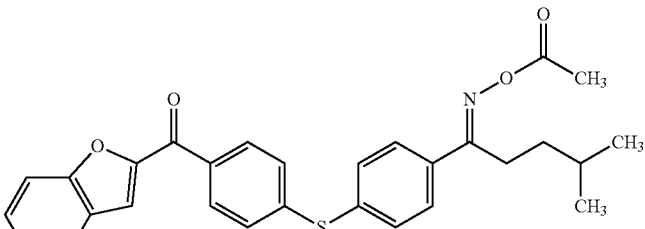<br>E-form | 0.92-0.98 (d, 6H), 1.42-1.50 (m, 2H), 1.60-1.70 (m, 1H), 2.27 (s, 3H), 2.80-2.88 (m, 2H), 7.31-8.02 (m, 13H) |
| OE75 | 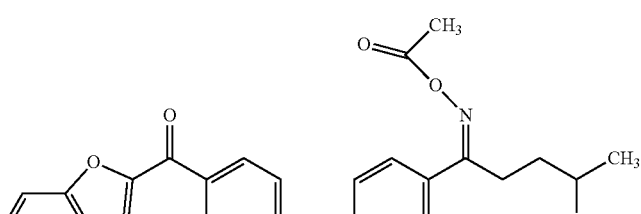<br>Z form | 0.82-0.86 (d, 6H), 1.32-1.50 (m, 3H), 2.05 (s, 3H), 2.66-2.72 (t, 2H), 7.31-8.06 (m, 13H) |

APPLICATION EXAMPLES

Preparation of Poly(benzylmethacrylate-co-methacrylic acid)

24 g of benzylmethacrylate, 6 g of methacrylic acid and 0.525 g of azobisisobutyronitrile (AIBN) are dissolved in 90 ml of propylene glycol 1-monomethyl ether 2-acetate (PG-MEA). The resulting reaction mixture is placed in a preheated oil bath at 80° C. After stirring for 5 hours at 80° C. under nitrogen, the resulting viscous solution is cooled to room temperature and used without further purification. The solid content is about 25%.

Sensitivity Test A

A photocurable composition for a sensitivity test is prepared by mixing the following components:
  100.0 parts by weight of copolymer of benzylmethacrylate and methacrylic acid (benzylmethacrylate: methacrylic acid=80:20 by weight) 25% propylene glycol 1-monomethyl ether 2-acetate (PGMEA) solution, prepared in above example
  25.0 parts by weight of dipentaerythritol hexaacrylate ((DPHA), provided by SIGMA-ALDRICH),
  1.0 parts by weight of the photoinitiator (PI), and
  75.0 parts by weight of PGMEA All operations are carried out under yellow light. The compositions are applied to an aluminum plate using an electric applicator with a wire wound bar. The solvent is removed by heating at 80° C. for 10 minutes in a convection oven. The thickness of the dry film is approximately 2 p.m. A standardized test negative film with 21 steps of different optical density (Stouffer step wedge) is placed with an air gap of around 300 μm between the film and the resist. A glass plate is placed over the negative film to fix the masks with 21 steps. Exposure is carried out using a 250 W super high pressure mercury lamp (USHIO, USH-250BY) at a distance of 20 cm. A total exposure dose measured by an optical power meter (USHIO, UNIMETER UIT-150-A with UVD-S365 detector) on the glass plate is 250 mJ/cm$^2$. After exposure, the exposed film is developed with an alkaline solution (5% aqueous solution of DL-A4, Yokohama Yushi) for 120 sec. at 28° C. by using a spray type developer (AD-1200, Takizawa Sangyo). The sensitivity of the initiator used is characterized by indicating the highest number of the step remained (i.e. polymerized) after developing. The higher the number of steps, the more sensitive is the initiator tested. The results are listed in table 2.

TABLE 2

| | Photo sensitivity | |
|---|---|---|
| Example No. | PI | No. of steps |
| A1 | OE-1 | 17 |
| A2 | OE-2 | 17 |
| A3 | OE-3 | 17 |
| A5 | OE-5 | 14 |
| A6 | OE-6 | 16 |
| A7 | OE-7 | 16 |
| A8 | OE-8 | 16 |
| A9 | OE9 | 16 |
| A10 | OE10 | 15 |
| A11 | OE12 | 16 |
| A12 | OE13 | 15 |
| A13 | OE14 | 16 |
| A14 | OE15 | 16 |
| A15 | OE16 | 13 |
| A16 | OE17 | 16 |
| A17 | OE18 | 15 |
| A18 | OE19 | 18 |
| A19 | OE20 | 16 |
| A20 | OE21 | 17 |
| Comparative example 1 | OE-R1 | 12 |

OE-R1 is

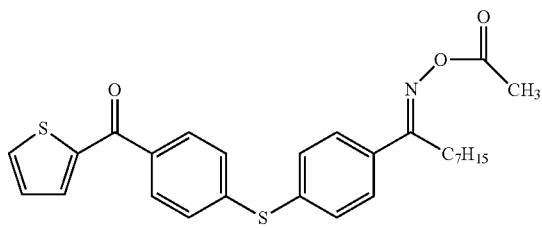

as disclosed in WO04/050653, Example 6

As shown in table 2, the compounds according to the invention show higher photosensitivity than the comparative compound.

Sensitivity Test B

A photocurable composition for a sensitivity test is prepared by mixing the following components:
- 88.6 parts by weight solvent (PGMEA)
- 86.1 parts by weight alkaline developable binder, 29.0% solution (Ripoxy SPC-1000, provided by Showa High-polymer)
- 25.3 parts by weight multifunctional acrylate (DPHA, provided by SIGMA-ALDRICH)
- 1.0 parts by weight photoinitiator (PI)

All operations are carried out under yellow light. The compositions are applied to a silicon wafer using a spin-coater. The solvent is removed by heating at 80° C. for 10 minutes in a convection oven. The thickness of the dry film is approximately 2 p.m. A standardized test negative film with 30 steps of different optical density (FUJIFILM Imaging Systems, Gray step chart) is placed with an air gap of around 300 μm between the film and the resist. A silicon wafer is placed over the negative film to fix the masks with 30 steps. Exposure is carried out using a 250 W super high pressure mercury lamp (USHIO, USH-250BY) at a distance of 20 cm. A total exposure dose measured by an optical power meter (USHIO, UNIMETER UIT-150-A with UVD-5365 detector) on the silicon wafer is 150 mJ/cm². After exposure, the exposed film is developed with an alkaline solution (5% aqueous solution of DL-A4, Yokohama Yushi) for 60 sec. at 28° C. by using a spray type developer (AD-1200, Takizawa Sangyo). The necessary UV dose is corresponded to UV dose of full curing (i.e. the pattern is not dissolved with the alkaline solution) after developing. The smaller the value of the dose, the more sensitive is the tested initiator. The results are listed in table 3.

TABLE 3

| Example No. | PI | Necessary UV dose for full cure [mJ/cm²] |
| --- | --- | --- |
| B1 | OE2 | 15.3 |
| B2 | OE3 | 17.6 |
| B3 | OE12 | 17.6 |
| B4 | OE13 | 24.3 |
| B5 | OE14 | 12.8 |
| B6 | OE15 | 15.4 |
| B7 | OE18 | 15.4 |
| B8 | OE19 | 9.0 |
| B9 | OE21 | 10.6 |
| B10 | OE22 | 20.7 |
| B11 | OE23 | 20.7 |
| B12 | OE24 | 15.4 |
| B13 | OE25 | 12.8 |
| B14 | OE26 | 12.8 |

TABLE 3-continued

| Example No. | PI | Necessary UV dose for full cure [mJ/cm²] |
| --- | --- | --- |
| B15 | OE27 | 10.6 |
| B16 | OE29 | 7.5 |
| B17 | OE30 | 12.8 |
| B18 | OE31 | 15.4 |
| B19 | OE32 | 9.0 |
| B20 | OE33 | 15.4 |
| B21 | OE34 | 15.4 |
| B22 | OE35 | 10.6 |
| B23 | OE36 | 9.0 |
| B24 | OE37 | 15.4 |
| B25 | OE38 | 12.8 |
| B26 | OE39 | 12.8 |
| B27 | OE40 | 10.6 |
| B28 | OE41 | 10.6 |
| B29 | OE42 | 12.8 |
| B30 | OE43 | 10.6 |
| B31 | OE44 | 10.6 |
| B32 | OE45 | 9.0 |
| B33 | OE46 | 17.6 |
| B34 | OE47 | 7.5 |
| B35 | OE48 | 10.6 |
| B36 | OE49 | 7.5 |
| B37 | OE50 | 17.6 |
| B38 | OE51 | 10.6 |
| B39 | OE52 | 20.7 |
| B40 | OE53 | 7.5 |
| B41 | OE54 | 9.0 |
| B42 | OE55 | 10.6 |
| B43 | OE57 | 17.6 |
| B44 | OE58 | 15.4 |
| B45 | OE60 | 10.6 |
| B46 | OE62 | 15.4 |
| B47 | OE65 | 9.0 |
| B48 | OE66 | 12.8 |
| B49 | OE67 | 20.7 |
| B50 | OE68 | 29.3 |
| B51 | OE69 | 7.5 |
| B52 | OE70 | 7.5 |
| Comparative example 2 | OE-R1 | 55.7 |

OE-R1 is Example 6 as disclosed in WO04/050653.

As shown in table 3, the compounds according to the invention show higher photosensitivity than the comparative compound.

The invention claimed is:

1. Compounds of formulae (I)

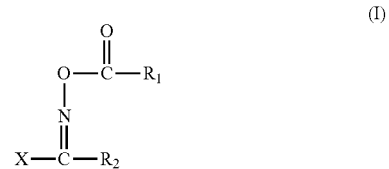

wherein
X is

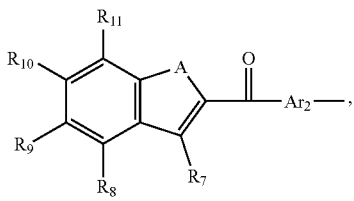

-continued

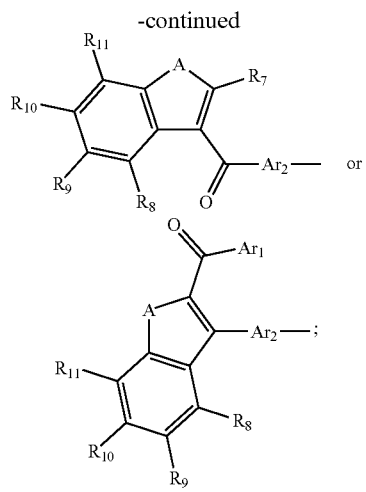

A is O, S, NR$_5$ or CR$_{16}$R$_{17}$;

R$_1$ is selected from: hydrogen, or C$_1$-C$_{20}$alkyl which is unsubstituted, or substituted by one or more substituents selected from the group consisting of halogen, OR$_3$, SR$_4$, NR$_5$R$_6$, CN, (CO)OR$_3$, (CO)NR$_5$R$_6$, C$_3$-C$_8$cycloalkyl, C$_3$-C$_8$cycloalkyl which is interrupted by one or more O, S, CO or NR$_5$, C$_6$-C$_{20}$aryl, C$_3$-C$_{20}$heteroaryl, C$_6$-C$_{20}$aroyl and C$_3$-C$_{20}$heteroarylcarbonyl, of which C$_6$-C$_{20}$aryl, C$_3$-C$_{20}$heteroaryl, C$_6$-C$_{20}$aroyl or C$_3$-C$_{20}$heteroarylcarbonyl is unsubstituted, or substituted by one or more halogen, phenyl, C$_1$-C$_{20}$alkylphenyl, C$_1$-C$_8$alkoxyphenyl, C$_1$-C$_4$haloalkyl, CN, NO$_2$, OR$_3$, SR$_4$ or NR$_5$R$_6$; or R$_1$ is C$_2$-C$_{20}$alkyl interrupted by one or more O, S, NR$_5$, CO, SO or SO$_2$, which interrupted C$_2$-C$_{20}$alkyl is unsubstituted or substituted by one or more C$_3$-C$_8$cycloalkyl, OH, SH, O(CO)R$_{1a}$, (CO)OR$_3$, (CO)NR$_5$R$_6$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, C$_1$-C$_8$alkyl, OR$_3$, SR$_4$ or NR$_5$R$_6$;

R$_1$ is C$_2$-C$_{12}$alkenyl or C$_3$-C$_{20}$cycloalkyl, each of which is uninterrupted, or interrupted by one or more O, S, CO, NR$_5$ or COOR$_3$;

R$_1$ is C$_6$-C$_{20}$aryl or C$_3$-C$_{20}$heteroaryl, each of which is unsubstituted, or substituted by one or more halogen, C$_1$-C$_{20}$alkyl, C$_1$-C$_4$haloalkyl, phenyl, C$_1$-C$_{20}$alkylphenyl, C$_1$-C$_8$alkoxyphenyl, CN, NO$_2$, OR$_3$, SR$_4$, NR$_5$R$_6$, COOR$_3$, (CO)R$_{1a}$ or SO$_2$-R$_{1a}$;

R$_1$ is C$_1$-C$_{20}$alkoxy, which is unsubstituted, or substituted by one or more C$_1$-C$_{10}$alkyl, C$_1$-C$_4$haloalkyl, halogen, phenyl, C$_1$-C$_{20}$alkylphenyl or C$_1$-C$_8$alkoxyphenyl;

R$_1$ is C$_2$-C$_{20}$alkoxy, which is interrupted by one or more O, S, NR$_5$, CO, SO or SO$_2$;

R$_1$ is C$_6$-C$_{20}$aryloxy or C$_3$-C$_{20}$heteroaryloxy, which is unsubstituted, or substituted by one or more halogen, C$_1$-C$_{20}$alkyl, C$_1$-C$_4$haloalkyl, phenyl, C$_1$-C$_{20}$alkylphenyl, C$_1$-C$_8$alkoxyphenyl, CN, NO$_2$, OR$_3$, SR$_4$, NR$_5$R$_6$, COOR$_3$, (CO)R$_{1a}$ or SO$_2$R$_{1a}$; or R$_1$ is R$_{1a}$, and R$_{1a}$ is selected from hydrogen, or C$_1$-C$_{20}$alkyl which is unsubstituted, or substituted by one or more substituents selected from the group consisting of halogen, OR$_{3a}$, SR$_{4a}$, NR$_{5a}$R$_{6a}$, CN, (CO)OR$_{3a}$, (CO)NR$_{5a}$R$_{6a}$, C$_3$-C$_8$cycloalkyl which is uninterrupted, or interrupted by one or more O, S, CO or NR$_{5a}$, C$_6$-C$_{20}$aryl, C$_3$-C$_{20}$heteroaryl, C$_6$-C$_{20}$aroyl and C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted, or substituted by one or more halogen, phenyl, C$_1$-C$_{20}$alkylphenyl, C$_1$-C$_8$alkoxyphenyl, C$_1$-C$_4$haloalkyl, CN, NO$_2$, OR$_{3a}$, SR$_{4a}$ or NR$_{5a}$R$_{6a}$;

R$_{1a}$ is C$_2$-C$_{20}$alkyl interrupted by one or more O, S, NR$_{5a}$, CO, SO or SO$_2$, which interrupted C$_2$-C$_{20}$alkyl is unsubstituted, or substituted by one or more C$_3$-C$_8$cycloalkyl, OH, SH, O(CO)—(C$_1$-C$_8$alkyl), (CO)OR$_{3a}$, (CO)NR$_{5a}$R$_{6a}$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted, or substituted by one or more halogen, C$_1$-C$_8$alkyl, OR$_{3a}$, SR$_{4a}$ or NR$_{5a}$R$_{6a}$;

R$_{1a}$ is C$_2$-C$_{12}$alkenyl or C$_3$-C$_{20}$cycloalkyl, each of which is uninterrupted or interrupted by one or more O, S, CO, NR$_{5a}$ or COOR$_{3a}$;

R$_{1a}$ is C$_6$-C$_{20}$aryl or C$_3$-C$_{20}$heteroaryl, which C$_6$-C$_{20}$aryl or C$_3$-C$_{20}$heteroaryl is unsubstituted or substituted by one or more halogen, C$_1$-C$_{20}$alkyl, C$_1$-C$_4$haloalkyl, phenyl, C$_1$-C$_{20}$alkylphenyl, C$_1$-C$_8$alkoxyphenyl, CN, NO$_2$, OR$_{3a}$, SR$_{4a}$, NR$_{5a}$R$_{6a}$, COOR$_{3a}$, (CO)—(C$_1$-C$_8$alkyl), benzoyl or SO$_2$—(C$_1$-C$_4$haloalkyl);

R$_{1a}$ is C$_1$-C$_{20}$alkoxy, which is unsubstituted or substituted by one or more C$_1$-C$_{10}$alkyl, C$_1$-C$_4$haloalkyl, halogen, phenyl, C$_1$-C$_{20}$alkylphenyl or C$_1$-C$_8$alkoxyphenyl;

R$_{1a}$, is C$_2$-C$_{20}$alkoxy, which is interrupted by one or more O, S, NR$_{5a}$, CO, SO or SO$_2$; or R$_{1a}$ is C$_6$-C$_{20}$aryloxy or C$_3$-C$_{20}$heteroaryloxy, which C$_6$-C$_{20}$aryloxy or C$_3$-C$_{20}$heteroaryloxy is unsubstituted, or substituted by one or more halogen, C$_1$-C$_{20}$alkyl, C$_1$-C$_4$haloalkyl, phenyl, C$_1$-C$_{20}$alkylphenyl, C$_1$-C$_8$alkoxyphenyl, CN, NO$_2$, OR$_{3a}$, SR$_{4a}$, NR$_{5a}$R$_{6a}$, COOR$_{3a}$, (CO)(C$_1$-C$_8$alkyl), SO$_2$—(C$_1$-C$_4$haloalkyl), benzoyl, or

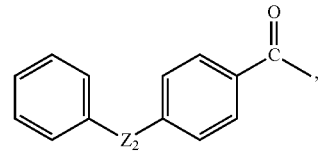

which benzoyl or

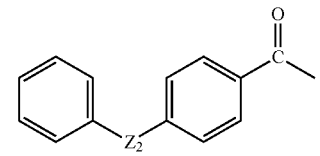

is unsubstituted, or substituted by

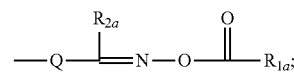

$R_2$ is $C_1$-$C_{20}$alkyl which is substituted by $C_3$-$C_8$cycloalkyl $R_3$ is selected from hydrogen, (CO)$R_{1a}$, (CO)O$R_{3a}$, CON$R_5R_6$, $C_1$-$C_{20}$alkyl, which is unsubstituted or substituted by one or more substituents selected from the group consisting of halogen, O$R_{3a}$, S$R_{4a}$, N$R_{5a}R_{6a}$, CN, (CO)O$R_{3a}$, (CO)N$R_{5a}R_{6a}$, PO(O$R_{1a}$)$_2$, S(O)$_m R_{1a}$, $C_3$-$C_8$cycloalkyl which is uninterrupted or interrupted by one or more O, S, CO or N$R_{5a}$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, phenyl, $C_1$-$C_{20}$alkylphenyl, $C_1$-$C_8$alkoxyphenyl, $C_1$-$C_4$haloalkyl, CN, NO$_2$, O$R_{3a}$, S$R_{4a}$, N$R_{5a}R_{6a}$, PO(O$R_{1a}$)$_2$ or S(O)$_m R_{1a}$;

$R_3$ is $C_2$-$C_{20}$alkyl interrupted by one or more O, S, N$R_{5a}$, CO, SO or SO$_2$, which interrupted $C_2$-$C_{20}$alkyl is unsubstituted, or substituted by one or more $C_3$-$C_8$cycloalkyl, OH, SH, O(CO)$R_{1a}$, (CO)O$R_{3a}$, (CO)N$R_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, O$R_{3a}$, S$R_{4a}$ or N$R_{5a}R_{6a}$;

$R_3$ is $C_2$-$C_{12}$alkenyl or $C_3$-$C_{20}$cycloalkyl, which $C_2$-$C_{12}$alkenyl or $C_3$-$C_{20}$cycloalkyl is uninterrupted, or interrupted by one or more O, S, CO, N$R_{5a}$ or COO$R_{3a}$;

$R_3$ is $C_6$-$C_{20}$aryl or $C_3$-$C_{20}$heteroaryl, which $C_6$-$C_{20}$aryl or $C_3$-$C_{20}$heteroaryl is unsubstituted or substituted by one or more substituents selected from the group consisting of halogen, CN, NO$_2$, O$R_{3a}$, S$R_{4a}$, N$R_{5a}R_{6a}$, COO$R_{3a}$, (CO)$R_{1a}$(CO)N$R_{5a}R_{6a}$, PO(O$R_{1a}$)$_2$, S(O)$_m R_{1a}$,

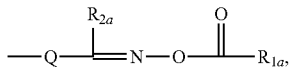

$C_1$-$C_{20}$alkyl which is unsubstituted, or substituted by one or more halogen, COO$R_{3a}$, CON$R_{5a}R_{6a}$, phenyl, $C_3$-$C_8$cycloalkyl, $C_3$-$C_{20}$heteroaryl, O$R_{3a}$, S$R_{4a}$ or N$R_{5a}R_{6a}$, $C_2$-$C_{20}$alkyl which is interrupted by one or more O, S or N$R_{5a}$; phenyl, naphthyl, benzoyl and naphthoyl, which phenyl, naphthyl, benzoyl or naphthoyl is unsubstituted, or substituted by one or more O$R_{3a}$, S$R_{4a}$ or N$R_{5a}R_{6a}$;

$R_3$ together with one of the carbon atoms of $R_2$ or M forms a 5- or 6-membered saturated or unsaturated ring which is uninterrupted, or interrupted by O, S or N$R_{5a}$, and which 5- or 6-membered saturated or unsaturated ring is unsubstituted, or substituted by one or more $C_1$-$C_{20}$alkyl, O$R_{3a}$, S$R_{4a}$, N$R_{5a}R_{6a}$, (CO)$R_{1a}$, NO$_2$, halogen, $C_1$-$C_4$-haloalkyl, CN, phenyl, $C_1$-$C_{20}$alkylphenyl, $C_1$-$C_8$alkoxyphenyl,

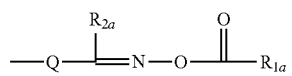

or $C_3$-$C_{20}$cyclalkyl which is uninterrupted or interrupted by one or more O, S, CO or N$R_{5a}$; or $R_3$ is $R_{3a}$, and $R_{3a}$ is selected from hydrogen, (CO)O($C_1$-$C_8$alkyl) or CON($C_1$-$C_8$alkyl)$_2$;

$R_{3a}$ is $C_1$-$C_{20}$alkyl which is unsubstituted, or substituted by one or more substituents selected from the group consisting of halogen, OH, SH, CN, $C_3$-$C_8$alkenoxy, OCH$_2$CH$_2$CN, OCH$_2$CH$_2$(CO)O ($C_1$-$C_8$alkyl), O(CO)($C_1$-$C_8$alkyl), O(CO)($C_2$-$C_4$) alkenyl, O(CO)phenyl, (CO)OH, (CO)O($C_1$-$C_8$alkyl), $C_3$-$C_8$cycloalkyl, SO$_2$($C_1$-$C_4$haloalkyl), O($C_1$-$C_4$haloalkyl), phenyl, $C_1$-$C_8$alkylphenyl, $C_1$-$C_8$alkoxyphenyl and $C_3$-$C_8$cycloalkyl which is interrupted by one or more O;

$R_{3a}$ is $C_2$-$C_{20}$alkyl interrupted by one or more O, S, N($C_1$-$C_8$alkyl), CO, SO or SO$_2$, which interrupted $C_2$-$C_{20}$alkyl is unsubstituted, or substituted by one or more $C_3$-$C_8$cycloalkyl, OH, SH, O(CO)($C_1$-$C_8$alkyl), (CO)O($C_1$-$C_8$alkyl), (CO)N($C_1$-$C_8$alkyl)$_2$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, $C_1$-$C_8$alkyl, $C_1$-$C_8$alkoxy, $C_1$-$C_8$alkylsulfanyl or N($C_1$-$C_8$alkyl)$_2$;

$R_{3a}$ is $C_2$-$C_{12}$alkenyl or $C_3$-$C_8$cycloalkyl, which $C_2$-$C_{12}$alkenyl or $C_3$-$C_8$cycloalkyl is uninterrupted, or interrupted by one or more O, S, CO, N($C_1$-$C_8$alkyl) or COO($C_1$-$C_8$alkyl); or $R_{3a}$ is $C_6$-$C_{20}$aryl, $C_3$-$C_{20}$heteroaryl, $C_6$-$C_{20}$aroyl or $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, CN, NO$_2$, OH, $C_1$-$C_8$alkyl, $C_1$-$C_4$haloalkyl, $C_1$-$C_8$alkoxy, phenyl-$C_1$-$C_3$alkyloxy, phenoxy, $C_1$-$C_8$alkylsulfanyl, phenylsulfanyl, N($C_1$-$C_8$alkyl)$_2$, diphenylamino, (CO)O ($C_1$-$C_8$alkyl), (CO)$C_1$-$C_8$alkyl or (CO)N($C_1$-$C_8$)$_2$, phenyl or benzoyl; or $R_{3a}$ is $C_1$-$C_{20}$alkanoyl or $C_3$-$C_{12}$alkenoyl, which $C_1$-$C_{20}$alkanoyl or $C_3$-$C_{12}$alkenoyl is unsubstituted or substituted by one or more halogen, phenyl, $C_1$-$C_8$alkylphenyl, $C_1$-$C_8$alkoxyphenyl, OH, $C_1$-$C_8$alkoxy, phenoxy, $C_1$-$C_8$alkylsulfanyl, phenylsulfanyl, N($C_1$-$C_8$alkyl)$_2$ or diphenylamino;

$R_4$ is selected from hydrogen, $C_1$-$C_{20}$alkyl which is unsubstituted, or substituted by one or more substituents selected from the group consisting of halogen, O$R_{3a}$, S$R_{4a}$, N$R_{5a}R_{6a}$, CN, (CO)O$R_{3a}$, (CO)N$R_{5a}R_{6a}$, PO(O$R_{1a}$)$_2$, S(O)$_m R_{1a}$, $C_3$-$C_8$cycloalkyl which is uninterrupted, or interrupted by one or more O, S, CO or N$R_{5a}$, $C_6$-$C_{20}$aryl, $C_3$-$C_{20}$heteroaryl, $C_6$-$C_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, phenyl, $C_1$-$C_{20}$alkylphenyl, $C_1$-$C_8$alkoxyphenyl, $C_1$-$C_4$haloalkyl, CN, NO$_2$, O$R_{3a}$, S$R_{4a}$, N$R_{5a}R_{6a}$, PO(O$R_{1a}$)$_2$ or S(O)$_m R_{1a}$;

$R_4$ is $C_2$-$C_{20}$alkyl interrupted by one or more O, S, N$R_{5a}$, CO, SO or SO$_2$, which interrupted $C_2$-$C_{20}$alkyl is unsubstituted, or substituted by one or more $C_3$-$C_8$cycloalkyl, OH, SH, O(CO)$R_{1a}$, (CO)O$R_{3a}$, (CO)N$R_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, $C_1$-$C_8$alkyl, O$R_{3a}$, S$R_{4a}$ or N$R_{5a}R_{6a}$;

$R_4$ is $C_2$-$C_{12}$alkenyl or $C_3$-$C_{20}$cycloalkyl, which $C_2$-$C_{12}$alkenyl or $C_3$-$C_{20}$cycloalkyl is uninterrupted, or interrupted by one or more O, S, CO, $NR_{5a}$ or $COOR_{3a}$;

$R_4$ is $C_6$-$C_{20}$aryl or $C_3$-$C_{20}$heteroaryl, which $C_6$-$C_{20}$aryl or $C_3$-$C_{20}$heteroaryl is unsubstituted, or substituted by one or more substituents selected from the group consisting of halogen, CN, $NO_2$, $OR_{3a}$, $SR_{4a}$, $NR_{5a}R_{6a}$, $COOR_{3a}$, $(CO)R_{1a}$ $(CO)NR_{5a}R_{6a}$, $PO(OR_{1a})_2$, $S(O)_mR_{1a}$,

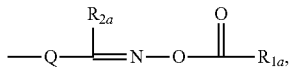

$C_1$-$C_{20}$alkyl which is unsubstituted, or substituted by one or more halogen, $COOR_{3a}$, $CONR_{5a}R_{6a}$, phenyl, $C_3$-$C_8$cycloalkyl, $C_3$-$C_{20}$heteroaryl, $OR_{3a}$, $SR_{4a}$ or $NR_{5a}R_{6a}$, $C_2$-$C_{20}$alkyl which is interrupted by one or more O, S or $NR_{5a}$, phenyl, naphthyl, benzoyl and naphthoyl, which phenyl, naphthyl, benzoyl or naphthoyl is unsubstituted, or substituted by $OR_{3a}$, $SR_{4a}$ or $NR_{5a}R_{6a}$;

$R_4$ together with one of the carbon atoms of $R_2$ or M forms a 5- or 6-membered saturated or unsaturated ring which is uninterrupted, or interrupted by O, S or $NR_{5a}$, and which 5- or 6-membered saturated or unsaturated ring is unsubstituted or substituted by one or more $C_1$-$C_{20}$alkyl, $OR_{3a}$, $SR_{4a}$, $NR_{5a}R_{6a}$, $(CO)R_{1a}$, $NO_2$, halogen, $C_1$-$C_4$-haloalkyl, CN, phenyl, $C_1$-$C_{20}$alkylphenyl, $C_1$-$C_8$alkoxyphenyl,

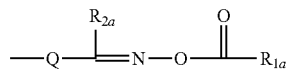

or $C_3$-$C_{20}$cyclalkyl which is uninterrupted, or interrupted by one or more O, S, CO or $NR_{5a}$; or $R_4$ is $R_{4a}$, and $R_{4a}$ is selected from hydrogen, $C_1$-$C_{20}$alkyl which is unsubstituted, or substituted by one or more substituents selected from the group consisting of halogen, OH, SH, CN, $C_3$-$C_8$alkenoxy, $OCH_2CH_2CN$, $OCH_2CH_2(CO)O(C_1$-$C_8$alkyl), $O(CO)(C_1$-$C_8$alkyl), $O(CO)(C_2$-$C_4$)alkenyl, $O(CO)$phenyl, $(CO)OH$, $(CO)O(C_1$-$C_8$alkyl), $C_3$-$C_8$cycloalkyl, $SO_2(C_1$-$C_4$haloalkyl), $O(C_1$-$C_4$haloalkyl), phenyl, $C_1$-$C_8$alkylphenyl, $C_1$-$C_8$alkoxyphenyl and $C_3$-$C_8$cycloalkyl which is interrupted by one or more O;

$R_{4a}$ is $C_2$-$C_{20}$alkyl interrupted by one or more O, S, $N(C_1$-$C_8$alkyl), CO, SO or $SO_2$, which interrupted $C_2$-$C_{20}$alkyl is unsubstituted, or substituted by one or more $C_3$-$C_8$cycloalkyl, OH, SH, $O(CO)(C_1$-$C_8$alkyl), $(CO)O(C_1$-$C_8$alkyl), $(CO)N(C_1$-$C_8$alkyl)$_2$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, $C_1$-$C_8$alkyl, $C_1$-$C_8$alkoxy, $C_1$-$C_8$alkylsulfanyl or $N(C_1$-$C_8$alkyl)$_2$;

$R_{4a}$ is $C_2$-$C_{12}$alkenyl or $C_3$-$C_8$cycloalkyl, which $C_2$-$C_{12}$alkenyl or $C_3$-$C_8$cycloalkyl is uninterrupted, or interrupted by one or more O, S, CO, $N(C_1$-$C_8$alkyl) or $COO(C_1$-$C_8$alkyl);

$R_{4a}$ is $C_6$-$C_{20}$aryl, $C_3$-$C_{20}$heteroaryl, $C_6$-$C_{20}$aroyl or $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, CN, $NO_2$, OH, $C_1$-$C_8$alkyl, $C_1$-$C_4$haloalkyl, $C_1$-$C_8$alkoxy, phenyl-$C_1$-$C_3$alkyloxy, phenoxy, $C_1$-$C_8$alkylsulfanyl, phenylsulfanyl, $N(C_1$-$C_8$alkyl)$_2$, diphenylamino, $(CO)O(C_1$-$C_8$alkyl), $(CO)C_1$-$C_8$alkyl, $(CO)N(C_1$-$C_8)_2$, phenyl or benzoyl; or $R_{4a}$ is $C_1$-$C_{20}$alkanoyl or $C_3$-$C_{12}$alkenoyl, which $C_1$-$C_{20}$alkanoyl or $C_3$-$C_{12}$alkenoyl is unsubstituted, or substituted by one or more halogen, phenyl, $C_1$-$C_8$alkylphenyl, $C_1$-$C_8$alkoxyphenyl, OH, $C_1$-$C_8$alkoxy, phenoxy, $C_1$-$C_8$alkylsulfanyl, phenylsulfanyl, $N(C_1$-$C_8$alkyl)$_2$ or diphenylamino;

$R_5$ and $R_6$ independently of each other are hydrogen, $S(O)_mR_{1a}$, $O(CO)R_{1a}$, $(CO)R_{1a}$ or $CONR_{5a}R_{6a}$;

$R_5$ and $R_6$ independently of each other are $C_1$-$C_{20}$alkyl which is unsubstituted, or substituted by one or more substituents selected from the group consisting of halogen, $OR_{3a}$, $SR_{4a}$, $NR_{5a}R_{6a}$, CN, $(CO)OR_{3a}$, $(CO)NR_{5a}R_{6a}$, $PO(OR_{1a})_2$, $S(O)_mR_{1a}$, $C_3$-$C_8$cycloalkyl, which is uninterrupted, or interrupted by one or more O, S, CO or $NR_{5a}$, $C_6$-$C_{20}$aryl, $C_3$-$C_{20}$heteroaryl, $C_6$-$C_{20}$aroyl and $C_3$-$C_{20}$heteroarylcarbonyl, of which $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_{3a}$, $SR_{4a}$, $NR_{5a}R_{6a}$, $PO(OR_{1a})_2$ or $S(O)_mR_{1a}$;

$R_5$ and $R_6$ independently of each other are $C_2$-$C_{20}$alkyl interrupted by one or more O, S, $NR_{5a}$, CO, SO or $SO_2$, which interrupted $C_2$-$C_{20}$alkyl is unsubstituted, or substituted by one or more $C_3$-$C_8$cycloalkyl, OH, SH, $O(CO)R_{1a}$, $(CO)OR_{3a}$, $(CO)NR_{5a}R_{6a}$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted, or substituted by one or more halogen, $C_1$-$C_8$alkyl, $OR_{3a}$, $SR_{4a}$ or $NR_{5a}R_{6a}$;

$R_5$ and $R_6$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted, or interrupted by one or more O, S, CO, $NR_{5a}$ or $COOR_{3a}$;

$R_5$ and $R_6$ independently of each other are $C_6$-$C_{20}$aryl or $C_3$-$C_{20}$heteroaryl, which $C_6$-$C_{20}$aryl or $C_3$-$C_{20}$heteroaryl is unsubstituted, or substituted by one or more substituents selected from the group consisting of halogen, CN, $NO_2$, $OR_{3a}$, $SR_{4a}$, $NR_{5a}R_{6a}$, $COOR_{3a}$, $(CO)R_{1a}$ $(CO)NR_{5a}R_{6a}$, $PO(OR_{1a})_2$, $S(O)_mR_{1a}$,

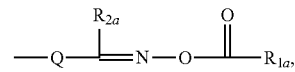

$C_1$-$C_{20}$alkyl, which is unsubstituted or substituted by one or more halogen, $COOR_{3a}$, $CONR_{5a}R_{6a}$, phenyl, $C_3$-$C_8$cycloalkyl, $C_3$-$C_{20}$heteroaryl, $OR_{3a}$, $SR_{4a}$ or $NR_{5a}R_{6a}$, $C_2$-$C_{20}$alkyl which is interrupted by one or more O, S or $NR_{5a}$, phenyl, naphthyl, benzoyl and naphthoyl, which phenyl, naphthyl, benzoyl or naphthoyl is unsubstituted, or substituted by $OR_{3a}$, $SR_{4a}$ or $NR_{5a}R_{6a}$;

$R_5$ and $R_6$ independently of each other are $C_1$-$C_{20}$alkoxy, which is unsubstituted, or substituted by one or more halogen, phenyl, $C_1$-$C_8$alkylphenyl or $C_1$-$C_8$alkoxyphenyl;

$R_5$ and $R_6$ independently of each other are $C_2$-$C_{20}$alkoxy, which is interrupted by one or more O, S, $NR_{5a}$, CO, SO or $SO_2$;

$R_5$ and $R_6$ independently of each other are $C_6$-$C_{20}$aryloxy or $C_3$-$C_{20}$heteroaryloxy, which $C_6$-$C_{20}$aryloxy or $C_3$-$C_{20}$heteroaryloxy is unsubstituted, or substituted by one or more halogen, $C_1$-$C_8$alkyl, $C_1$-$C_4$haloalkyl, phenyl, $C_1$-$C_8$alkylphenyl, $C_1$-$C_8$alkoxyphenyl, CN, $NO_2$, $OR_{3a}$, $SR_{4a}$, $NR_{5a}R_{6a}$, $COOR_{3a}$, $(CO)R_{1a}$ or $SO_2R_{1a}$;

$R_5$ together with one of the carbon atoms of $R_2$ or M forms a 5- or 6-membered saturated or unsaturated ring which is uninterrupted, or interrupted by O, S or $NR_{5a}$, and which 5- or 6-membered saturated or unsaturated ring is unsubstituted, or substituted by one or more $C_1$-$C_{20}$alkyl, $OR_{3a}$, $SR_{4a}$, $NR_{5a}R_{6a}$, $(CO)R_{1a}$, $NO_2$, halogen, $C_1$-$C_4$-haloalkyl, CN, phenyl, $C_1$-$C_{20}$alkylphenyl, $C_1$-$C_8$alkoxyphenyl,

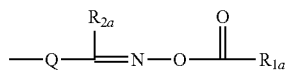

or $C_3$-$C_{20}$cyclalkyl, which is uninterrupted or interrupted by one or more O, S, CO or $NR_{5a}$;

$R_5$ and $R_6$ together with the N-atom to which they are attached form a 5- or 6-membered saturated or unsaturated ring which is uninterrupted, or interrupted by O, S or $NR_{5a}$, and which 5- or 6-membered saturated or unsaturated ring is unsubstituted, or substituted by one or more $C_1$-$C_{20}$alkyl, $OR_{3a}$, $SR_{4a}$, $NR_{5a}R_{6a}$, $(CO)R_{1a}$, $NO_2$, halogen, $C_1$-$C_4$-haloalkyl, CN, phenyl,

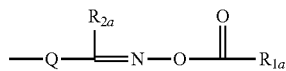

or $C_3$-$C_{20}$cyclalkyl which is uninterrupted, or interrupted by one or more O, S, CO or $NR_{5a}$; or $R_5$ and $R_6$ is $R_{5a}$ and $R_{6a}$, and $R_{5a}$ and $R_{6a}$ are independently of each other are hydrogen, $C_1$-$C_{20}$alkyl, $S(O)_m(C_1$-$C_8$alkyl), $O(CO)(C_1$-$C_8$alkyl), $(CO)(C_1$-$C_8$alkyl), $(CO)O(C_1$-$C_8$alkyl) or $CON(C_1$-$C_8$alkyl)$_2$;

$R_{5a}$ and $R_{6a}$ independently of each other are $C_1$-$C_{20}$alkyl substituted by one or more halogen, OH, SH, CN, $C_3$-$C_8$alkenoxy, $OCH_2CH_2CN$, $OCH_2CH_2(CO)O(C_1$-$C_8$alkyl), $O(CO)(C_1$-$C_8$alkyl), $O(CO)(C_2$-$C_4)$alkenyl, $O(CO)$phenyl, $(CO)OH$, $(CO)O(C_1$-$C_8$alkyl), $C_3$-$C_8$cycloalkyl, $SO_2(C_1$-$C_4$haloalkyl), $O(C_1$-$C_4$haloalkyl), phenyl, $C_1$-$C_8$alkylphenyl, $C_1$-$C_8$alkoxyphenyl, $C_3$-$C_8$cycloalkyl or $C_3$-$C_8$cycloalkyl which is interrupted by one or more O;

or $R_{5a}$ and $R_{6a}$ independently of each other are $C_2$-$C_{20}$alkyl interrupted by one or more O, S, $N(C_1$-$C_8$alkyl), CO, SO or $SO_2$, which interrupted $C_2$-$C_{20}$alkyl is unsubstituted or substituted by $C_3$-$C_8$cycloalkyl, OH, SH, $O(CO)(C_1$-$C_8$alkyl), $(CO)O(C_1$-$C_8$alkyl)$, $(CO)N(C_1$-$C_8$alkyl)$_2$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $C_1$-$C_8$alkoxy, $C_1$-$C_8$alkylsulfanyl or $N(C_1$-$C_8$alkyl)$_2$;

$R_{5a}$ and $R_{6a}$ independently of each other are $C_2$-$C_{12}$alkenyl or $C_3$-$C_8$cycloalkyl, which $C_2$-$C_{12}$alkenyl or $C_3$-$C_8$cycloalkyl is uninterrupted or interrupted by one or more O, S, CO, $N(C_1$-$C_8$alkyl) or $COO(C_1$-$C_8$alkyl);

$R_{5a}$ and $R_{6a}$ independently of each other are $C_6$-$C_{20}$aryl, $C_3$-$C_{20}$heteroaryl, $C_6$-$C_{20}$aroyl or $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, CN, $NO_2$, OH, $C_1$-$C_8$alkyl, $C_1$-$C_4$haloalkyl, $C_1$-$C_8$alkoxy, phenyl-$C_1$-$C_3$alkyloxy, phenoxy, $C_1$-$C_8$alkylsulfanyl, phenylsulfanyl, $N(C_1$-$C_8$alkyl)$_2$, diphenylamino, $(CO)O(C_1$-$C_8$alkyl), $(CO)C_1$-$C_8$alkyl, $(CO)N(C_1$-$C_8$alkyl)$_2$, phenyl or benzoyl;

$R_{5a}$ and $R_{6a}$ independently of each other are $C_1$-$C_{20}$alkanoyl or $C_3$-$C_{12}$alkenoyl, which $C_1$-$C_{20}$alkanoyl or $C_3$-$C_{12}$alkenoyl is unsubstituted or substituted by one or more halogen, phenyl, $C_1$-$C_8$alkylphenyl, $C_1$-$C_8$alkoxyphenyl, OH, $C_1$-$C_8$alkoxy, phenoxy, $C_1$-$C_8$alkylsulfanyl, phenylsulfanyl, $N(C_1$-$C_8$alkyl)$_2$ or diphenylamino;

$R_{5a}$ and $R_{6a}$ independently of each other are $C_1$-$C_{20}$alkoxy, which is unsubstituted or substituted by one or more halogen, phenyl, $C_1$-$C_8$alkylphenyl or $C_1$-$C_8$alkoxyphenyl;

or $R_{5a}$ and $R_{6a}$ independently of each other are $C_2$-$C_{20}$alkoxy, which is interrupted by one or more O, S, $N(C_1$-$C_8$alkyl), CO, SO or $SO_2$;

$R_{5a}$ and $R_{6a}$ independently of each other are $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by one or more halogen, $C_1$-$C_8$alkyl, $C_1$-$C_4$haloalkyl, phenyl, $C_1$-$C_8$alkylphenyl, $C_1$-$C_8$alkoxyphenyl, CN, $NO_2$, $C_1$-$C_8$alkoxy, $C_1$-$C_8$alkylsulfanyl, $N(C_1$-$C_8$alkyl)$_2$, $CO(OC_1$-$C_8$alkyl), $(CO)(C_1$-$C_8$alkyl)$ or $SO_2$—$(C_1$-$C_8$alkyl); or $R_{5a}$ and $R_{6a}$ together with the N-atom to which they are attached form a 5- or 6-membered saturated or unsaturated ring which is uninterrupted or interrupted by O, S or $N(C_1$-$C_8$alkyl), and which 5- or 6-membered saturated or unsaturated ring is unsubstituted or substituted by one or more $C_1$-$C_8$alkyl, $C_1$-$C_8$alkoxy, $C_1$-$C_8$alkylsulfanyl, $N(C_1$-$C_8$alkyl)$_2$, $NO_2$, halogen, $C_1$-$C_4$haloalkyl, CN, phenyl or $C_3$-$C_{20}$cyclalkyl which is uninterrupted or interrupted by one or more O, S, CO or $N(C_1$-$C_8$alkyl);

$R_7$, $R_8$, $R_9$, $R_{10}$ and $R_{11}$ independently of each other are hydrogen, $C_1$-$C_{20}$alkyl, halogen, CN, $NO_2$, $OR_3$, $SR_4$, $NR_5R_6$, $COOR_3$, $(CO)R_{1a}$, $(CO)NR_5R_6$, $PO(OR_{1a})_2$, $S(O)_mR_{1a}$,

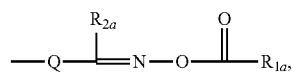

wherein the substituents OR$_3$, SR$_4$ or NR$_5$R$_6$ optionally form 5- or 6-membered ring via the radicals R$_3$, R$_4$, R$_5$ or R$_6$ with further substituents on the group X;

or R$_7$, R$_8$, R$_9$, R$_{10}$ and R$_{11}$ independently of each other are C$_1$-C$_{20}$alkyl substituted by one or more substituents selected from the group consisting of halogen, OR$_3$, SR$_4$, NR$_5$R$_6$, CN, (CO)OR$_3$, (CO)NR$_5$R$_6$, PO(OR$_{1a}$)$_2$, S(O)$_m$R$_{1a}$, C$_3$-C$_8$cycloalkyl which is uninterrupted or interrupted by one or more O, S, CO or NR$_5$, C$_6$-C$_{20}$aryl, C$_3$-C$_{20}$heteroaryl, C$_6$-C$_{20}$aroyl and C$_3$-C$_{20}$heteroarylcarbonyl, which C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, phenyl, C$_1$-C$_{20}$alkylphenyl, C$_1$-C$_8$alkoxyphenyl, C$_1$-C$_4$haloalkyl, CN, NO$_2$, OR$_3$, SR$_4$, NR$_5$R$_6$, PO(OR$_{1a}$)$_2$ or S(O)$_m$R$_{1a}$;

R$_7$, R$_8$, R$_9$, R$_{10}$ and R$_{11}$ independently of each other are C$_2$-C$_{20}$alkyl interrupted by one or more O, S, NR$_5$, CO, SO or SO$_2$, which interrupted C$_2$-C$_{20}$alkyl is unsubstituted or substituted by C$_3$-C$_8$cycloalkyl, OH, SH, O(CO)R$_{1a}$, (CO)OR$_3$, (CO)NR$_5$R$_6$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, C$_1$-C$_8$alkyl, OR$_3$, SR$_4$ or NR$_5$R$_6$;

R$_7$, R$_8$, R$_9$, R$_{10}$ and R$_{11}$ independently of each other are C$_2$-C$_{12}$alkenyl or C$_3$-C$_{20}$cycloalkyl, which C$_2$-C$_{12}$alkenyl or C$_3$-C$_{20}$cycloalkyl is uninterrupted or interrupted by one or more O, S, CO, NR$_5$ or COOR$_3$; or R$_7$, R$_8$, R$_9$, R$_{10}$ and R$_{11}$ independently of each other are C$_6$-C$_{20}$aryl or C$_3$-C$_{20}$heteroaryl, which C$_6$-C$_{20}$aryl or C$_3$-C$_{20}$heteroaryl is unsubstituted or substituted by one or more substituents selected from the group consisting of halogen, CN, NO$_2$, OR$_3$, SR$_4$, NR$_5$R$_6$, COOR$_3$, (CO)R$_{1a}$(CO)NR$_5$R$_6$, PO(OR$_{1a}$)$_2$, S(O)$_m$R$_{1a}$,

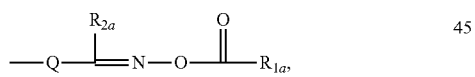

C$_1$-C$_{20}$alkyl, which is unsubstituted or substituted by one or more halogen, COOR$_3$, CONR$_5$R$_6$, phenyl, C$_3$-C$_8$cycloalkyl, C$_3$-C$_{20}$heteroaryl, OR$_3$, SR$_4$ or NR$_5$R$_6$, C$_2$-C$_{20}$alkyl which is interrupted by one or more O, S or NR$_5$, phenyl, naphthyl, benzoyl and naphthoyl, which phenyl, naphthyl, benzoyl or naphthoyl is unsubstituted, or substituted by OR$_3$, SR$_4$ or NR$_5$R$_6$;

or R$_8$ and R$_9$, R$_9$ and R$_{10}$, or R$_{10}$ and R$_{11}$ are

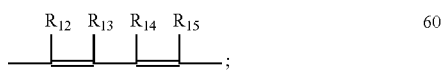

R$_{12}$, R$_{13}$, R$_{14}$ and R$_{15}$ independently of each other are hydrogen, C$_1$-C$_{20}$alkyl, halogen, CN, NO$_2$, OR$_3$, SR$_4$, NR$_5$R$_6$, COOR$_3$, (CO)R$_{1a}$, (CO)NR$_5$R$_6$, PO(OR$_{1a}$)$_2$, S(O)$_m$R$_{1a}$,

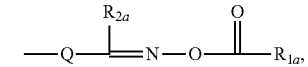

wherein the substituents OR$_3$, SR$_4$ or NR$_5$R$_6$ optionally form a 5- or 6-membered ring via the radicals R$_3$, R$_4$, R$_5$ or R$_6$ with further substituents on the group X;

or R$_{12}$, R$_{13}$, R$_{14}$ and R$_{15}$ independently of each other are C$_1$-C$_{20}$alkyl substituted by one or more substituents selected from the group consisting of halogen, OR$_3$, SR$_4$, NR$_5$R$_6$, CN, (CO)OR$_3$, (CO)NR$_5$R$_6$, PO(OR$_{1a}$)$_2$, S(O)$_m$R$_{1a}$, C$_3$-C$_8$cycloalkyl which is uninterrupted or interrupted by one or more O, S, CO or NR$_5$, C$_6$-C$_{20}$aryl, C$_3$-C$_{20}$heteroaryl, C$_6$-C$_{20}$aroyl and C$_3$-C$_{20}$heteroarylcarbonyl, which C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, phenyl, C$_1$-C$_{20}$alkylphenyl, C$_1$-C$_8$alkoxyphenyl, C$_1$-C$_4$haloalkyl, CN, NO$_2$, OR$_3$, SR$_4$, NR$_5$R$_6$, PO(OR$_{1a}$)$_2$ or S(O)$_m$R$_{1a}$;

R$_{12}$, R$_{13}$, R$_{14}$ and R$_{15}$ independently of each other are C$_2$-C$_{20}$alkyl interrupted by one or more O, S, NR$_5$, CO, SO or SO$_2$, which interrupted C$_2$-C$_{20}$alkyl is unsubstituted or substituted by C$_3$-C$_8$cycloalkyl, OH, SH, O(CO)R$_{1a}$, (CO)OR$_3$, (CO)NR$_5$R$_6$, C$_6$-C$_{20}$aryl, C$_3$-C$_{20}$heteroaryl, C$_6$-C$_{20}$aroyl or C$_3$-C$_{20}$heteroarylcarbonyl, wherein C$_6$-C$_{20}$aryl, C$_3$-C$_{20}$heteroaryl, C$_6$-C$_{20}$aroyl or C$_3$-C$_{20}$heteroarylcarbonyl is unsubstituted or substituted by one or more halogen, C$_1$-C$_8$alkyl, OR$_3$, SR$_4$ or NR$_5$R$_6$;

R$_{12}$, R$_{13}$, R$_{14}$ and R$_{15}$ independently of each other are C$_2$-C$_{12}$alkenyl or C$_3$-C$_{20}$cycloalkyl, which C$_2$-C$_{12}$alkenyl or C$_3$-C$_{20}$cycloalkyl is uninterrupted or interrupted by one or more O, S, CO, NR$_5$ or COOR$_3$;

R$_{12}$, R$_{13}$, R$_{14}$ and R$_{15}$ independently of each other are C$_6$-C$_{20}$aryl or C$_3$-C$_{20}$heteroaryl, which C$_6$-C$_{20}$aryl or C$_3$-C$_{20}$heteroaryl is unsubstituted or substituted by one or more substituents selected from the group consisting of halogen, CN, NO$_2$, OR$_3$, SR$_4$, NR$_5$R$_6$, COOR$_3$, (CO)R$_{1a}$, (CO)NR$_5$R$_6$, PO(OR$_{1a}$)$_2$, S(O)$_m$—R$_{1a}$,

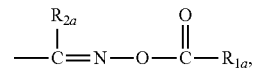

C$_1$-C$_{20}$alkyl, which is unsubstituted or substituted by one or more halogen, COOR$_{3a}$, CONR$_5$R$_6$, phenyl, C$_3$-C$_8$cycloalkyl, C$_3$-C$_{20}$heteroaryl, OR$_3$, SR$_4$ or NR$_5$R$_6$, C$_2$-C$_{20}$alkyl which is interrupted by one or more O, S or NR$_5$, phenyl, naphthyl, benzoyl and naphthoyl, which phenyl, naphthyl, benzoyl or naphthoyl is unsubstituted or substituted by OR$_3$, SR$_4$ or NR$_5$R$_6$;

R$_{16}$ and R$_{17}$ independently of each other are hydrogen, C$_1$-C$_{20}$alkyl, which is unsubstituted or substituted by one or more substituents selected from the group consisting of halogen, OR$_3$, SR$_4$, NR$_5$R$_6$, CN, (CO)OR$_3$, (CO)NR$_5$R$_6$, C$_3$-C$_8$cycloalkyl which is uninterrupted or interrupted by one or more O, S, CO or NR$_5$, C$_6$-C$_{20}$aryl, C$_3$-C$_{20}$heteroaryl, C$_6$-C$_{20}$aroyl and $C_3$-$C_{20}$heteroarylcarbonyl, which $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, phenyl, $C_1$-$C_{20}$alkylphenyl, $C_1$-$C_8$alkoxyphenyl, $C_1$-$C_4$haloalkyl, CN, $NO_2$, $OR_3$, $SR_4$ or $NR_5R_6$;

$R_{16}$ and $R_{17}$ independently of each other are $C_2$-$C_{20}$alkyl interrupted by one or more O, S, $NR_5$, CO, SO or $SO_2$, which interrupted $C_2$-$C_{20}$alkyl is unsubstituted or substituted by $C_3$-$C_8$cycloalkyl, OH, SH, $O(CO)R_{1a}$, $(CO)OR_3$, $(CO)NR_5R_6$, $C_6$-$C_{20}$aryl, $C_3$-$C_{20}$heteroaryl, $C_6$-$C_{20}$aroyl or $C_3$-$C_{20}$heteroarylcarbonyl, wherein $C_6$-$C_{20}$aryl, $C_3$-$C_{20}$heteroaryl, $C_6$-$C_{20}$aroyl or $C_3$-$C_{20}$heteroarylcarbonyl is unsubstituted or substituted by one or more halogen, $C_1$-$C_8$alkyl, $OR_3$, $SR_4$ or $NR_5R_6$;

$R_{16}$ and $R_{17}$ independently of each other are $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$;

$R_{16}$ and $R_{17}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $C_1$-$C_{20}$alkyl, $C_1$-$C_4$haloalkyl, phenyl, $C_1$-$C_{20}$alkylphenyl, $C_1$-$C_8$alkoxyphenyl, CN, $NO_2$, $OR_3$, $SR_4$, $NR_5R_6$, $COOR_3$, $(CO)R_{1a}$ or $SO_2R_{1a}$; or $R_{16}$ and $R_{17}$ together with the carbon atom to which they are attached form a 5- or 6-membered saturated or unsaturated ring which is uninterrupted or interrupted by O, S or $NR_{5a}$, and which 5- or 6-membered saturated or unsaturated ring is unsubstituted or substituted by one or more $C_1$-$C_{20}$alkyl, $OR_{3a}$, $SR_{4a}$, $NR_{5a}R_{6a}$, $(CO)R_{1a}$, $NO_2$, halogen, $C_1$-$C_4$haloalkyl, CN, phenyl or $C_3$-$C_{20}$cyclalkyl which is uninterrupted or interrupted by one or more O, S, CO or $NR_{5a}$;

$Ar_1$ is $C_6$-$C_{20}$aryl, $C_3$-$C_{20}$heteroaryl, $C_6$-$C_{20}$aroyl, $C_3$-$C_{20}$heteroarylcarbonyl or

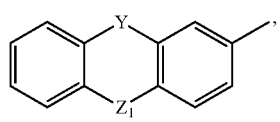

which $C_6$-$C_{20}$aryl, $C_3$-$C_{20}$heteroaryl, $C_6$-$C_{20}$aroyl, $C_3$-$C_{20}$heteroarylcarbonyl or

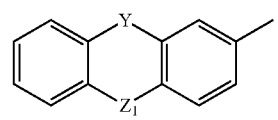

is unsubstituted or substituted by one or more substituents selected from the group consisting of halogen, CN, $NO_2$, $COOR_3$, $(CO)R_{1a}$, $(CO)NR_5R_6$, $PO(OR_{1a})_2$, $S(O)_mR_{1a}$,

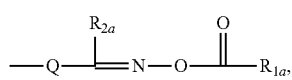

$OR_3$, $SR_4$, $NR_5R_6$, wherein the substituents $OR_3$, $SR_4$ or $NR_5R_6$ optionally form 5- or 6-membered rings via the radicals $R_3$, $R_4$, $R_5$ or $R_6$ with further substituents on the phenyl ring, $C_1$-$C_{20}$alkyl which is unsubstituted or substituted by one or more halogen, $COOR_3$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{20}$alkyl which is interrupted by one or more O, S or $NR_5$, $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$, phenyl, naphthyl, benzoyl and naphthoyl, which phenyl, naphthyl, benzoyl or naphthoyl is unsubstituted or substituted by $OR_3$, $SR_4$ or $NR_5R_6$;

or $Ar_1$ is

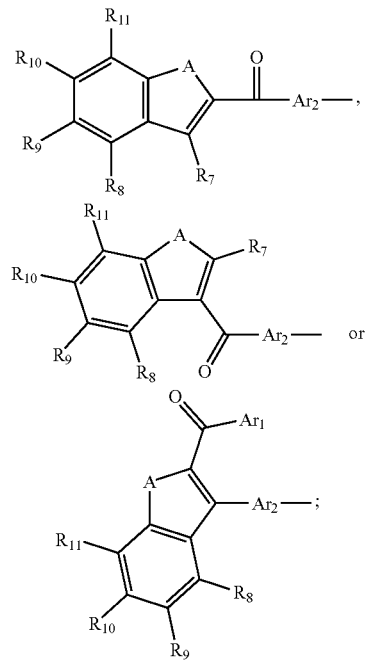

$Ar_2$ is phenylene, naphthylene, phenylenecarbonyl, naphthylenecarbonyl,

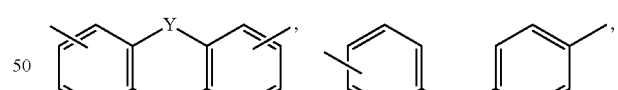

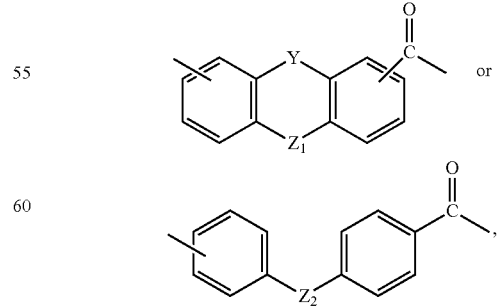

which phenylene, naphthylene, phenylenecarbonyl, naphthylenecarbonyl,

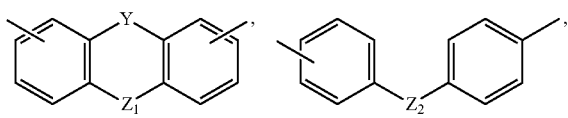, 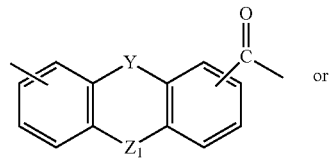 or

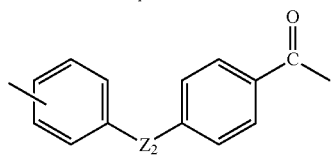

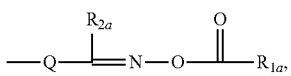

is unsubstituted or substituted by one or more substituents selected from the group consisting of halogen, CN, $NO_2$, $COOR_3$, $(CO)R_{1a}$, $(CO)NR_5R_6$, $PO(OR_{1a})_2$, $S(O)_mR_{1a}$, $$—Q—\overset{R_{2a}}{\underset{}{C}}=N—O—\overset{O}{\underset{}{C}}—R_{1a},$$

$OR_3$, $SR_4$, $NR_5R_6$, $C_1$-$C_{20}$alkyl which is unsubstituted or substituted by one or more halogen, $COOR_3$, $CONR_5R_6$, phenyl, $C_3$-$C_8$cycloalkyl, $C_3$-$C_{20}$heteroaryl, $OR_3$, $SR_4$ or $NR_5R_6$, $C_2$-$C_{12}$alkenyl or $C_3$-$C_{20}$cycloalkyl, which $C_2$-$C_{12}$alkenyl or $C_3$-$C_{20}$cycloalkyl is uninterrupted or interrupted by one or more O, S, CO, $NR_5$ or $COOR_3$, $C_2$-$C_{20}$alkyl which is interrupted by one or more O, S or $NR_5$, phenyl, naphthyl, benzoyl and naphthoyl, which phenyl, naphthyl, benzoyl or naphthoyl is unsubstituted or substituted by $OR_3$, $SR_4$ or $NR_5R_6$;

Y is a direct bond, O, S, $NR_5$ or CO;
$Z_1$ is O, S, CO or $CR_{16}(R_{17})$;
$Z_2$ is a direct bond, O, S or $NR_5$;
m is 1 or 2; and
Q is CO or a direct bond.

2. Compounds of the formulae (I) according to claim 1, wherein

X is

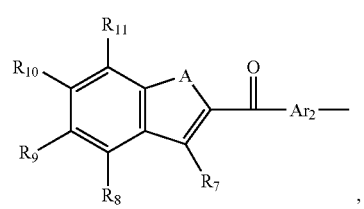,

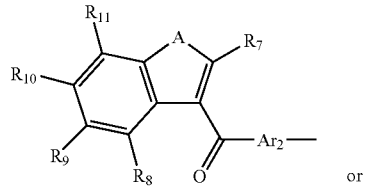 or

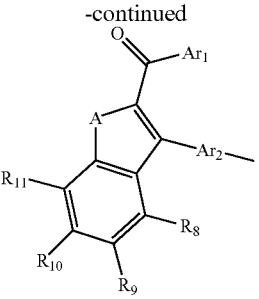;

A is O, S, $NR_5$ or $CR_{16}R_{17}$;
$R_1$ is $C_1$-$C_{20}$alkyl which is unsubstituted or substituted by one or more halogen, $OR_3$, $SR_4$, $NR_5R_6$, $(CO)OR_3$, $C_3$-$C_8$cycloalkyl or $C_3$-$C_8$cycloalkyl which is interrupted by one or more O;
or $R_1$ is $C_2$-$C_{20}$alkyl interrupted by one or more O, which interrupted $C_2$-$C_{20}$alkyl is unsubstituted or substituted by one or more OH, $O(CO)R_{1a}$ or $(CO)OR_3$;
or $R_1$ is $C_2$-$C_{12}$alkenyl or $C_3$-$C_{20}$cycloalkyl;
or $R_1$ is $C_6$-$C_{20}$aryl or $C_3$-$C_{20}$heteroaryl, each of which is unsubstituted or substituted by one or more halogen or $C_1$-$C_{20}$alkyl;
or $R_1$ is $C_1$-$C_{20}$alkoxy, $C_6$-$C_{20}$aryloxy or $C_3$-$C_{20}$heteroaryloxy;
$R_{1a}$ is hydrogen, $C_1$-$C_{20}$alkyl, $C_2$-$C_{20}$alkyl interrupted by one or more O, $C_2$-$C_{12}$alkenyl, $C_3$-$C_{20}$cycloalkyl, $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $C_1$-$C_{20}$alkyl, $OR_{3a}$, $SR_{4a}$, $NR_{5a}R_{6a}$, $COOR_{3a}$, (CO)—($C_1$-$C_8$alkyl) or benzoyl;
or $R_{1a}$ is $C_6$-$C_{20}$aryloxy or $C_3$-$C_{20}$heteroaryloxy, which $C_6$-$C_{20}$aryloxy or $C_3$-$C_{20}$heteroaryloxy is unsubstituted or substituted by benzoyl, or

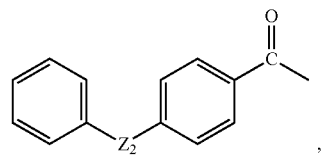, which benzoyl or

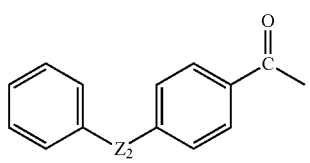

is unsubstituted or substituted by

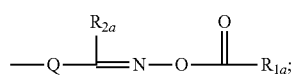;

$R_3$ is hydrogen, $(CO)R_{1a}$, $C_1$-$C_{20}$alkyl which is unsubstituted or substituted by one or more $C_3$-$C_8$cycloalkyl which is uninterrupted or interrupted by one or more O;
or $R_3$ is $C_2$-$C_{20}$alkyl interrupted by one or more O, which interrupted $C_2$-$C_{20}$alkyl is unsubstituted or substituted by one or more $C_3$-$C_8$cycloalkyl, OH or $(CO)OR_{3a}$;

or $R_3$ is $C_2$-$C_{12}$alkenyl, $C_3$-$C_{20}$cycloalkyl or $C_6$-$C_{20}$aryl, which $C_6$-$C_{20}$aryl is unsubstituted or substituted by one or more halogen or $C_1$-$C_{20}$alkyl;

$R_{3a}$ is $C_1$-$C_{20}$alkyl;

$R_4$ is hydrogen, $C_1$-$C_{20}$alkyl which is unsubstituted or substituted by one or more $OR_{3a}$, $(CO)OR_{3a}$, $C_3$-$C_8$cycloalkyl or $C_6$-$C_{20}$aryl;

or $R_4$ is $C_2$-$C_{20}$alkyl interrupted by one or more O, which interrupted $C_2$-$C_{20}$alkyl is unsubstituted or substituted by one or more OH or $(CO)OR_{3a}$;

or $R_4$ is $C_2$-$C_{12}$alkenyl or $C_3$-$C_{20}$cycloalkyl;

or $R_4$ is $C_6$-$C_{20}$aryl which is unsubstituted or substituted by one or more halogen or $C_2$-$C_{20}$alkyl which is uninterrupted or interrupted by one or more O;

$R_{4a}$ is $C_1$-$C_{20}$alkyl;

$R_5$ and $R_6$ independently of each other are hydrogen, $C_1$-$C_{20}$alkyl which is unsubstituted or substituted by one or more halogen, $OR_{3a}$, $SR_{4a}$, $(CO)OR_{3a}$, $C_3$-$C_8$cycloalkyl or $C_6$-$C_{20}$aryl;

or $R_5$ and $R_6$ independently of each other are $C_2$-$C_{20}$alkyl interrupted by one or more O, which interrupted $C_2$-$C_{20}$alkyl is unsubstituted or substituted by OH or SH;

or $R_5$ and $R_6$ independently of each other are $C_2$-$C_{12}$alkenyl, $C_3$-$C_{20}$cycloalkyl or $C_6$-$C_{20}$aryl;

or $R_5$ and $R_6$ together with the N-atom to which they are attached form a 5- or 6-membered saturated or unsaturated ring which is uninterrupted or interrupted by O, S or $NR_{5a}$;

$R_{5a}$ and $R_{6a}$ independently of each other are hydrogen or $C_1$-$C_{20}$alkyl;

$R_7$, $R_8$, $R_9$, $R_{10}$ and $R_{11}$ independently of each other are hydrogen, $C_1$-$C_{20}$alkyl, $OR_3$, $SR_4$, $NR_5R_6$, $COOR_3$, $(CO)R_{1a}$;

or $R_7$, $R_8$, $R_9$, $R_{10}$ and $R_{11}$ independently of each other are $C_1$-$C_{20}$alkyl substituted by one or more halogen, $OR_3$, $SR_4$, $NR_5R_6$, $(CO)OR_3$, $C_6$-$C_{20}$aryl or $C_3$-$C_8$cycloalkyl which is uninterrupted or interrupted by one or more O;

or $R_7$, $R_8$, $R_9$, $R_{10}$ and $R_{11}$ independently of each other are $C_2$-$C_{20}$alkyl interrupted by one or more O;

or $R_7$, $R_8$, $R_9$, $R_{10}$ and $R_{11}$ independently of each other are $C_6$-$C_{20}$aryl or $C_3$-$C_{20}$heteroaryl, which $C_6$-$C_{20}$aryl or $C_3$-$C_{20}$heteroaryl is unsubstituted or substituted by one or more halogen, $OR_3$, $SR_4$, $NR_5R_6$, $COOR_3$, $(CO)R_{1a}$ or

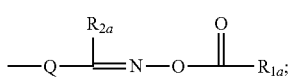;

or $R_8$ and $R_9$, $R_9$ and $R_{10}$, or $R_{10}$ and $R_{11}$ are

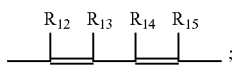;

$R_{12}$, $R_{13}$, $R_{14}$ and $R_{15}$ independently of each other are hydrogen or $C_1$-$C_{20}$alkyl;

$Ar_1$ is $C_6$-$C_{20}$aryl, $C_3$-$C_{20}$heteroaryl, $C_6$-$C_{20}$aroyl, $C_3$-$C_{20}$heteroarylcarbonyl or

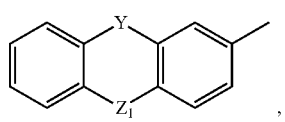, which $C_6$-$C_{20}$aryl, $C_3$-$C_{20}$heteroaryl, $C_6$-$C_{20}$aroyl, $C_3$-$C_{20}$heteroarylcarbonyl or

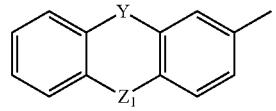

is unsubstituted or substituted by one or more halogen, $COOR_3$, $(CO)R_{1a}$,

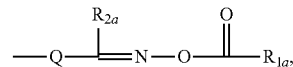

$OR_3$, $SR_4$, $NR_5R_6$, $C_1$-$C_{20}$alkyl, $C_2$-$C_{20}$alkyl which is interrupted by one or more O, $C_2$-$C_{12}$alkenyl, $C_3$-$C_{20}$cycloalkyl or phenyl;

or $Ar_1$ is

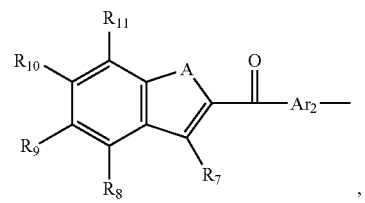

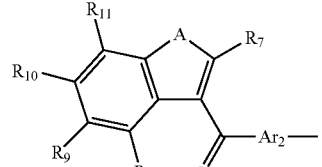 or

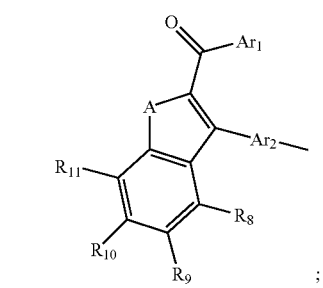;

$Ar_2$ is phenylene, naphthylene,

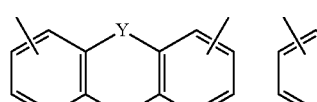, 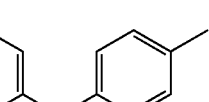,

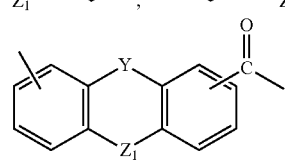

or

-continued

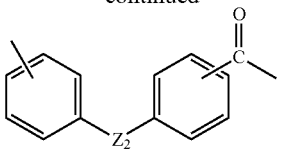, which phenylene, naphthylene,

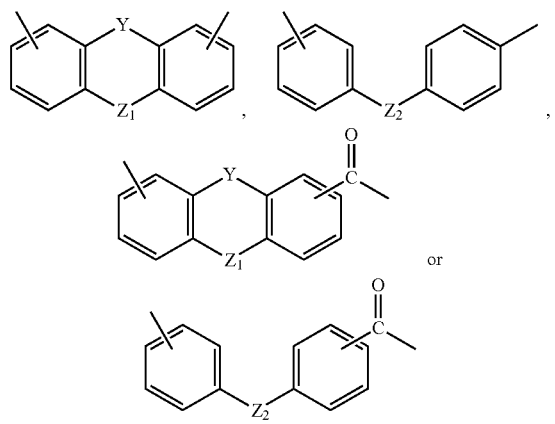

is unsubstituted or substituted by one or more halogen, COOR$_3$, (CO)R$_{1a}$,

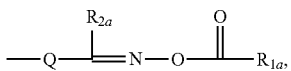

OR$_3$, SR$_4$, NR$_5$R$_6$, C$_1$-C$_{20}$alkyl, C$_2$-C$_{12}$alkenyl, C$_3$-C$_{20}$cycloalkyl, phenyl or C$_2$-C$_{20}$alkyl which is interrupted by one or more O;

Y is a direct bond, O, S, NR$_5$ or CO;

Z$_1$ is O, S, CO or CR$_{16}$(R$_{17}$);

Z$_2$ is a direct bond, O, S or NR$_5$; and

Q is CO or a direct bond.

3. Compounds of the formula (I) according to claim 1, wherein

X is

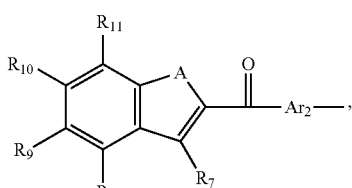

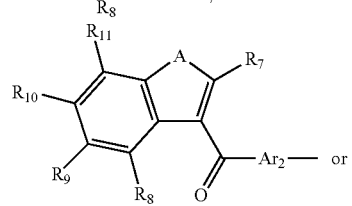

-continued

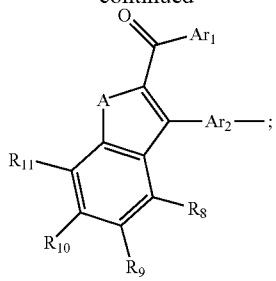

A is O, S or NR$_5$;

R$_1$ is C$_1$-C$_{20}$alkyl, C$_6$-C$_{20}$aryl or C$_1$-C$_{20}$alkoxy;

R$_{1a}$ is C$_1$-C$_{20}$alkyl or C$_6$-C$_{20}$aryl;

R$_3$ is C$_1$-C$_{20}$alkyl or R$_3$ together with one of the carbon atoms of R$_2$ forms a 5- or 6-membered, preferably 6-membered, saturated ring;

R$_4$ is C$_6$-C$_{20}$aryl;

R$_5$ and R$_6$ independently of each other are O(CO)R$_{1a}$, (CO)R$_{1a}$ or C$_1$-C$_{20}$alkyl;

R$_7$, R$_8$, R$_9$, R$_{10}$ and R$_{11}$ independently of each other are hydrogen, C$_1$-C$_{20}$alkyl, halogen, NO$_2$, OR$_3$, (CO)R$_{1a}$ or C$_6$-C$_{20}$aryl;

or R$_8$ and R$_9$ are

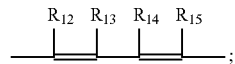

R$_{12}$, R$_{13}$, R$_{14}$ and R$_{15}$ are hydrogen or C$_1$-C$_4$alkyl, preferably hydrogen;

R$_{16}$ and R$_{17}$ are hydrogen;

or R$_{16}$ and R$_{17}$ together with the carbon atom to which they are attached form a 5- or 6-membered saturated ring;

Ar$_1$ is C$_6$-C$_{20}$aryl or

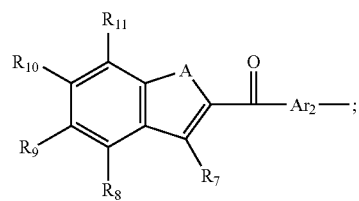

Ar$_2$ is

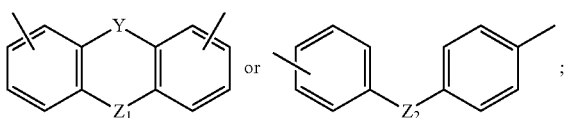

Y is a direct bond;

Z$_1$ is O, S or CR$_{16}$(R$_{17}$); and

Z$_2$ is O or S.

4. A photopolymerizable composition comprising
(a) at least one ethylenically unsaturated photopolymerizable compound and
(b) as photoinitiator, at least one compound of the formula I as defined in claim 1.

5. A photopolymerizable composition according to claim 4, wherein the component (a) is a resin obtained by the reaction of a saturated or unsaturated polybasic acid anhydride with a product of the reaction of an epoxy resin and an unsaturated monocarboxylic acid.

6. A photopolymerizable composition according to claim 4, further comprising at least one photoinitiator (c) and other additives (d).

7. A photopolymerizable composition according to claim 6 wherein the additive (d) is selected from a pigment, or a mixture of pigments, or a dye, or a mixture of dyes, or a mixture of one or more pigments with one or more dyes.

8. A photopolymerizable composition according to claim 6 wherein the additive (d) is a dispersant or a mixture of dispersants.

9. A photopolymerizable composition according to claim 6, further comprising a binder polymer (e).

10. The photopolymerizable composition according to claim 9, wherein the binder is a-copolymer of methacrylate and methacrylic acid.

11. A photopolymerizable composition according to claim 4, comprising 0.05 to 25% by weight of the photoinitiator (b), based on the composition.

12. A photopolymerizable composition according to claim 4, further comprising a photosensitizer selected from the group consisting of benzophenone, benzophenone derivatives, thioxanthone, thioxanthone derivatives, anthraquinone, anthraquinone derivatives, coumarin and coumarine derivatives.

13. A process for the photopolymerization of compounds containing ethylenically unsaturated double bonds, the process comprising irradiating a composition according to claim 4 with electromagnetic radiation in the range from 150 to 600 nm, or with an electron beam or with X-rays.

14. A process according to claim 13 for producing pigmented and non-pigmented paints, varnishes, powder coatings, printing inks, printing plates, adhesives, dental compositions, gel coats, photoresists for electronics, for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects, image recording materials, microelectronic circuits, decolorizing materials, bank/pixel definition layers for OLED, sealants for LCD and OLED, insulation/passivation layers for LCD and OLED, insulation for metal wiring/transparent conductive films for touch panel, coatings for touch panel, decorative inks for touch panel, protective films for touch panel or etching resists for touch panel.

15. A substrate coated on at least one surface with a composition according to claim 4.

16. A process for the photographic production of relief images comprising providing the coated substrate according to claim 15, subjecting the substrate to imagewise exposure, and removing unexposed portions with a developer.

17. Compounds of formula (IA)

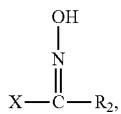

(IA)

wherein
X is

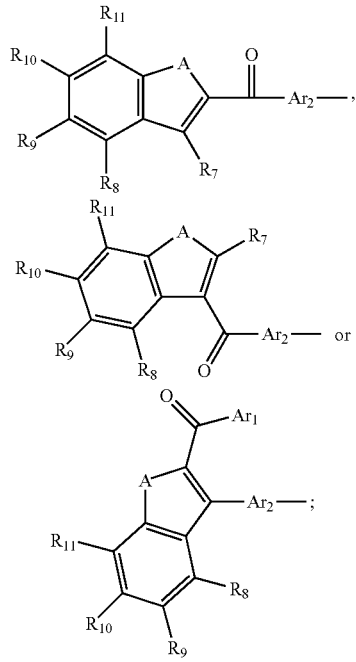

$R_2$ is $C_1$-$C_{20}$alkyl which is substituted by $C_3$-$C_8$cycloalkyl;

$Ar_1$ is $C_6$-$C_{20}$aryl, $C_3$-$C_{20}$heteroaryl, $C_6$-$C_{20}$aroyl, $C_3$-$C_{20}$heteroarylcarbonyl or

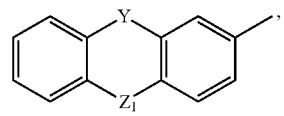

which $C_6$-$C_{20}$aryl, $C_3$-$C_{20}$heteroaryl, $C_6$-$C_{20}$aroyl, $C_3$-$C_{20}$heteroarylcarbonyl or

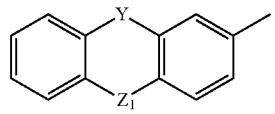

is unsubstituted or substituted by one or more substituents selected from the group consisting of halogen, CN, $NO_2$, $COOR_3$, $(CO)R_{1a}$, $(CO)NR_5R_6$, $PO(OR_{1a})_2$, $S(O)_mR_{1a}$,

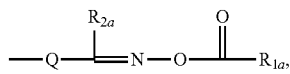

$OR_3$, $SR_4$, $NR_5R_6$, wherein the substituents $OR_3$, $SR_4$ or $NR_5R_6$ optionally form 5- or 6-membered rings via the radicals $R_3$, $R_4$, $R_5$ or $R_6$ with further substituents on the phenyl ring, $C_1$-$C_{20}$alkyl which is unsubstituted or substituted by one or more halogen, $COOR_3$, CONR$_5$R$_6$, phenyl, C$_3$-C$_8$cycloalkyl, C$_3$-C$_{20}$heteroaryl, OR$_3$, SR$_4$ or NR$_5$R$_6$, C$_2$-C$_{20}$alkyl which is interrupted by one or more O, S or NR$_5$, C$_2$-C$_{12}$alkenyl or C$_3$-C$_{20}$cycloalkyl, which C$_2$-C$_{12}$alkenyl or C$_3$-C$_{20}$cycloalkyl is uninterrupted or interrupted by one or more O, S, CO, NR$_5$ or COOR$_3$, phenyl, naphthyl, benzoyl and naphthoyl, which phenyl, naphthyl, benzoyl or naphthoyl is unsubstituted or substituted by OR$_3$, SR$_4$ or NR$_5$R$_6$;

or Ar$_1$ is.

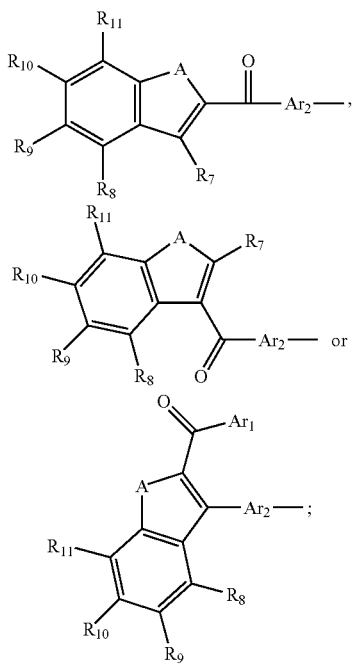

18. A color filter comprising
red, green and blue picture elements and optionally a black matrix, each of the elements including a photosensitive resin and a pigment on a transparent substrate, and a transparent electrode either on the surface of the substrate or on the surface of the picture elements, wherein said photosensitive resin comprises a polyfunctional acrylate monomer, an organic polymer binder and a photopolymerization initiator of formula I or II as defined in claim 1.

19. A process for the preparation of a compound of the formula I as defined in claim 1 by reacting the corresponding oxime compound of the formula (1A)

(IA)

wherein X, Ar$_1$, and R$_2$ are as defined in claim 1,
with an acyl halide of the formula III or an anhydride of the formula IV

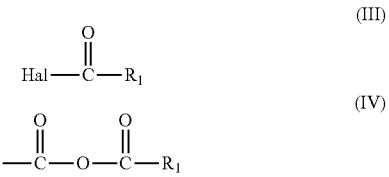

(III)

(IV)

wherein Hal is a halogen, in particular Cl, and R$_{14}$ is as defined in claim 17, in the presence of a base or a mixture of bases.

* * * * *